United States Patent
Tomczuk et al.

(10) Patent No.: US 6,344,484 B1
(45) Date of Patent: Feb. 5, 2002

(54) TYROSINE ALKOXYGUANIDINES AS INTEGRIN INHIBITORS

(75) Inventors: Bruce E. Tomczuk, Collegeville; Yu Kai Lee, Exton, both of PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/502,006

(22) Filed: Feb. 11, 2000

Related U.S. Application Data

(60) Provisional application No. 60/119,864, filed on Feb. 12, 1999.

(51) Int. Cl.$^7$ ...................... A61K 31/216; C07C 279/14
(52) U.S. Cl. ......................... 514/565; 514/538; 560/34; 562/434
(58) Field of Search ........................... 560/34; 514/505, 514/538; 562/439

(56) References Cited

U.S. PATENT DOCUMENTS

| | | | |
|---|---|---|---|
| 5,618,843 A | 4/1997 | Fisher et al. | 514/567 |
| 5,731,324 A | 3/1998 | Fisher et al. | 514/320 |
| 5,741,796 A | 4/1998 | Hartman et al. | 514/300 |
| 6,020,362 A | 2/2000 | Fisher et al. | 514/456 |

FOREIGN PATENT DOCUMENTS

| | | |
|---|---|---|
| WO | WO 97/06791 | 2/1997 |
| WO | WO 97/23451 | 7/1997 |
| WO | WO 97/36859 | 10/1997 |
| WO | WO 97/45137 | 12/1997 |
| WO | WO 98/00395 | 1/1998 |

OTHER PUBLICATIONS

Albelda, S.M., et al., "Integrin Distribution in Malignant Melanoma: Association of the $\beta_3$ Subunit with Tumor Progression," *Cancer Res.* 50:6757–6764 (1990).

Albelda, S.M., "Biology of Disease. Role of Integrins and Other Cell Adhesion Molecules in Tumor Progression and Metastasis," *Lab. Invest.* 68:4–14 (1993).

Bergeron, R.J., and McManis, J.S., "Total Synthesis of (±)-15-Deoxyspergualin," *J. Org. Chem.* 52:1700–1703 (1987).

Bernatowicz, M.S., et al., "1H–Pyrazole–1–carboxamidine Hydrochloride: An Attractive Reagent for Guanylation of Amines and Its Application to Peptide Synthesis," *J. Org. Chem.* 57:2497–2502 (1992).

Boudreau, N., and Rabinovitch, M., "Developmentally Regulated Changes in Extracellular Matrix in Endothelial and Smooth Muscle Cells in the Ductus Arteriosus May be Related to Intimal Proliferation," *Lab. Invest.* 64:187–199 (1991).

Brooks, P.C., "Integrin $\alpha v\beta 3$: A Therapeutic Target," *DN&P* 10(8):456–461 (1997).

Brooks, P.C., et al., "Integrin $\alpha_v\beta_3$ Antagonists Promote Tumor Regression by Inducing Apoptosis of Angiogenic Blood Vessels," *Cell* 79:1157–1164 (1994).

Brooks, P.C., et al., "Requirement of Vascular Integrin $\alpha_v\beta_3$ for Angiogenesis," *Science* 264:569–571 (1994).

Brooks, P.C., et al., "Antiintegrin $\alpha_v\beta_3$ blocks human breast cancer growth and angiogenesis in human skin," *J. Clin. Invest.* 96:1815–1822 (1995).

Brooks, P.C., "Cell adhesion molecules in angiogenesis," *Cancer Met. Rev.* 15:187–194 (1996).

Cheresh, D.A., "Structure, function and biological properties of integrin $\alpha_v\beta_3$ on human melanoma cells," *Cancer Met. Rev.* 10:3–10 (1991).

Choi, E.T., et al., "Inhibition of neointimal hyperplasia by blocking $\alpha_v\beta_3$ Integrin with a small peptide antagonist GpenGRGDSPCA," *J. Vasc. Surg.* 19:125–134 (1994).

Dennis, M.S., et al., "Binding Interactions of Kistrin With Platelet Glycoprotein IIb–IIIa: Analysis by Site–Directed Mutagenesis," *Proteins* 15:312–321 (1993).

Enenstein, J., and Kramer, R.H., "Confocal Microscopic Analysis of Integrin Expression on the Microvasculature and its Sprouts in the Neonatal Foreskin," *J. Invest. Dermatol.* 103:381–386 (1994).

Fisher, J.E., et al., "Inhibition of Osteoclastic Bone Resorption in vivo by Echistatin, an 'Arginyl–Glycyl–Aspartyl' (RGD)–Containing Protein," *Endocrinology* 132:1411–1413 (1993).

(List continued on next page.)

*Primary Examiner*—Robert Gerstl
(74) *Attorney, Agent, or Firm*—Sterne, Kessler, Goldstein & Fox PLLC

(57) ABSTRACT

The present invention relates to novel tyrosine alkoxyguanidine compounds that are inhibitors of alpha V ($\alpha v$) integrins, for example $\alpha v\beta 3$ and $\alpha v\beta 5$ integrins, their pharmaceutically acceptable salts, and pharmaceutical compositions thereof. The compounds may be used in the treatment of pathological conditions mediated by $\alpha v\beta 3$ and $\alpha v\beta 5$ integrins, including conditions such as tumor growth, metastasis, restenosis, osteoporosis, inflammation, macular degeneration, diabetic retinopathy, and rheumatoid arthritis. The compounds have the general formula:

IV

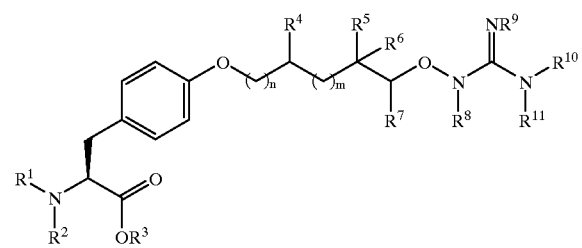

where $R^1$, $R^2$, $R^3$, $R^4$, $R^5$, $R^6$, $R^7$, $R^8$, $R^9$, $R^{10}$, $R^{11}$, m and n are defined herein.

33 Claims, No Drawings

OTHER PUBLICATIONS

Friedlander, M., et al., "Definition of Two Angiogenic Pathways by Distinct α, Integrins," *Science* 270:1500–1502 (1995).

Gladson, C L., "Expression of Integrin $\alpha_v\beta_3$ in Small Blood Vessels of Glioblastoma Tumors," *J. Neuropathol. Exp. Neurol.* 55:1143–1149 (1996).

Greenspoon, N., et al., "Structural Analysis of Integrin Recognition and the Inhibition of Integrin–Mediated Cell Functions by Novel Nonpeptidic Surrogates of the Arg–Gly– Asp Sequence," *Biochemistry* 32:1001–1008 (1993).

Hardan. I., et al., "Inhibition of Metastatic Cell Colonization in Murine Lungs and Tumor–Induced Morbidity by Non–Peptidic Arg–Gly–Asp Mimetics," *Int. J. Cancer* 55:1023–1028 (1993).

Hershkoviz, R., et al., "Inhibition of CD4+ T Lymphocyte binding to fibronectin and immune–cell accumulation in inflammatory sites by non–peptidic mimetics of Arg–Gly–Asp," *Clin. Exp. Immunol.* 95:270–276 (1994).

Horton, M., "Current Status Review. Vitronectin receptor: tissue specific expression or adaptation to culture?," *Int. J. Exp. Pathol.* 71:741–759 (1990).

Hynes, R.O., "Integrins: Versatility, Modulation, and Signaling in Cell Adhesion," *Cell* 69:11–25 (1992).

Juliano, R., "Signal transduction by integrins and its role in the regulation of tumor growth," *Cancer Met. Rev.* 13:25–30 (1994).

Ku, T.W., et al., "Direct Design of a Potent Non–Peptide Fibrinogen Receptor Antagonist Based on the Structure and Conformation of a Highly Constrained Cyclic RGD Peptide," *J. Amer. Chem. Soc.* 115:8861–8862 (1993).

Luna, J., et al., "Antagonists of Integrin $\alpha_v\beta_3$ Inhibit Retinal Neovascularization in a Murine Model," *Lab. Invest.* 75(4):563–573 (1996).

Marquardt, D.W., "An Algorithm for Least–Squares Estimation of Nonlinear Parameters," *J. Soc. Indust. Appl. Math.* 11:431–441 (1963).

Miller, A.E., and Bischoff, J.J., "A Facile Conversion of Amino Acids to Guanidino Acids," *Synthesis* 9:777–779 (1986).

Mitsunobu, O., "The Use of Diethyl Azodicarboxylate and Triphenylphosphine in Synthesis and Transformation of Natural Products," *Synthesis* 1:1–28 (1981).

Nicosia, R.F., and Madri, J.A., "The Microvascular Extracellular Matrix. Developmental Changes During Angiogenesis in the Aortic Ring–Plasma Clot Model," *Amer. J. Pathol.* 128:78–90 (1987).

Niiya, K., et al., "Increased Surface Expression of the Membrane Glycoprotein IIb/IIIa Complex Induced by Platelet Activation. Relationship to the Binding of Fibrinogen and Platelet Aggregation," *Blood* 70:475–483 (1987).

Niiya, K., et al., "Increased Surface Expression of the Membrane Glycoprotein IIb/IIIa Complex Induced by Platelet Activation. Relationship to the Binding of Fibrinogen and Platelet Aggregation," *Blood* 70:475–483 (1987).

Nip, J., et al., "Coordinated Expression of the Vitronectin Receptor and the Urokinase–type Plasminogen Activator Receptor in Metastatic Melanoma Cells," *J. Clin. Invest.* 95:2096–2103 (1995).

Okada, Y., et al., "Integrin $\alpha_v\beta_3$ Is Expressed in Selected Microvessels after Focal Cerebral Ischemia," *Amer. J. Pathol.* 149:37–44 (1996).

Ruoslahti, E., and Reed, J.C., "Anchorage Dependence, Integrins, and Apoptosis," *Cell* 77:477–478 (1994).

Ruoslahti, E., and Giancotti, F.G., "Integrins and Tumor Cell Dissemination," *Cancer Cells* 1:119–126 (1989).

Sato, M., et al., "Echistatin Is a Potent Inhibitor of Bone Resorption in Culture," *J. Cell Biol.* 111:1713–1723 (1990).

Shattil, S.J., "Function and Regulation of the $\beta_3$ Integrins in Hemostasis and Vascular Biology," *Thromb. Haemost.* 74:149–155 (1995).

Topol, E.J., et al., "Randomised trial of coronary intervention with antibody against platelet IIb/IIIa Integrin for reduction of clinical restenosis: results at six months," *Lancet* 343:881–886 (1994).

White, J.M., "Integrins as virus receptors," *Current Biology* 3(9):596–599 (1993).

Yun, Z., et al., "Involvement of Integrin $\alpha_v\beta_3$ in Cell Adhesion, Motility, and Liver Metastasis of Murine RAW117 Large Cell Lymphoma," *Cancer Res.* 56:3103–3111 (1996).

United States Pharmacopeia/National Formulary for 1995, published by United States Pharmacopeial Convention, Inc., Rockville, Maryland, p. 1636 (1994).

TYROSINE ALKOXYGUANIDINES AS INTEGRIN INHIBITORS

This application claims the benefit, under 35 U.S.C. §119(e), of the earlier filing date of U.S. Provisional Application No. 60/119,864, filed on Feb. 12, 1999, which is fully incorporated by reference herein.

FIELD OF THE INVENTION

The present invention relates to novel tyrosine alkoxyguanidine compounds that are inhibitors of alpha V (αv) integrins, for example αvβ3 and αvβ5 integrins, their pharmaceutically acceptable salts, and pharmaceutical compositions thereof.

BACKGROUND OF THE INVENTION

Integrins are cell surface glycoprotein receptors which bind extracellular matrix proteins and mediate cell-cell and cell-extracellular matrix interactions (generally referred to as cell adhesion events) (Hynes, R. O., Cell 69:11–25 (1992)). These receptors are composed of noncovalently associated alpha (α) and beta (β) chains which combine to give a variety of heterodimeric proteins with distinct cellular and adhesive specificities (Albeda, S. M., Lab. Invest. 68:4–14 (1993)). Recent studies have implicated integrins in the regulation of cellular adhesion, migration, invasion, proliferation, apoptosis and gene expression (Albeda, S. M., Lab. Invest. 68:4–14 (1993); Juliano, R., Cancer Met. Rev. 13:25–30 (1994); Ruoslahti, E. and Reed, J. C., Cell 77:477–478 (1994); and Ruoslahti, E. and Giancotti, F. G., Cancer Cells 1:119–126 (1989)).

One member of the integrin family which has been shown to play a significant role in a number of pathological conditions is the integrin αvβ3, or vitronectin receptor (Brooks, P. C., DN&P 10(8):456–461 (1997)). This integrin binds a variety of extracellular matrix components and other ligands, including fibrin, fibrinogen, fibronectin, vitronectin, laminin, thrombospondin, and proteolyzed or denatured collagen (Cheresh, D. A., Cancer Met. Rev. 10:3–10 (1991) and Shattil, S. J., Thromb. Haemost. 74:149–155 (1995)). The two related αv integrins, αvβ5 and αvβ1 (also vitronectin receptors), are more specific and bind vitronectin (αvβ5) or fibronectin and vitronectin (αvβ1) exclusively (Horton, M., Int. J. Exp. Pathol. 71:741–759 (1990)). αvβ3 and the other integrins recognize and bind to their ligands through the tripeptide sequence Arg-Gly-Asp ("RGD") (Cheresh, D. A., Cancer Met. Rev. 10:3–10 (1991) and Shattil, S. J., Thromb. Haemost. 74:149–155 (1995)) found within all the ligands mentioned above.

The αvβ3 integrin has been implicated in a number of pathological processes and conditions, including metastasis and tumor growth, pathological angiogenesis, and restenosis. For example, several studies have clearly implicated αvβ3 in the metastatic cascade (Cheresh, D. A., Cancer Met. Rev. 10:3–10 (1991); Nip, J. et al., J. Clin. Invest. 95:2096–2103 (1995); and Yun, Z., et al., Cancer Res. 56:3101–3111 (1996)). Vertically invasive lesions in melanomas are also commonly associated with high levels of αvβ3, whereas horizontally growing noninvasive lesions have little if any αvβ3 (Albeda, S. M., et al., Cancer Res. 50:6757–6764 (1990)). Moreover, Brooks et al. (in Cell 79:1157–1164 (1994)) have demonstrated that systemic administration of αvβ3 antagonists disrupts ongoing angiogenesis on chick chorioallantoic membrane ("CAM"), leading to the rapid regression of histologically distinct human tumors transplanted onto the CAM. These results indicate that antagonists of αvβ3 may provide a therapeutic approach for the treatment of neoplasia (solid tumor growth).

αvβ3 has also been implicated in angiogenesis, which is the development of new vessels from preexisting vessels, a process that plays a significant role in a variety of normal and pathological biological events. It has been demonstrated that αvβ3 is up-regulated in actively proliferating blood vessels undergoing angiogenesis during wound healing as well as in solid tumor growth. Also, antagonists of αvβ3 have been shown to significantly inhibit angiogenesis induced by cytokines and solid tumor fragments (Brooks, P. C., et al., Science 264:569–571 (1994); Enenstein, J. and Kramer, R. H., J. Invest. Dermatol. 103:381–386 (1994); Gladson, C. L., J. Neuropathol. Exp. Neurol 55:1143–1149 (1996); Okada, Y., et al., Amer. J. Pathol. 149:37–44 (1996); and Brooks, P. C., et al., J. Clin. Invest. 96:1815–1822 (1995)). Such αvβ3 antagonists would be useful for treating conditions that are associated with pathological angiogenesis, such as rheumatoid arthritis, diabetic retinopathy, macular degeneration, and psoriasis (Nicosia, R. F. and Madri, J. A., Amer. J. Pathol. 128:78–90 (1987); Boudreau, N. and Rabinovitch, M., Lab. Invest. 64:187–99 (1991); and Brooks, P. C., Cancer Met. Rev. 15:187–194 (1996)).

There is also evidence that αvβ3 plays a role in neointimal hyperplasia after angioplasty and restenosis. For example, peptide antagonists and monoclonal antibodies directed to both αvβ3 and the platelet receptor IIbβ3 have been shown to inhibit neointimal hyperplasia in vivo (Choi, E. T., et al., J. Vasc. Surg. 19:125–134 (1994); and Topol, E. J., et al., Lancet 343:881–886 (1994)), and recent clinical trials with a monoclonal antibody directed to both IIbβ3 and αvβ3 have resulted in significant reduction in restenosis, providing clinical evidence of the therapeutic utility of β3 antagonists (Topol, E. J., et al., Lancet 343:881–886 (1994)).

It has also been reported that αvβ3 is the major integrin on osteoclasts responsible for attachment to bone. Osteoclasts cause bone resorption. When bone resorbing activity exceeds bone forming activity, the result is osteoporosis, a condition which leads to an increased number of bone fractures, incapacitation and increased mortality. Antagonists of αvβ3 have been shown to be potent inhibitors of osteoclastic activity both in vitro (Sato, M., et al., J. Cell Biol. 111:1713–1723 (1990)) and in vivo (Fisher, J. E., et al., Endocrinology 132:1411–1413 (1993)).

Lastly, White (in Current Biology 3(9):596–599 (1993)) has reported that adenovirus uses αvβ3 for entering host cells. The αvβ3 integrin appears to be required for endocytosis of the virus particle and may be required for penetration of the viral genome into the host cell cytoplasm. Thus compounds which inhibit αvβ3 could be useful as antiviral agents.

The αvβ5 integrin has been implicated in pathological processes as well. Friedlander et al. have demonstrated that a monoclonal antibody for αvβ5 can inhibit VEGF-induced angiogenesis in rabbit cornea and chick chorioalloantoic membrane, indicating that the αvβ5 integrin plays a role in mediating growth factor-induced angiogenesis (Friedlander, M. C., et al., Science 270:1500–1502 (1995)). Compounds that act as αvβ5 antagonists could be used to inhibit pathological angiogenesis in tissues of the body, including ocular tissue undergoing neovascularization, inflamed tissue, solid tumors, metastases, or tissues undergoing restenosis.

Discovery of the involvement of αvβ3 and αvβ5 in such processes and pathological conditions has led to an interest in these integrins as potential therapeutic targets, as suggested in the preceding paragraphs. A number of specific antagonists of αvβ3 and αvβ5 that can block the activity of these integrins have been developed. One major group of such antagonists includes nonpeptide mimetics and organic-type compounds. For example, a number of organic non-peptidic mimetics have been developed that appear to inhibit tumor cell adhesion to a number of αvβ3 ligands, including vitronectin, fibronectin, and fibrinogen (Greenspoon, N., et al., *Biochemistry* 32:1001–1008 (1993); Ku, T. W., et al., *J. Amer. Chem. Soc.* 115:8861–8862 (1993); Hershkoviz, R., et al., *Clin. Exp. Immunol.* 95:270–276 (1994); and Hardan, L., et al., *Int. J. Cancer* 55:1023–1028 (1993)).

Additional organic compounds developed specifically as αvβ3 or αvβ5 integrin antagonists or as compounds useful in the treatment of αv-mediated conditions have been described in several recent publications.

For example, U.S. Pat. No. 5,741,796, issued Apr. 21, 1998, discloses pyridyl and naphthyridyl compounds for inhibiting osteoclast-mediated bone resorption.

PCT Published Application WO 97/45137, published Oct. 9, 1997, discloses non-peptide sulfotyrosine derivatives, as well as cyclopeptides, fusion proteins, and monoclonal antibodies, that are useful as inhibitors of αvβ3 integrin-mediated angiogenesis.

PCT Published Application WO 97/36859, published Oct. 9, 1997, discloses para-substituted phenylpropanoic acid derivatives of the general formula:

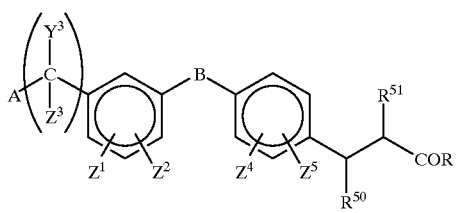

I where A is:

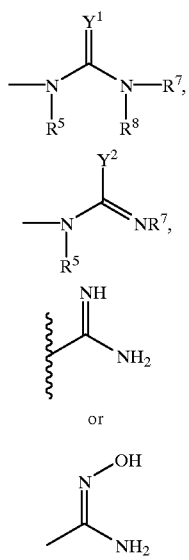

B is —CH$_2$CONH—, —CONR$^{52}$—(CH$_2$)$_p$—, —C(O)O—, —SO$_2$NH—, —CH$_2$O—, or —OCH$_2$—;

Y$^1$ is selected from the group consisting of N—R$^2$, O and S;

Y$^3$ and Z$^3$ are independently selected from the group consisting of H, alkyl, aryl, cycloalkyl and aralkyl, or Y$^3$ and Z$^3$ taken together with C form a carbonyl;

R$^{50}$ is selected from the group consisting of H, alkyl, aryl, carboxyl derivative and —CONHCH$_2$CO$_2$R$^{53}$, wherein R$^{53}$ is H or lower alkyl; and R$^{51}$ is selected from the group consisting of H, alkyl, carboxyl derivatives,

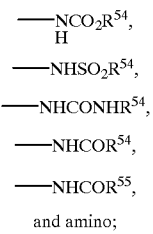

and amino;

wherein R$^{54}$ is selected from the group consisting of H, alkyl, cycloalkyl, aryl, aralkyl, aralkenyl and aryl substituted by one or more alkyl or halo; and wherein R$^{55}$ is selected from the group consisting of N-substituted pyrrolidinyl, piperidinyl and morpholinyl.

The publication also discloses the use of the compounds as αvβ3 integrin antagonists.

PCT Published Application WO 97106791, published Feb. 1997, discloses methods for inhibition of angiogenesis in tissue using vitronectin αvβ5 antagonists.

More recently, PCT Published Application WO 97/23451, published Jul. 3, 1997, discloses tyrosine derivatives of the general formula:

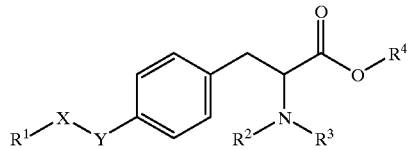

II wherein

X is C$_{1-6}$alkylene or 1,4-piperidyl;

Y is absent, O, CONH or —C≡C—;

R$^1$ is H, CN, N$_3$, NH$_2$, H$_2$N—C(=NH), or H$_2$N—C(=NH)—NH, where the primary amino groups can also be provided with conventional amino protective groups;

R$^2$ and R$^3$ are independently H, A, A—SO$_2$—, Ar—SO$_2$—, camphor-10-SO$_2$—, COOA or a conventional amino protective group;

A and R$^4$ are independently H, C$_{1-10}$alkyl, or benzyl; and

Ar is phenyl or benzyl, each of which is unsubstituted or monosubstituted by CH$_3$;

and their physiologically acceptable salts.

The disclosed compounds are described as αv-integrin inhibitors (especially αvβ3 inhibitors) useful in the treatment of tumors, osteoporoses, and osteolytic disorders and for suppressing angiogenesis.

PCT Published Application WO 98/00395, published Jan. 8, 1998, discloses novel tyrosine and phenylalanine derivatives as αv integrin and GPIIb/IIIa antagonists having the general formula:

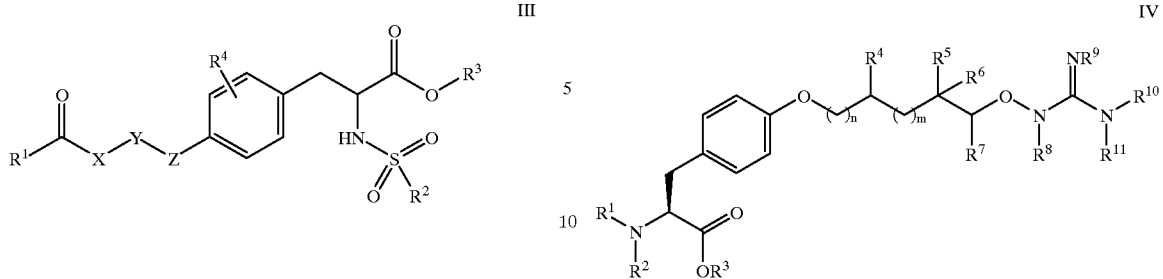

wherein

X can be, among other groups, alkyl, aryl or cycloalkyl;

Y and Z can be alkyl, O, S, NH, C(=O), CONH, NHCO, C(=S), SO$_2$NH, NHSO$_2$, CA=CA' or —C≡C—;

$R^1$ can be H$_2$N—C(=NH) or H$_2$N—(C=NH)—NH;

$R^2$ is A, aryl or aralkyl;

$R^3$ is hydrogen or A;

$R^4$ is hydrogen, halogen, OA, NHA, NAA', —NH-Acyl, —O-Acyl, CN, NO$_2$, SA, SOA, SO$_2$A, SO$_2$Ar or SO$_3$H; and A and A' can be hydrogen, alkyl or cycloalkyl.

The publication discloses the use of the compounds in pharmaceutical preparations for the treatment of thrombosis, infarction, coronary heart disease, tumors, arteriosclerosis, infection and inflammation.

A need continues to exist for non-peptide compounds that are potent and selective integrin inhibitors, and which possess greater bioavailability or fewer side-effects than currently available integrin inhibitors.

SUMMARY OF THE INVENTION

The present invention is directed to novel tyrosine alkoxyguanidine compounds having Formula IV (below). Also provided is a process for preparing compounds of Formula IV. The novel compounds of the present invention exhibit inhibition of αvβ3 and αvβ5 integrin receptor binding. Also provided is a method of treating αvβ3 integrin- and αvβ5 integrin-mediated pathological conditions such as tumor growth, metastasis, osteoporosis, restenosis, inflammation, macular degeneration, diabetic retinopathy, and rheumatoid arthritis in a mammal in need of such treatment comprising administering to said mammal an effective amount of a compound of Formula IV. Further provided is a pharmaceutical composition comprising a compound of Formula IV and one or more pharmaceutically acceptable carriers or diluents.

DETAILED DESCRIPTION OF THE PREFERRED EMBODIMENTS

The present invention is directed to compounds of Formula IV:

and pharmaceutically acceptable salts thereof; wherein $R^1$ and $R^2$ independently represent hydrogen, alkyl, aralkyl, $R^{12}SO_2$, $R^{12}OOC$, or $R^{12}CO$, where $R^{12}$ is (i) hydrogen, or (ii) alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;

and when $R^1$ or $R^2$ is $R^{12}CO$, then $R^{12}$ can also be N-attached pyrrolidinyl, piperidinyl or morpholinyl;

$R^3$ is hydrogen or a functionality which acts as a prodrug (i.e., converts to the active species by an endogenous biological process such as an esterase, lipase, or other hydrolases), such as alkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl;

$R^4$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di- alkylamino;

$R^5$, $R^6$, and $R^7$ are independently hydrogen, alkyl, aralkyl, aryl, hydroxyalkyl, aminoalkyl, monoalkylaminoalkyl, dialkylaminoalkyl or carboxyalkyl;

or $R^4$ and $R^5$ are taken together to form —(CH$_2$)$_y$—, where y is zero (a bond), 1 or 2, while $R^6$ and $R^7$ are defined as above; or $R^4$ and $R^7$ are taken together to form —(CH$_2$)$_q$—, where q is zero (a bond), or 1 to 8, while $R^5$ and $R^6$ are defined as above; or $R^5$ and $R^6$ are taken together to form —(CH$_2$)$_r$—, where r is 2–8, while $R^4$ and $R^7$ are defined as above;

$R^8$ is hydrogen, alkyl, aralkyl, hydroxyalkyl, aminoalkyl, monoalkylaminoalkyl, dialkylaminoalkyl or carboxyalkyl;

$R^9$, $R^{10}$, and $R^{11}$ are independently hydrogen, alkyl, aralkyl, hydroxy, alkoxy, aryloxy, aralkoxy, alkoxycarbonyloxy, cyano or —COOR$^w$;

$R^w$ is alkyl, cycloalkyl, phenyl, benzyl,

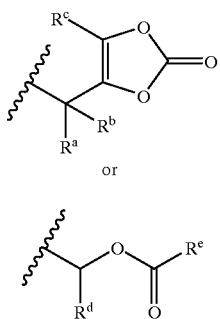

where $R^a$ and $R^b$ are independently hydrogen, alkyl, alkenyl or phenyl; $R^c$ is hydrogen, alkyl, alkenyl or phenyl; $R^d$ is hydrogen, alkyl, alkenyl or phenyl; and $R^e$ is aralkyl or alkyl;

n is from zero to 8; m is from zero to 4; provided that n is other than zero when $R^4$ is hydroxy, alkoxy, aralkoxy, aryloxy, heteroaryloxy, or mono- or di-alkylamino.

Preferred compounds of the present invention are those of Formula IV wherein:

$R^1$ and $R^2$ independently represent hydrogen, $C_{1-6}$alkyl, $C_{6-10}$ar($C_{1-6}$)alkyl, $R^{12}SO_2$, $R^{12}OOC$ or $R^{12}CO$, where $R^{12}$ is hydrogen, $C_{1-6}$alkyl, $C_{6-10}$ar($C_{1-6}$)alkyl, $C_{4-7}$cycloalkyl($C_{1-4}$)alkyl, camphor-10-yl, or $C_{6-10}$aryl substituted by one or more ($C_{1-6}$)alkyl, ($C_{2-6}$)alkenyl, $C_{6-10}$aryl, $C_{6-10}$ar($C_{1-6}$)alkyl, $C_{6-10}$ aryloxy (further optionally substituted by nitro, halo, or cyano), $C_{6-10}$ aryldiazenyl (further optionally substituted by amino, $C_{1-4}$alkylamino or di ($C_{1-4}$)alkylamino), $C_{1-6}$ alkoxy, halo($C_{1-6}$)alkyl, halo($C_{1-6}$)alkoxy, $C_{1-6}$ alkylcarbonylamino, $C_{1-6}$alkylsulfonyl, mono- or di-($C_{1-6}$)alkylamino, hydroxy, carboxy, cyano, nitro, halo, or a heteroaryl which is optionally substituted with one or more $C_{1-6}$alkyl, halo($C_{1-6}$)alkyl, or halo;

and when $R^1$ or $R^2$ is $R^{12}CO$, then $R^{12}$ can also be N-attached pyrrolidinyl, piperidinyl or morpholinyl.

Preferred values of $R^1$ include hydrogen and methyl.

Preferred values of $R^2$ include hydrogen, t-butylcarbonyl, butylsulfonyl, propylsulfonyl, benzylsulfonyl, pentylsulfonyl, 4-tolylsulfonyl, and camphor-10-sulfonyl.

Especially preferred compounds are those of Formula IV wherein:

$R^1$ is hydrogen; and $R^2$ is $R^{12}SO_2$, where $R^{12}$ is hydrogen, $C_{1-6}$alkyl, $C_{4-7}$cycloalkyl, camphor-10-yl, ($C_{2-6}$)alkenyl, ($C_{2-6}$) alkynyl, thienyl, thiazolyl, benzo[b]thiophenyl, pyrazolyl, chromanyl, imidazolyl, benzo[2,3-c]1,2,5-oxadiazole, $C_{6-10}$aryl, $C_{6-10}$ar($C_{1-6}$)alkyl, or $C_{6-10}$ ar($C_{2-6}$alkenyl, any of which can be optionally substituted by one or more $C_{1-6}$alkyl, $C_{2-6}$alkenyl, $C_{6-10}$aryl, $C_{6-10}$aryloxy (further optionally substituted by nitro, halo, or cyano), $C_{6-10}$ar($C_{6-10}$)alkyl, 4-dimethylaminophenyldiazenyl, $C_{1-6}$alkoxy, halo ($C_{1-6}$) alkyl, halo($C_{1-6}$)alkoxy, $C_{1-6}$ alkylcarbonylamino, $C_{1-6}$alkylsulfonyl, mono- or di-($C_{1-6}$)alkylamino, hydroxy, carboxy, cyano, nitro, halo, or pyrazolyl which is optionally substituted with one or more $C_{1-6}$alkyl, halo($C_{1-6}$)alkyl, or halo.

Suitable values of $R^{12}$ include methyl, butyl, chloropropyl, phenyl, benzyl, methylphenyl, ethylphenyl, propylphenyl, butylphenyl, tert-butylphenyl, pentylphenyl, phenylphenyl, camphoryl, nitrophenyl, nitrophenylmethyl, cyanophenyl, chlorophenyl, fluorophenyl, bromophenyl, trifluoromethylphenyl, trifluoromethoxyphenyl, acetylaminophenyl, butoxyphenyl, biphenyl, vinylphenyl, methoxyphenyl, methylsulfonylphenyl, 4-(3-chloro-2-cyanophenoxy)phenyl, 4-(1,1-dimethylpropyl)phenyl, 6-chloro-2-methylphenyl, 2-methyl-5-nitrophenyl, 2,3,4-trichlorophenyl, 4-bromo-2,5-difluorophenyl, 5-bromo-2-methoxyphenyl, 2-chloro-5-(trifluoromethyl)-phenyl, 4-(2-chloro-6-nitrophenoxy, 4-bromo-2-(trifluoromethoxy)-phenyl, 3-chloro-2-cyanophenyl, 3-chloro-2-methylphenyl, 2-methyl-5-nitrophenyl, 4-methyl-3-nitrophenyl, 2,5-bis(2,2,2-trifluoroethoxy)phenyl, 2-chloro-4-(trifluoromethyl) phenyl, 4-chloro-2,5-dimethylphenyl, 5-chloro-2-methoxyphenyl, 4,6-dichloro-2-methylphenyl, 4-bromo-2-methylphenyl, 4-bromo-2-ethylphenyl, 2,4,6-trimethylphenyl, 2,3,4,5,6-pentamethylphenyl, 3,5-dichloro-2-hydroxyphenyl, 2,5-dimethoxyphenyl, 3,4-dimethoxyphenyl, 2,5-dimethylphenyl, 2-chloro4-(trifluoromethyl)phenyl, 3,5-dichlorophenyl, 2,6dichlorophenyl, 2,3-dichlorophenyl, 2,5-dichlorophenyl, 3,4-dichlorophenyl, 2,4-dichlorophenyl, 3,4dibromophenyl, 2,6-difluorophenyl, 3,4-difluorophenyl, 2,4,5-trichlorophenyl, 2,4,6-trichlorophenyl, 2,4,6-tris (methylethyl)phenyl, 4-bromo-2-ethylphenyl, 4-chloro-3-nitrophenyl, 2-methoxy-5-methylphenyl, 5-fluoro-2-methylphenyl, 4-methoxy-2,3,6-trimethylphenyl, 3-chloro-4-methylphenyl, 1-methylimidazol-4-yl,carboxyphenyl, naphthyl, 2,2,5,7,8-pentamethyl-chroma6-yl, thienyl, 5-chloro-2-thienyl, 3-bromo-5-chloro-2-thienyl, 4-bromo-2,5-dichloro-3-thienyl, 4,5-dibromo-2-thienyl, 4-bromo-5-chloro-2-thienyl, 5-bromo-2-thienyl, 2,5-dichloro-3-thienyl, 2-(acetylamino)-4-methyl-1,3-thiazol-5-yl, 5-chloro-1,3-dimethylpyrazol-4-yl, 5-[1-methyl-5-(trifluoromethyl)-pyrazol-3-yl]-2-thienyl, 5-chloro-3-methylbenzo[b] thiophen-2-yl, 5-chloro-1,3-dimethylpyrazol-4-yl, 4-[4-(dimethylaminophenyl)diazenyl]phenyl, 4-[3-(amidinoaminooxy)propoxy]phenyl, benzo[2,3-c]1,2,5-oxadiazol-4-yl, and 2-phenylvinyl.

Preferred $R^3$ groups include hydrogen, $C_{1-6}$alkyl and benzyl.

Preferred values of $R^4$ include hydrogen, $C_{1-6}$alkyl, $C_{6-10}$ar($C_{1-6}$)alkyl, $C_{1-6}$aryl, $C_{2-10}$hydroxyalkyl, $C_{2-10}$aminoalkyl, $C_{2-7}$carboxyalkyl, mono($C_{1-4}$alkyl)amino ($C_{1-8}$)alkyl, and di($C_{1-4}$alkyl)amino($C_{1-8}$)alkyl. Suitable values of $R^4$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino) ethyl.

Preferred compounds are those of Formula IV in which $R^5$, $R^6$ and $R^7$ are independently hydrogen, $C_{1-6}$alkyl, $C_{6-10}$ar($C_{1-6}$)alkyl, $C_{1-6}$aryl, $C_{2-10}$hydroxyalkyl or $C_{2-7}$carboxyalkyl. Useful values of $R^5$, $R^6$, and $R^7$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. In the most preferred embodiments, $R^5$, $R^6$ and $R^7$ are each hydrogen.

Preferred values of $R^8$ include hydrogen or $C_{1-6}$alkyl.

Preferred values of $R^9$, $R^{10}$ and $R^{11}$ in Formula IV include hydrogen, hydroxy, $C_{1-6}$alkyl, $C_{1-6}$alkoxy, cyano or —$CO_2R^w$, where $R^w$, in each instance, is preferably one of $C_{1-4}$alkyl, $C_{4-7}$cycloalkyl, phenyl, or benzyl. Suitable values of $R^9$, $R^{10}$ and $R^{11}$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^9$, $R^{10}$ and $R^{11}$ are each hydrogen.

Preferred values of m in Formula IV include zero to 6, more preferably zero to 4, and most preferably zero, 1, or 2.

Preferred values of m include zero to 4, and most preferably zero, 1, or 2.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

When any variable occurs more than one time in any constituent or in Formula IV, its definition on each occurrence is independent of its definition at every other occurrence. Also, combinations of substituents and/or variables are permissible only if such combinations result in stable compounds.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aryloxy" as employed herein by itself or as part of another group refers to monocyclic or bicyclic aromatic groups containing from 6 to 12 carbons in the ring portion, preferably 6–10 carbons in the ring portion, bonded to an oxygen atom. Examples include, but are not limited to, phenoxy, naphthoxy, and the like.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "heterocycle" as used herein, except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, chromanyl, benzimidazolyl, thiadiazoyl, benzopyranyl, benzothiazolyl, benzo[b]thiophenyl, benzo[2,3-c]1,2,5-oxadiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "haloalkoxy" as used herein refers to any of the above haloalkyl groups bonded to an oxygen atom, such as trifluromethoxy, trichloromethoxy, and the like.

Another aspect of the present invention is a process for preparing a tyrosine alkoxyguanidine compound of Formula IV, comprising reacting a compound of Formula V:

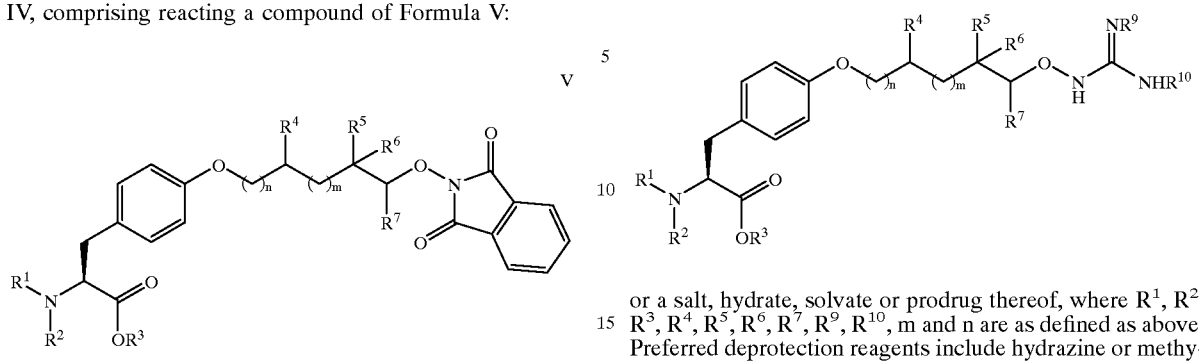

or a salt, hydrate, solvate or prodrug thereof, wherein $R^1$, $R^2$, $R^3$, $R^4$, $R^5$, $R^6$, $R^7$, m and n are as defined above, with a deprotection reagent and a guanidinylating reagent, to form a compound of Formula VI:

or a salt, hydrate, solvate or prodrug thereof, where $R^1$, $R^2$, $R^3$, $R^4$, $R^5$, $R^6$, $R^7$, $R^9$, $R^{10}$, m and n are as defined as above. Preferred deprotection reagents include hydrazine or methylamine. Preferred guanidinylating reagents include aminoiminosulfonic acid, 1H-pyrazole-1-carboxamidine hydrochloride, N,N'-bis(tert-butoxycarbonyl)-S-methylisothiourea, or N-$R^9$, N-$R^{10}$-1H-pyrazole-1-carboxamidine, where $R^9$ and $R^{10}$ are defined as above.

The compounds of the present invention may be prepared by the general procedures outlined in Schemes I, II, and III (below), where $R^1$, $R^2$, $R^3$, $R^4$, $R^5$, $R^6$, $R^7$, $R^8$, $R^9$, $R^{10}$, $R^{11}$, $R^{12}$, $R^w$, n, and m are as defined above.

SCHEME I

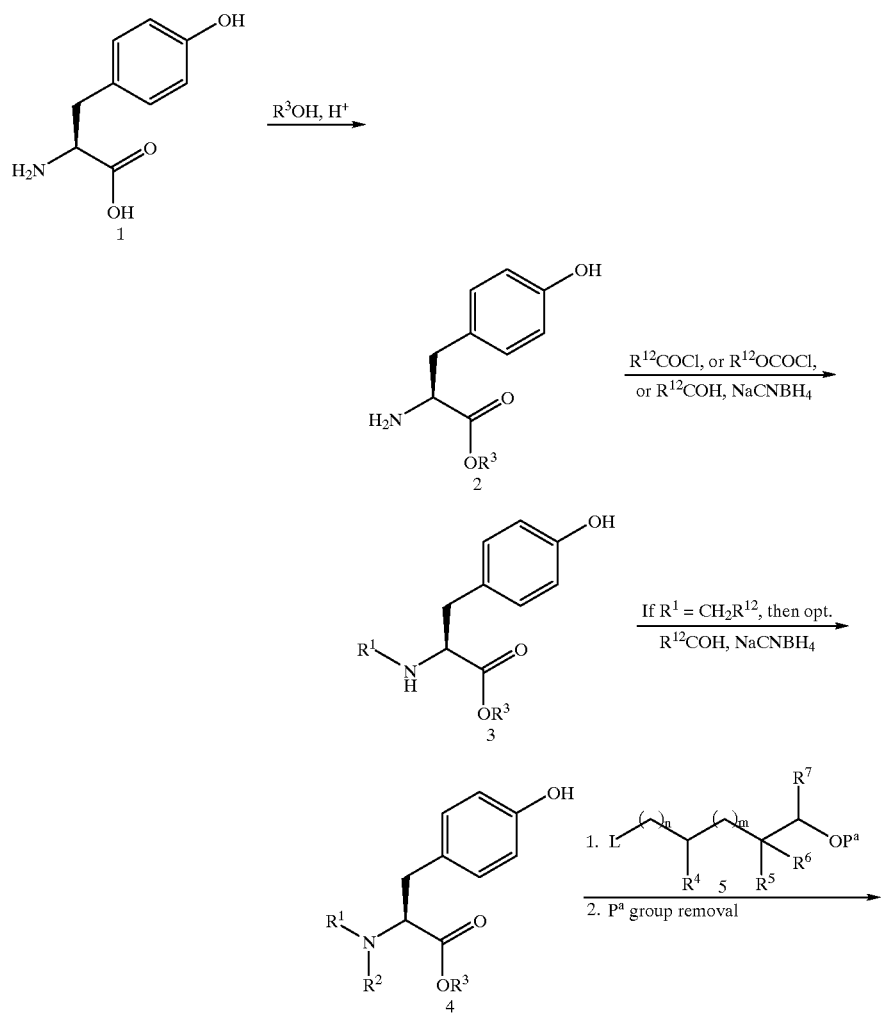

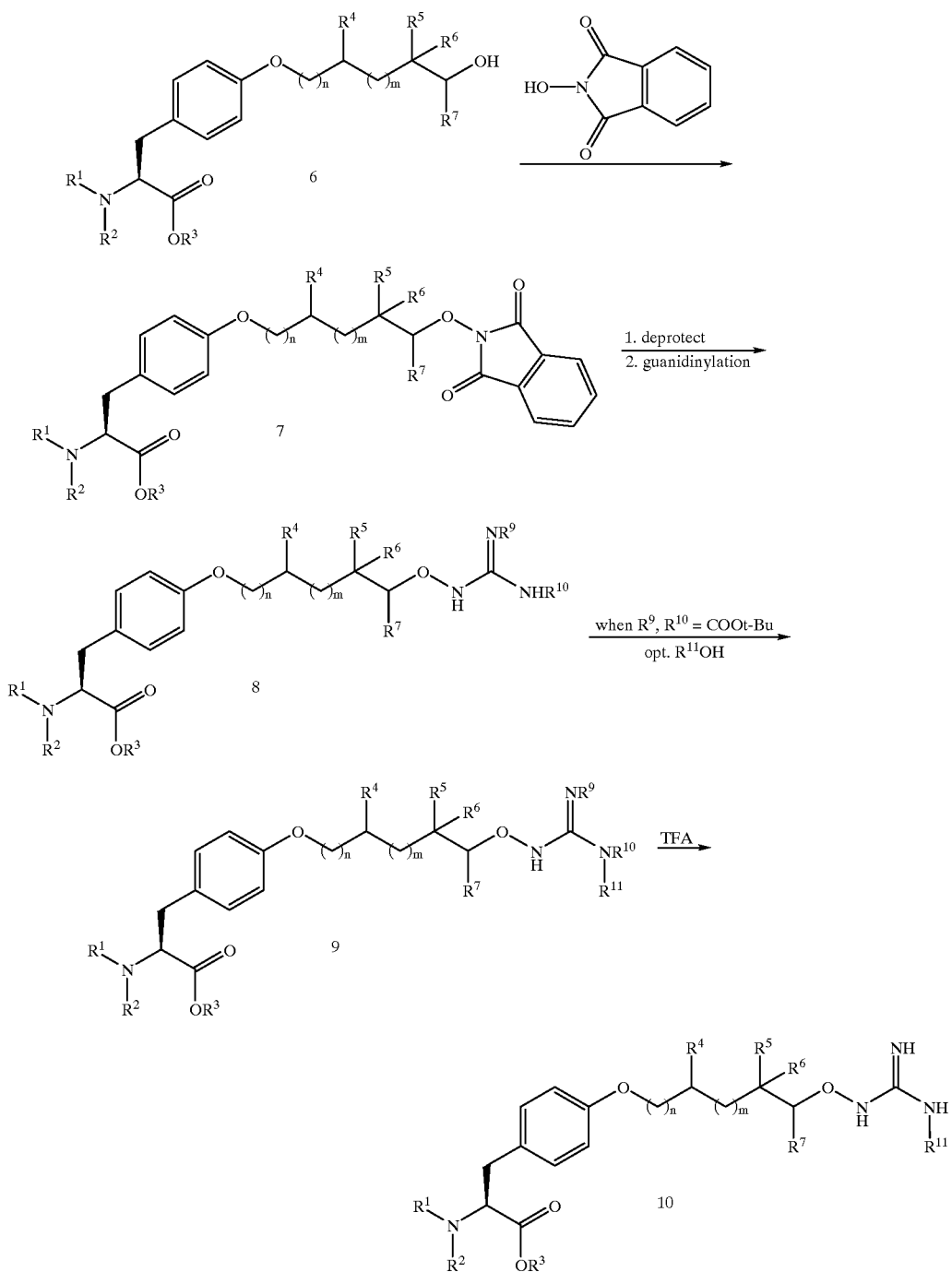

SCHEME II
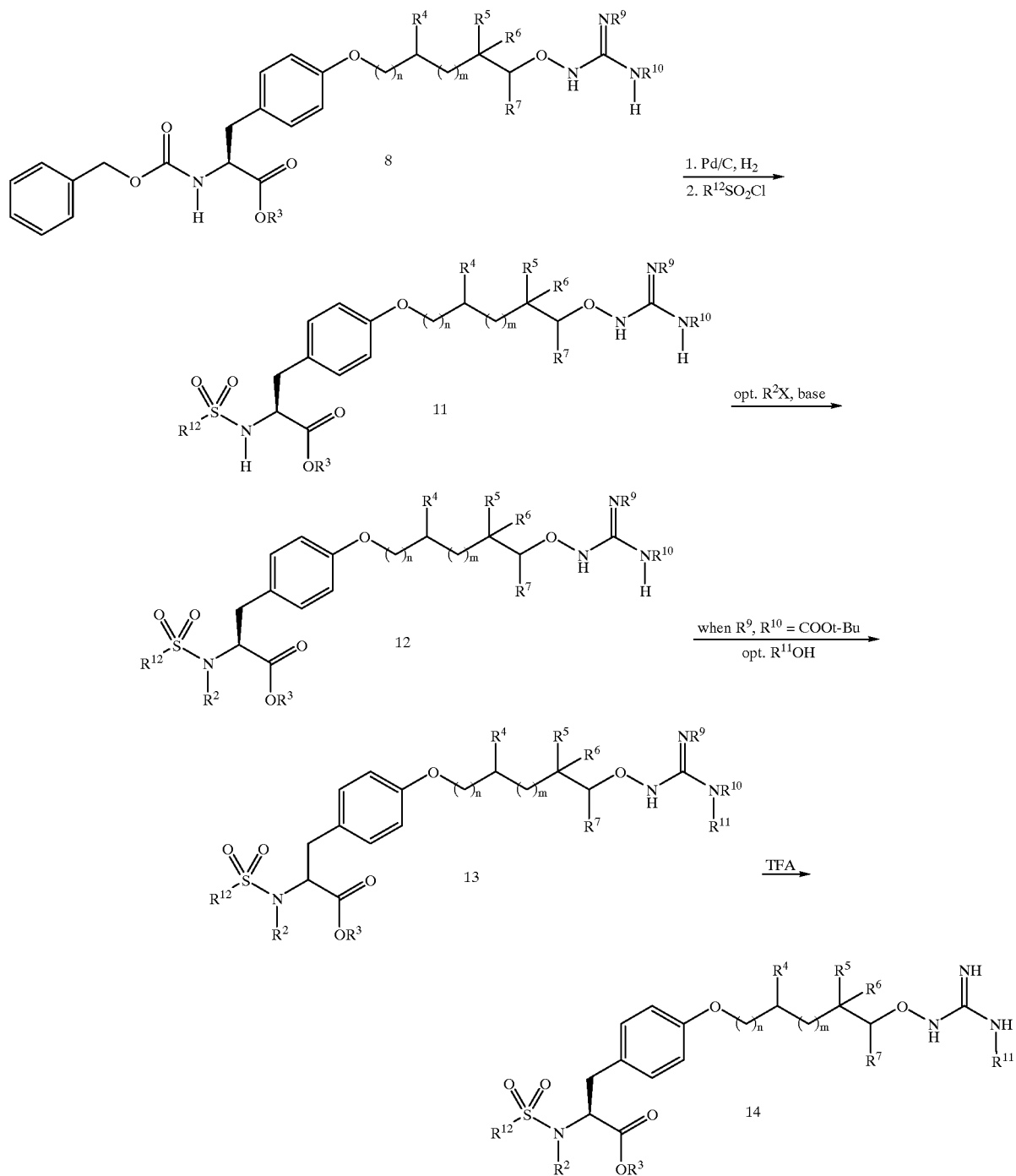

SCHEME III
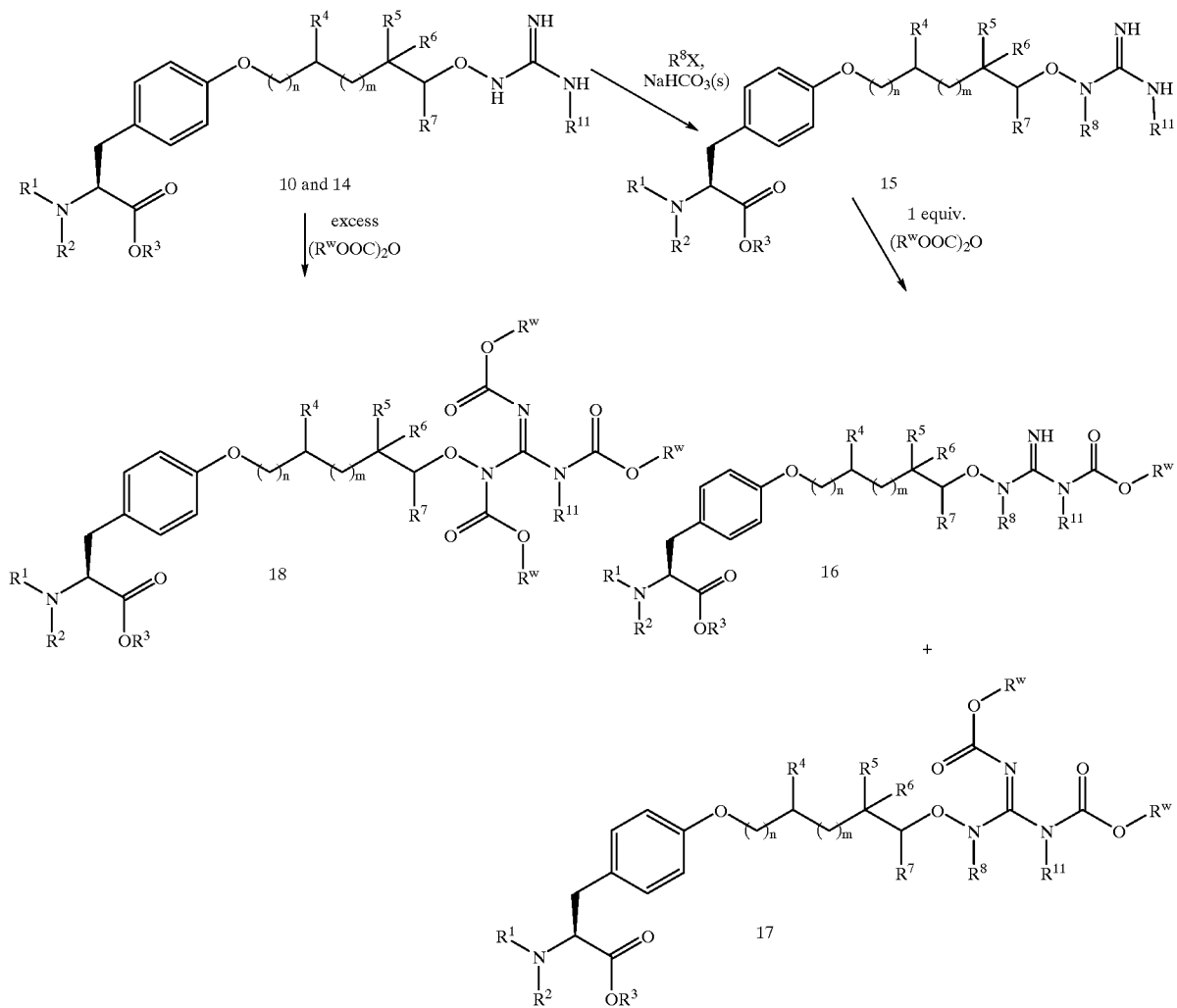
SCHEME IV
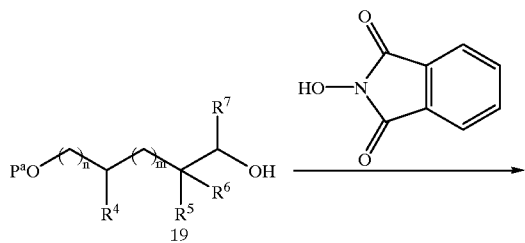

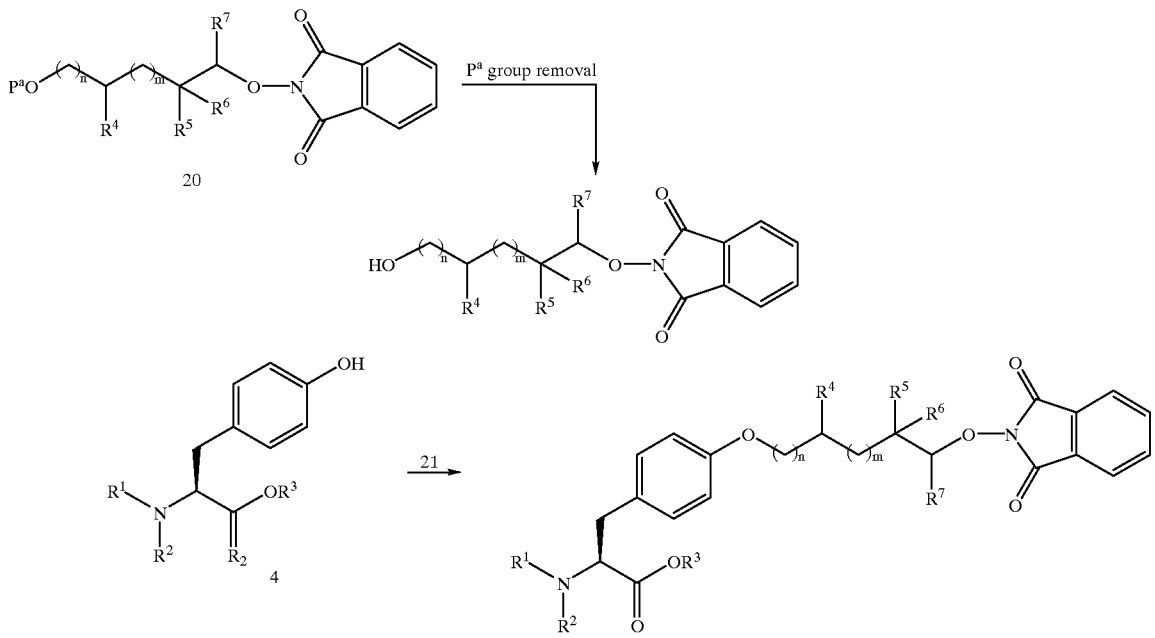

Scheme I outlines the synthetic steps to produce compounds of the present invention where $R^1$ is $R^{12}OOC$— or $R^{12}CO$— or $R^{12}CH_2$—. The carboxyl group of the tyrosine 1 is protected as an ester by methods well known in the art (Bodanszky, M. and Bodanszky, A., *The Practice of Peptide Synthesis*, Springer-Verlag, Berlin (1984)). The amine 2 is reacted with acyl chlorides ($R^{12}COCl$) in the presence of a suitable base such as a tertiary amine to produce carboxamides 3 ($R^1=R^{12}CO$). Alternatively, the carboxamides 3 may be produced by the reaction of 2 with carboxylic acids ($R^{12}COOH$) by any of the known peptide coupling reagents, such as 1,3-dicyclohexylcarbodiimide or Castro's reagent (BOP) (Castro, B., et al., *Tetrahedron Lett.* 1219 (1975)). Still alternatively, the amines 2 can be converted to carbamates 3 ($R^1=R^{12}OOC$) by reaction with chloroformates ($R^{12}OCOCl$) in the presence of a base, such as a tertiary amine. Still alternatively, reductive amination of 2 can be achieved by reaction with an aldehyde ($R^{12}COH$) under reducing conditions. The preferred reducing agent is tetramethylammonium triacetoxyborohydride. Alternatively, sodium triacetoxyborohydride or sodium cyanoborohydride may be used. Still alternatively, reductive amination may be carried out by forming an imine (Schiff base) between the amine and the carbonyl component using a catalytic amount of acid such as p-toluenesulfonic acid, followed by reduction with sodium cyanoborohydride. The alkylated amines 3 ($R^1=R^{12}CH_2$—) can be further converted to dialkylated amines 4 by a repetition of the reductive amination step above to produce $R^2=R^{12}CH_2$—. Still alternatively, the imine may be reduced using catalytic hydrogenation using a catalyst such as palladium on carbon in a standard solvent such as ethanol. As an alternative to reduction methods, the amine 2 may be reacted with $R^{12}CH_2L$, where L is a reactive leaving group, such as a halide or sulfonate.

The phenolic functionality of 4 is coupled to 5, where L is a reactive leaving group such as halide or sulfonate, under basic conditions, such as cesium carbonate in a solvent such as N,N-diethylformamide. The alcohol functionality may be protected with $p^a$, an orthogonally selective functionality to the ester functionality (i.e., benzyl ethers would not be used with a benzyl ester). Removal of the optional alcohol protecting group $p^a$ is routinely accomplished using the reaction conditions well known in the art. For example, deprotection of benzyl ethers maybe effected through catalytic hydrogenation using palladium on carbon as a catalyst in solvents such as ethanol or tetrahydrofuran. Deprotection of an acetate protecting group is accomplished by basic hydrolysis, most preferably with sodium hydroxide in aqueous tetrahydrofuran. Alternatively, the phenolic functionality of 4 may be coupled to 5 (for L=OH) using a Mitsunobu coupling procedure (Mitsunobu, O., *Synthesis* 1 (1981)), where $p^a$ may be a suitable alcohol protecting group. Alternatively, suitable diols ($P^a=H$) may be used in the Mitsunobu reaction. Preferred coupling conditions include using a trialkylphosphine or triarylphosphine, such as tri-n-butylphosphine or triphenylphosphine, in a suitable solvent, such as tetrahydrofuran or dichloromethane, and an azodicarbonyl reagent, such as diethyl azodicarboxylate or 1,1'-(azodicarbonyl)dipiperidine.

Alcohol 6 is converted to 7 employing a Mitsunobu reaction with an N-hydroxycyclic imide derivative such as N-hydroxyphthalimide. Unveiling of the phthalimide protecting group of 7 is accomplished using standard conditions well known in the art (Greene, T. W. and Wuts, P. G. M., *Protective Groups in Organic Synthesis*, 2nd edition, John Wiley and Sons, Inc. New York (1991)), for example using hydrazine or methylamine. Alternatively, sodium borohydride in a mixture of an appropriate alcohol (e.g., ethanol/water) followed by acidification.

Guanidinylation of the resulting alkoxyamine to 8 is achieved using standard reagents such as aminoiminosulfonic acid (Miller, A. E. and Bischoff, J. J. *Synthesis* 777 (1986)), or 1H-pyrazole-1-carboxamidine hydrochloride (Bernatowicz, M. S. et al., *J. Org. Chem.* 57 (8), 2497 (1992)), or with substituted guanidinylating reagents such as N,N'-bis(tert-butoxycarbonyl)-S-methylisothiourea (Bergeron, R. J. and McManis, J. S., *J. Org. Chem.* 52:1700 (1987)) or N-$R^9$, N-$R^{10}$-1H-pyrazole-1-carboxamidine, where $R^9$ and $R^{10}$) are defined as above for Formula IV. When $R^9$ and $R^{10}$ are protecting groups, for example t-butyloxycarbonyl (Boc), the compound can be optionally reacted with $R^{11}OH$ using standard Mitsunobu reaction condition as reviewed above to produce alkylated compounds 9. These protecting groups can be optionally removed by treatment with acid, usually trifluoroacetic acid in a suitable solvent such as dichloromethane or water, or by HCl gas dissolved in a suitable solvent, such as 1,4-dioxane to produce targeted compounds 10.

Scheme II outlines the synthetic steps to produce compounds of the present invention where $R^1$ of Formula IV is $R^{12}SO_2$—. Thus, compound 8, where $R^1$ is N-benzyloxycarbonyl (Cbz) is removed by catalytic hydrogenation using a catalyst such as palladium on carbon and hydrogen to reveal the amino functionality, which is subsequently sulfonylated with sulfonyl chlorides ($R^{12}SO_2Cl$) or sulfoanhydrides ($R^{12}SO^2)^2O$ to produce sulfonamides 11. The acidic nature of the sulfonamide nitrogen allows alkylations to occur under basic conditions. Thus, reaction with a base such as potassium carbonate and $R^2X$, where X is a reactive leaving group such as a halide or sulfonate in a suitable solvent such as acetonitrile provides alkylated sulfonamides 12. When $R^9$ and $R^{10}$ are protecting groups, for example t-butyloxycarbonyl (Boc), the compound can be optionally reacted with $R^{11}OH$ using standard Mitsunobu reaction condition as reviewed above to produce alkylated compounds 13. These protecting groups can be optionally removed by treatment with acid, usually trifluoroacetic acid in a suitable solvent such as dichloromethane or water, or by HCl gas dissolved in a suitable solvent, such as 1,4-dioxane to produce targeted compounds 14.

Further functionalization of the amidinoaminooxy group in 10 and 14 (where $R^1$ is $R^{12}SO_2$) is described in Scheme III. The aminooxy nitrogen of 10 and 14 may be optionally alkylated using basic conditions such as solid sodium bicarbonate in a suitable solvent such as N,N-dimethylformamide with $R^8X$, where X is a reactive leaving group such as a halide or sulfonate to give 15. Additionally, 15 may be reacted with pyrocarbonates such as diethyl pyrocarbonate in a suitable solvent such as acetonitrile or N,N-dimethylformamide in the presence of a tertiary amine base such as N,N-diisopropylethylamine to give carbamates of either mono- or di- substitution on the amidino nitrogens as in 16 and 17 as well as tri-carbamates with additional substitution on the aminooxy nitrogen as in 18.

Scheme IV outlines an alternative synthesis of the target component 7 in Scheme I. In this alternative synthesis, the alcohol 19 is reacted with N-hydroxyphthalimide in a Mitsunobu reaction to yield 20. After the removal of the protecting group Pa, the key intermediate 21 and the phenol 4 are coupled in another Mitsunobu reaction to yield the intermediate 7.

The present invention a method of treating αvβ3 integrin- or αvβ5 integrin-mediated conditions by selectively inhibiting or antagonizing αvβ3 and αvβ5 cell surface receptors, which method comprises administering a therapeutically effective amount of a compound selected from the class of compounds depicted by FormulaIV, wherein one or more compounds of Formula IV is administered in association with one or more non-toxic, pharmaceutically acceptable carriers and/or diluents and/or adjuvants and if desired other active ingredients.

More specifically, the present invention provides a method for inhibition of the αvβ3 cell surface receptor. Most preferably, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, age-related macular degeneration, retinopathy of prematurity and other neo-vascular eye diseases, inhibiting arthritis, psoriasis and periodontal disease, and inhibiting smooth muscle cell migration including neointimal hyperplasia and restenosis.

The present invention also provides a method for inhibition of the αvβ5 cell surface receptor. Most preferably, the present invention provides a method for inhibiting angiogenesis associated with pathological conditions such as inflammatory disorders such as immune and non-immune inflammation, chronic articular rheumatism and psoriasis, disorders associated with inappropriate or inopportune invasion of vessels such as restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and similar cancers which require neovascularization to support tumor growth. The present invention also provides a method for treating eye diseases characterized by angiogenesis, such as diabetic retinopathy, age-related macular degeneration, presumed ocular histoplasmosis, retinopathy of prematurity, and neovascular glaucoma.

The compounds of the present invention are useful in treating cancer, including tumor growth, metastasis and angiogenesis. For example, compounds of the present invention can be employed to treat breast cancer and prostate cancer.

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes.

Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred alkaline salts are ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the ail can select using conventional criteria. The vehicles may be selected from the known ophthalmic vehicles which include but are not limited to water, polyethers such s polyethylene glycol 400, polyvinyls such as polyvinyl alcohol, povidone, cellulose derivatives such as carboxymethylcellulose, methylcellulose and hydroxypropyl methylcellulose, petroleumn derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the compounds of the present invention in the composition include alcohols such as chlorobutanol, benzalknonium chloride and EDTA, or any other appropriate preservative known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

(2S)-3-{4-[3-(amidinoaminooxy)propoxy]phenyl}-2-[(butylsulfonyl)amino]propanoic acid trifluoroacetic acid

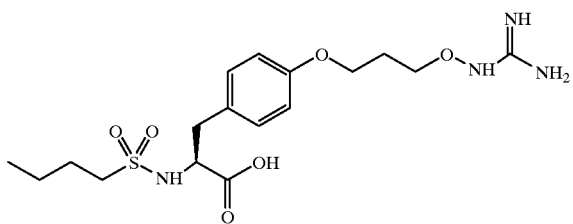

1. tert-butyl (2S)-3-[4-(3-hydroxypropoxy)phenyl]-2-[(phenylmethoxy)carbonylamino]propanoate

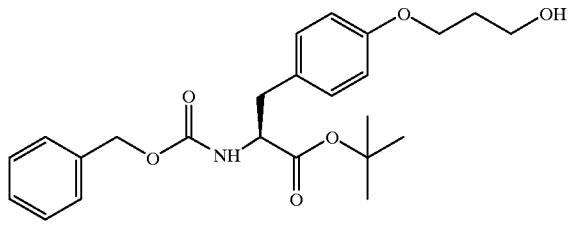

A mixture of N-(benzyloxycarbonyl)-L-tyrosine tert-butyl ester (0.37 g, 1.0 mmol), 3-bromo-1-propanol (0.09 mL, 1.0 mmol), and cesium carbonate (0.33 g, 1.0 mmol) in anhydrous N,N-dimethylformamide (5 mL) was stirred at room temperature for 24 h. The reaction mixture was evaporated to dryness under high vacuum and the residue was partitioned between water and ethyl acetate. The aqueous layer was separated and extracted with ethyl acetate. The ethyl acetate extracts were combined and washed once with saturated sodium bicarbonate and brine. The ethyl acetate was dried and evaporated to dryness. The residue was purified on a silica gel column (10 g Waters Sep-Pak) by eluting with a gradient of ethyl acetate and hexane from 20:80 to 30:70. The pure fractions were combined and evaporated to dryness to give the title compound (0.269 g, 63% yield) as a clear oil. $^1$H NMR (300 MHz, CDCl$_3$) δ7.34 (m, 5H), 7.05 (d, J=8.6 Hz, 2H), 6.80 (m, 2H), 5.22 (d, J=8.1 Hz, 1H), 5.10 (d, J=2.8 Hz, 2H), 4.48 (q, J=8.1 Hz, 1H), 4.09 (t, J=6.0 Hz, 2H), 3.86 (t, J=6.0 Hz, 2H), 3.02 (m, 2H), 2.03 (p, J=6.0 Hz, 2H), 1.41 (s, 9H).

2. tert-butyl (2S)-3-{4-[3-(1,3-dioxoisoindolin-2-yloxy)propoxy]phenyl}-2-[(phenylmethoxy)carbonylamino]propanoate

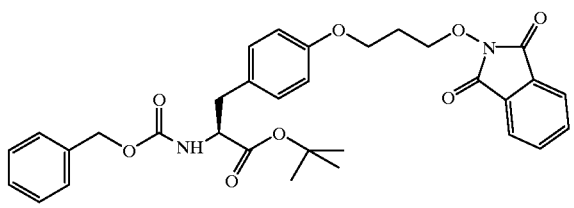

A mixture of tert-butyl (2S)-3-[4-(3-hydroxypropoxy)phenyl]-2-[(phenylmethoxy)carbonylamino]propanoate (0.215 g, 0.5 mmol), as prepared in the preceding step, N-hydroxyphthalimide ((0.098 g, 0.6 mmol), and triphenylphosphine (0.157 g, 0.6 mmol) in anhydrous tetrahydrofuran (10 mL) was treated with diethyl azodicarboxylate (0.095 g, 0.6 mmol). The reaction mixture was allowed to stir at room temperature overnight. The reaction mixture was evaporated to dryness and the residue was placed on a silica gel column (10 g Waters Sep-Pak) and eluted with 20% ethyl acetate and 80% hexane. The pure fractions were combined and evaporated to give the title compound (0.280 g, 97% yield). $^1$H NMR (300 MHz, CDCl$_3$) δ7.84 (dd, J=5.6,3.0 Hz, 2H), 7.75 (dd, J=5.6, 3.0 Hz, 2H), 7.28–7.34 (m, 5H), 7.03 (d, J=8.7 Hz, 2H), 6.83 (d, J=8.7 Hz, 2H), 5.22 (br d, J=8.2 Hz, 1H), 5.09 (d, J=2.5 Hz, 2H), 4.48 (m, 1 H), 4.41 (t, J=6.3 Hz, 2H), 4.20 (t, J=6.2 Hz, 2H), 3.01 (br d, J=5.9 Hz, 2H), 2.23 (p, J=6.2 Hz, 2H), 1.41 (s, 9H).

3. tert-butyl (2S)-3-{4-[3-(aminooxy)propoxy]phenyl}-2-[(phenylmethoxy)carbonylamino]propanoate

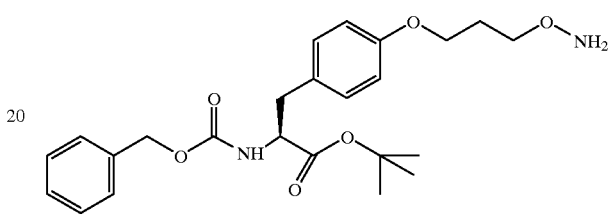

A mixture of tert-butyl (2S)-3-{4-[3-(1,3-dioxoisoindolin-2-yloxy)propoxy]phenyl}-2-[(phenylmethoxy[]carbonylamino]propanoate (0.287 g, 0.5 mmol), as prepared in the preceding step, and 40% aqueous N-methylamine (0.1 86 mL) in tetrahydrofuran (5 mL) was stirred overnight at room temperature. The reaction mixture was evaporated to dryness and the residue was treated with ethyl acetate. The mixture was filtered and the filtrate was evaporated to dryness. The residue was purified on a silica gel column (2 g Waters Sep-Pak) using a gradient of ethylacetate and hexane from 50:50 to 100:0 to give the title compound (126 mg, 57% yield). $^1$H NMR (300 MHz, CDCl$_3$) δ7.34 (m, 5H), 7.04 (m, 2H), 6.79 (m, 2H), 5.20 (m, 1 H), 5.09 (d, J=2.8 Hz, 2H), 4.48 (m, 5H), 4.00 (t, J=6.2 Hz, 2H), 3.84 (t, J=6.2 Hz, 2H), 3.01 (br d, J=5.3 Hz, 2H), 2.06 (p, J=6.2 Hz, 2H), 1.41 (s, 9H).

4. tert-butyl 3-{[3-(4-{(2S)-2-[(tert-butyl)oxycarbonyl]-2-[(phenylmethoxy)carbonylamino]ethyl}phenoxy)propoxy]amino}-2-aza-3-[(tert-butoxy)carbonylamino]prop-2-enoate

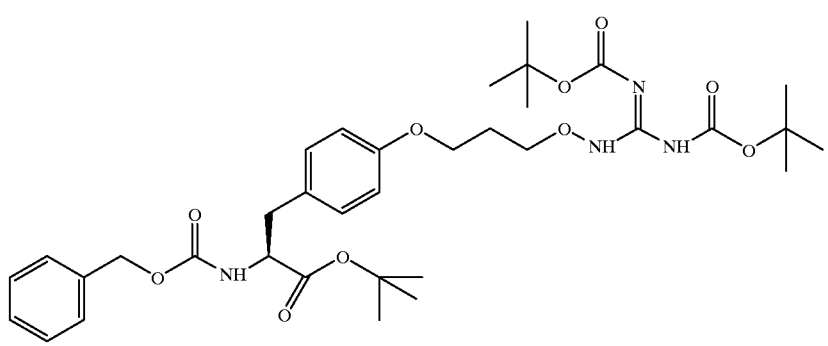

A mixture of tert-butyl (2S)-3-{4-[3-(aminooxy)propoxy]phenyl}-2-[(phenylmethoxy)carbonylamino]propanoate (0.126 g, 0.284 mmol), as prepared in the preceding step, in anhydrous N,N-dimethylformamide (8 mL) was reacted with (N,N'-di-butoxycarbonyl)amidinopyrazole (0.097 g, 0.313 mmol). The reaction mixture was allowed to stir at room temperature over the weekend. The reaction mixture was evaporated under high vacuum and the residue was placed under high vacuum overnight. The residue was purified on a silica gel column (5 g Waters Sep-Pak) using 20% ethylacetate and 80% hexane. The desired product (0.091 g, 47% yield) was obtained. $^1$H NMR (300 MHz, CDCl$_3$) δ9.08 (s, 1H), 7.74 (br s, 1H), 7.34 (m, 5H), 7.03 (d, J=8.6 Hz, 2H), 6.80 (d, J=8.6 Hz, 2H), 5.21 (m, 1H), 5.09 (d, J=2.2 Hz, 2H), 4.48 (m, 1 H), 4.23 (t, J=6.2 Hz, 2H), 4.03 (t, J=6.2 Hz, 2H), 3.01 (br d, J=5.7 Hz, 2H), 2.16 (p, J=6.2 Hz, 2H), 1.49 (s, 18H), 1.41 (s, 9H).

5. tert-butyl 3-{[3-(4-{(2S)-2-amino-2-[(tert-butyl)oxycarbonyl]ethyl}phenoxy)propoxy]amino}-2-aza-3-[(tert-butoxy)carbonylamino]prop-2-enoate

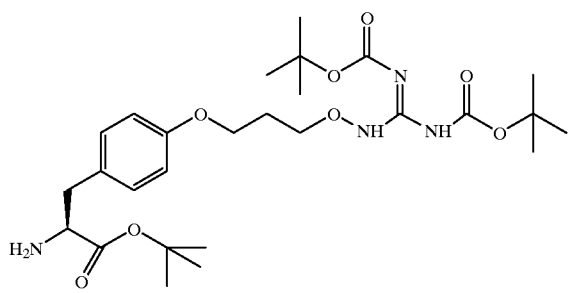

A suspension of tert-butyl 3-{[3-(4-{(2S)-2-[(tert-butyl)oxycarbonyl]-2-[(phenylmethoxy)carbonylamino]ethyl}phenoxy)propoxy]amino}-2-aza-3-[(tert-butoxy)carbonylamino]prop-2-enoate (0.091 g, 0.133 mmol), as prepared in the preceding step, and 10% Pd/C (0.014 g) in methanol (10 mL) and chloroform (1 mL) was treated with hydrogen via balloon for 2 h. The mixture was filtered through a bed of Celite and the filtrate was evaporated to give the desired product (0.063 g, 86% yield). $^1$H NMR (300 MHz, CDCl) δ9.07 (s, 1H), 7.73 (br s, 1H), 7.20 (d, J=8.3 Hz, 2H), 6.85 (d, J=8.3 Hz, 2H), 4.23 (t, J=6.2 Hz, 2H), 4.11 (m, 1 H), 4.03 (t, J=6.2 Hz, 21, 3.25 (br s, 2H), 2.15 (p, J=6.2 Hz, 2H), 1.48 (s, 18H), 1.43 (s, 9H).

6. tert-butyl 3-{[3-(4-{(2S)-2-[(tert-butyl)oxycarbonyl]-2-[(butylsulfonyl)amino]ethyl}phenoxy)propoxy]amino}-2-aza-3-[(tert-butoxy)carbonylamino]prop-2-enoate A solution of tert-butyl 3-{[3-(4-{(2S)-2-amino-2-[(tert-butyl)oxycarbonyl]ethyl}phenoxy)propoxy]amino}-2-aza-3-[(tert-butoxy)carbonylamino]prop-2-enoate (0.063 g, 0.133 mmol), as prepared in the preceding step, in methylene chloride (10 mL) was treated with 1-butane sulfonylchloride (0.04 mL, 0.31 mmol, 2.2 equivalents) and triethylamine (0.06 mL, 0.42 mmol, 3 equivalents). The reaction mixture was stirred at room temperature overnight. An additional aliquot of 1-butane sulfonylchloride (0.018 mL, 1 equivalent) and triethylamine (0.02 mL, 1 equivalent) was added and the reaction mixture was stirred for 3 h. The reaction mixture was evaporated to dryness and the residue was purified on a silica gel column (10 g Waters SepPak) using 30% ethylacetate and 70% hexane to give the title compound (0.04 g, 43% yield). Mass spectrum (LCMS, ESI) calcd. for $C_{31}H_{52}N_4O_{10}S$: 695 (M+Na). Found: 695.1.

7. (2S)-3-{4-[3-(amidinoaminooxy)propoxy]phenyl}-2-[(butylsulfonyl)amino]propanoic acid trifluoroacetic acid salt

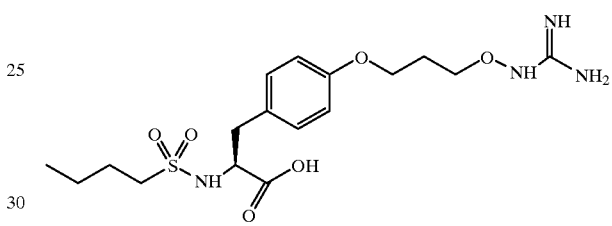

A solution of tert-butyl 3-{[3-(4{(2S)-2-[(tert-butyl)oxycarbonyl]-2-[(butylsulfonyl)amino]ethyl}phenoxy)propoxy] amino }-2-aza-3-[(tert-butoxy)carbonylamino]prop-2-enoate (0.04 g, 0.06 mmol), as prepared in the preceding step, in methylene chloride (0.5 mL) was cooled in an ice bath and treated with trifluoroacetic acid (0.5 mL). The reaction mixture was stirred at room temperature for 2 h. The reaction mixture was evaporated to dryness and the residue was dissolved in tetrahydrofuran and diluted with hexane to produce an oil (0.023 g, 92% yield) as the desired product. $^1$H NMR (300 MHz, CDCl$_3$) δ7.57 (d, J=9 Hz, 1 H), 7.41 (br s, 4H), 7.20 (d, J=8.6 Hz, 2H), 6.86 (d, J=8.6 Hz, 2H), 4.03 (t, J=6.2 Hz, 2H), 3.90 (m, 3H), 3.60 (m, 2H), 2.98 (dd, J=13.8, 4.6 Hz, 2H), 2.69 (dd, J=13.8, 10.1 Hz, 2H), 2.58 (t, J=7.6 Hz, 2H), 2.05 (p, J=6.3 Hz, 2H), 1.76 (m, 2H), 1.16 (m, 2H), 0.76 (t, J=7.2 Hz, 3H). Mass spectrum (MALDI-TOF, α-cyano-4-hydroxycinnamic acid matrix) calcd. for $C_{17}H_{28}N_4O_6S$: 417.2 (M+W). Found: 417.2.

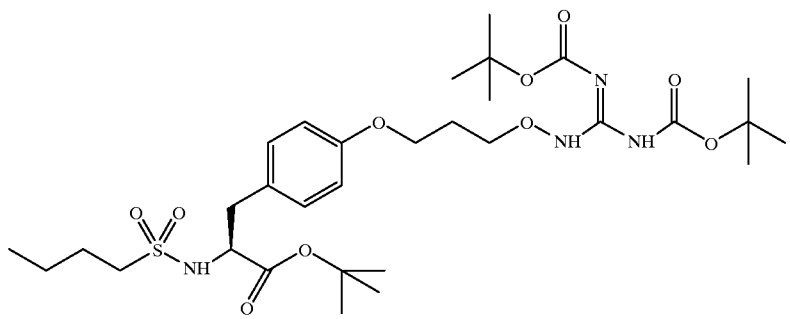

EXAMPLE 2

(2S)-3-{4-[3-(Amidinoaminooxy)propoxy]phenyl}-2-[(naphthylsulfonyl)amino]propanoic acid trifluoroacetic acid salt 1. 2-[3-Phenylmethoxy)propoxy]isoindoline-1,3-dione

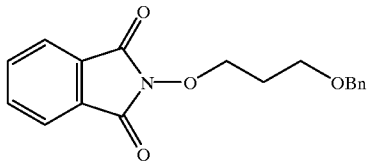

To a solution of 4.9 mL (31 mmol) of 3-benzyloxypropan-1-ol, 5 g (31 mmol) of N-hydroxyphthalimide, and 9.7 g (37 mmol) of triphenylphosphine in 180 mL THF at water/ice mixture temperature was added 5.8 mL (37 mmol) of DEAD dropwise over a 45-min period. The solution was stirred at the same temperature for additional 30 min. Then the solution was allowed to warm to room temperature and stirred overnight. Then the solvent was removed under reduced pressure. The mixture was chromatographed on a silica gel column using EtOAc/hexanes (1:9 to 2:3 v/v) as eluent to yield 8.2 g (86%) of viscous liquid as product: $^1$H NMR (300 MHz, CDCl$_3$) δ7.85–7.81 (m, 2H), 7.78–7.73 (m, 2H), 7.37–7.25 (m, 5H), 4.56 (s, 2H), 4.35 (t, J=6.34 Hz, 2H), 3.73 (t, J=6.11 Hz, 2H), 2.09 (quintet, J=6.23 Hz, 2H).

2. 2-(3-Hydroxypropoxy)isoindoline-1,3-dione

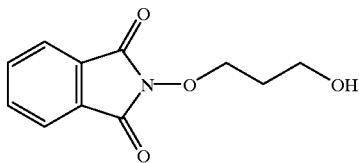

To a solution of 8.2 g (27 mmol) of 2-[3-(phenylmethoxy)propoxy]isoindoline-1,3-dione, as prepared in the preceding step, in 120 mL anhydrous ethanol under nitrogen was added 1.5 g of 10 wt % Pd/C. Then the nitrogen in the reaction was replaced with hydrogen and the reaction was stirred at room temperature for 5 h. After the reaction was completed, the mixture was filtered through a pad of Celite (diatomaceous earth). The solvent of the filtrate was removed under reduced pressure. The residue was chromatographed on a silica gel column using ethyl acetate/hexanes (1:1, v/v) as eluent to yield 4.4 g (75%) of white solid as product: $^1$H NMR (300 MHz, CDCl$_3$) δ7.85–7.81 (m, 2H), 7.78–7.74 (m, 2H), 4.37 (t, J=5.88 Hz, 2H), 3.93 (t, J=5.80 Hz, 2H), 2.55 (br s, 1H), 1.99 (quintet, J=5.86, 2H).

3. Methyl (2S)-3-(4-hydroxyphenyl)-2-[(phenylmethoxy)carbonyl amino]propanoate

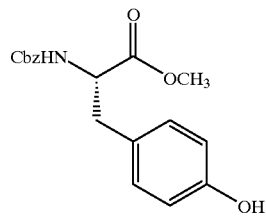

To a solution of 15.6 g (49 mmol) (2S)-3-(4-hydroxyphenyl)-2-[(phenylmethoxy)carbonylamino] propanoic acid in 120 mL methanol was added 9.4 g (49 mmol) of p-toluenesulfonic acid monohydrate. The solution was heated to 70 ° C. for 2 h. After solution was cooled to room temperature, the methanol was removed under reduced pressure. The solid obtained was redissolved in 120 mL methylene chloride. The organic solution was then washed with dilute NaHCO$_3$ solution twice and brine. The organic layer was dried with anhydrous MgSO$_4$ and filtered. The solvent was removed under reduced pressure. The crude mixture was chromatographed on a silica gel column using 40% ethyl acetate in hexanes as the eluent to yield 15.6 g (96%) of white solid as product: $^1$H NMR (300 MHz, CDCl$_3$) δ7.38–7.30 (m, 5H), 6.93 (d, J=8.41 Hz, 2H), 6.81 (d, J=8.41 Hz, 2H), 5.39 (br s, 1H), 5.24 (d, J=9.29 Hz, 1H), 5.11 (d, J=12.32 Hz, 1H), 5.06 (d, J=12.29 Hz, 1H), 4.61 (m, 1H), 3.71 (s, 3H), 3.06 (dd, J=5.88, 14.06 Hz, 1H), 2.98 (dd, J=5.88, 14.06 Hz, 1H)

4. Methyl(2S)-3-{4-[3-(1,3-dioxoisoindolin-2-yloxy)propoxy]phenyl}-2-[(phenylmethoxy)carbonylamino]propanoate

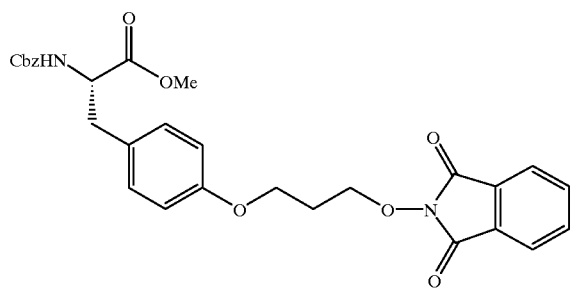

To a solution of 100 mg (0.30 mmol) of methyl (2S)-3-(4-hydroxyphenyl)-2-[(phenylmethoxy)carbonylamino]propanoate, as prepared in the preceding step, 67 mg (0.30 mmol) of 2-(3-hydroxypropoxy)isoindoline-1,3-dione, as prepared in step 2, and 88 mg (0.34 mmol) of triphenylphosphine in 10 mL THF at water/ice mixture temperature was added 66 mL (0.34 mmol) of DIAD dropwise. The solution was stirred at the same temperature for additional 20 min. Then the solution was allowed to warm to room temperature and stirred overnight. The solvent was removed under reduced pressure. The mixture was chromatographed on a silica gel column using EtOAc/hexanes (3:7 to 2:3 v/v) as eluent to yield 89 mg (55%) of viscous liquid as product: $^1$H NMR (300 MH, CDCl$_3$) δ7.85–7.80 (m, 2H), 7.77–7.71 (m, 2H), 7.38–7.27 (m, 5H), 6.98 (d, J=8.65 Hz, 2H), 6.82 (d, J=8.65 Hz, 2H), 5.19 (d, J=8.16 Hz, 1H), 5.09 (s, 2H), 4.61 (m, 1H), 4.40 (t,J=6.22, 2H), 4.19 (t, J=6.11 Hz, 2H), 3.71 (s, 3H), 3.08–2.96 (m, 2H), 2.23 (quintet, J=6.15 Hz, 2H).

5. Methyl (2S)-3-{4-[3-(aminooxy)propoxy]phenyl}-2-[(phenylmethoxy)carbonylamino]propanoate

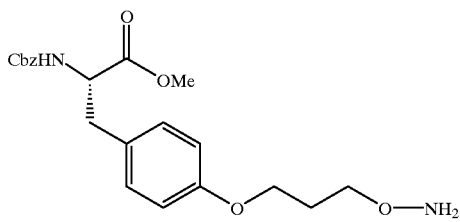

To a solution of 78 mg (0.15 mmol) of methyl (2S)-3-{4-[3-(1,3-dioxoisoindolin-2-yloxy)propoxy]phenyl}-2-[(phenylmethoxy)carbonylamino]propanoate, as prepared in the preceding step, in 5 mL THF was added 0.4 mL of 2M methylamine solution in THF. The solution was stirred at room temperature for 3 h. The solvent was then removed under reduced pressure. The mixture was chromatographed on a silica gel column using EtOAc/hexanes (3:7 to 7:3 v/v) as eluent to yield 47 mg (80%) of viscous liquid as product: $^1$H NMR (300 MHz, CDCl$_3$) δ7.38–7.28 (m, 5H), 6.98 (d, J=8.70 Hz, 2H), 6.79 (d, J=8.70 Hz, 2H), 5.20 (d, J=8.20 Hz, 1H), 5.10 (d, J=12.34 Hz, 1H), 5.05 (d, J=12.34 Hz, 1H), 4.60 (m, 1H), 3.99 (t, J=6.30 Hz, 2H), 3.84 (t, J=6.20 Hz, 2H), 3.71 (s, 3H), 3.10–2.97 (m, 2H), 2.05 (quintet, J=6.24 Hz, 2H).

6. tert-Butyl (2E)-3-{[3-(4-{(2S)-2-(methoxycarbonyl)-2-[(phenyl methoxy)carbonylamino]ethyl}phenoxy)propoxy]amino-2-aza-3-[(tert-butoxy)carbonylamino]prop-2-enoate

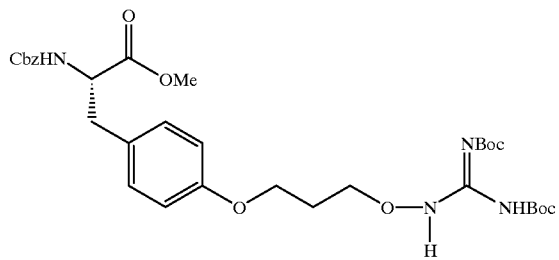

To a solution of 5.6 g (14.0 mmol) of methyl (2S)-3-{4-[3-(aminooxy)propoxy]phenyl}-2-[(phenylmethoxy)carbonylamino]propanoate, prepared in the preceding step, in 150 mL of anhydrous THF was added 5.6 g (18.1 mmol) of N,N'-bis-Boc-1-guanylpyrazole. The solution was stirred at room temperature overnight. The solvent was then removed under reduced pressure. The mixture was chromatographed on a silica gel column using EtOAc/hexanes (3:7 v/v) as eluent to yield 9.2 g (quantitative) of viscous liquid as product: $^1$H NMR (300 MHz, CDCl$_3$) δ9.08 (s, 1H), 7.63 (d, J=2.06 Hz, 1H), 7.38–7.27 (m, 5H), 6.97 (d, J=8.69 Hz, 2H), 6.78 (d, J=8.69 Hz, 2H), 5.22 (d, J=8.18 Hz, 1H), 5.12–5.04 (m, 2H), 4.60 (m, 1H), 4.22 (t, J=6.14 Hz, 2H), 4.01 (t, J=6.23 Hz, 2H), 3.70 (s, 3H),3.07–2.97 (m, 2H),2.14 (quintet, J=6.20 Hz, 2H), 1.47 (s, 18H)

7. tert-Butyl (2E)-3-[(3-{4-[(2S)-2-amino-2-(methoxycarbonyl)ethyl]phenoxy}propoxy)amino]-2-aza-3-[(tert-butoxy)carbonylamino]prop-2-enoate

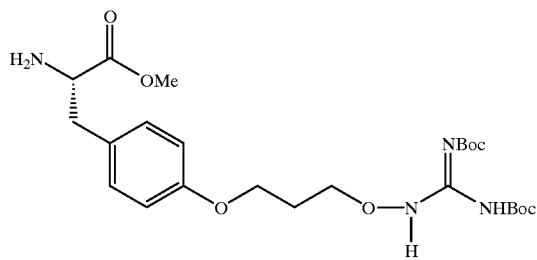

To a solution of 9.2 g (14 mmol) of tert-Butyl (2E)-3-{[3-(4-{(2S)-2-(methoxycarbonyl)-2-[(phenylmethoxy)carbonylamino]ethyl }phenoxy)propoxy]-amino-2-aza-3-[(tert-butoxycarbonylamino]prop-2-enoate, prepared in the preceding step, in 100 mL ethanol under nitrogen was added 1 g of 10 wt % Pd/C. The nitrogen was removed and hydrogen was adminstrated to the mixture using a balloon. The mixture was stirred at room temperature for 5 h and monitored by TLC. After the reaction was complete, the mixture was filtered on a pad of Celite. The solvent of the filtrate was removed under reduced pressure. The mixture was chromatographed on a silica gel column using EtOAc/hexanes (9:1 v/v) as eluent to yield 5.9 g (81%) of colorless viscous liquid as product: $^1$H NMR (300 MHz, CDCl$_3$) δ9.07 (s, 1H), 7.72 (s, 1H), 7.07 (d, J=8.66 Hz, 2H), 6.82 (d, J=8.66 Hz, 2H), 4.22 (t, J=6.13 Hz, 2H), 4.03 (t, J=6.22 Hz, 2H), 3.72–3.68 (m, 4H), 3.02 (dd, J=5.19, 13.71 Hz, 1H), 2.82 (dd, J=7.64. 13.71 Hz, 1H), 2.14 (quintet, J=6.18 Hz, 2H), 2.03 (s, 18H)

8. (2S)-3-{4-[3-(Amidinoaminooxy)propoxy]phenyl}-2-[(1-naphthylsulfonyl)amino]propanoic acid trifluoroacetic acid salt

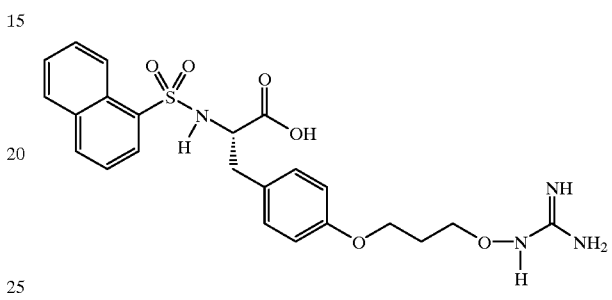

To 155 mL (60 mmol) of 0.39M of tert-Butyl (2E)-3-[(3-{4-[(2S)-2-amino-2-(methoxycarbonyl)ethyl]phenoxy}propoxy)amino]-2-aza-3-[(tert-butoxy)carbonylamino]prop-2-enoate, as prepared in the preceding step, in dichloroethane was added 31 mL (180 mmol) of diisopropylethylamine and 21 mg (90 mmol) of 1-naphthylsulfonyl chloride in 300 mL of 1,2-dichloroethane (DCE). The mixture was shaken at room temperature for 3 d. Then small amount of tris(2-aminoethyl)amine PS HL resin was added to the mixture and shaken for an additional 6 h. The mixture was then filtered and the resin was rinsed with additional 1,2-dichloroethane. The solvent of the combined filtrate was removed under reduced pressure in a SAVANT™. To the residue without purification was added 240 mL of THF/MeOH (2:1, v/v) solution, and 120 mL (240 mmol) of 2N LiOH solution. The mixture was shaken at room temperature for 2 d. The solvent was allowed to evaporate overnight. 400 mL (292 mmol) of 0.37 M HCl solution was added to the residue. The aqueous solution was then extracted with 1,2-dichloroethane (300 mL×3). The organic layers were combined and the solvent was removed under reduced pressure in a SAVANT™.

The residue was then dissolved in 200 mL of 1,2-dichloroethane. 400 mL of TFA/DCE (3:1, v/v) was added to the solution and the mixture was shaken at room temperature for 1 h. Then the solvent was removed under reduced pressure in a SAVANT™ to yield the desired product. $^1$H NMR (400 MHz, DMSO-d$_6$)$_d$ 11.14 (s, 1H), 8.51 (d, J=9.13 Hz, 1H), 8.45–8.43 (m, 1H), 8.03 (d, J=8.12 Hz, 1H), 7.93–7.90 (m, 1H), 7.80 (d, J=7.35 Hz, 1H), 7.70 (br s, 4H), 7.56–7.52 (m, 2H), 7.40 (t, J=7.81 Hz, 1H), 6.76 (d, J=8.58 Hz, 2H), 6.36 (d, J=8.61 Hz, 2H), 3.91 (t, J=5.74 Hz, 2H), 3.84 (t, J=6.02 Hz, 2H), 3.72 (dt, J=4.97,9.40 Hz, 1H), 2.76 (dd, J=4.78, 13.78 Hz, 1H), 2.51 (dt, J=9.93, 13.78 Hz, 1H), 1.99 (quintet, J=6.27 Hz, 2H); LRMS (EI) calcd for $C_{23}H_{26}N_4O_6S$ 487.2 (M+H), found 487.3.

The procedure just described was repeated in a similar fashion using parallel synthesis and yielded the following vitronectin receptor (a$_v$b$_3$ integrin) antagonists:

EXAMPLE 3

(2S)-3-{4-[3-(Amidinoaminooxy)propoxy]phenyl}-
2-{[(4-{[4-(dimethylamino)phenyl]diazenyl}-
phenyl)sulfonyl]amino}propanoic acid
trifluoroacetic acid salt

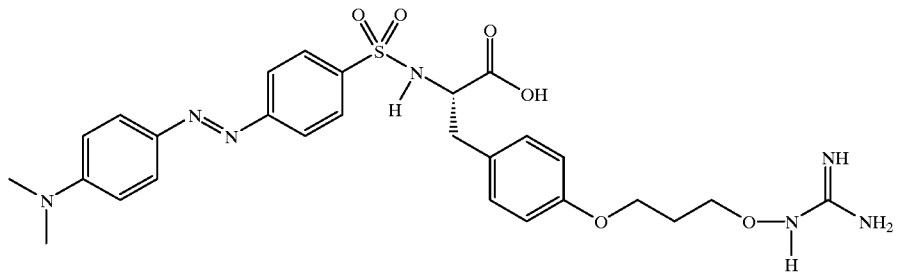

$^1$H NMR (400 MHz, DMSO-d$_6$) δ11.02 (s, 1H), 8.29 (d, J=9.14 Hz, 1H), 7.77 (d, J=9.18 Hz, 2H), 7.68 (d, J=8.54 Hz, 2H), 7.63 br s, 4H), 7.60 (d, J=8.67 Hz, 2H), 6.99 (d, J=8.59 Hz, 2H), 6.08 (d, J=9.22 Hz, 2H), 6.68 (d, J=8.59Hz, 2H), 3.90 (t, J=6.40 Hz, 2H), 3.84 (t, J=6.36 Hz, 2H), 3.80 (m, 1H), 3.03 (s, 6H), 2.83 (dd, J=5.20, 13.69 Hz, 1H), 2.59 (dd, J=6.9, 13.69 Hz, 1H), 1.94 (quintet, J=6.34 Hz, 2H); LMRS (EI) calcd for C$_{27}$H$_{33}$N$_7$O$_6$S 584.2 (M+H), found 584.3.

EXAMPLE 4

2-{[((1E)-2-Phenylvinyl)sulfonyl]amino}-(2S)-3-{4-
[3-(amidinoaminooxy)propoxy]phenyl}propanoic
acid trifluoroacetic acid salt

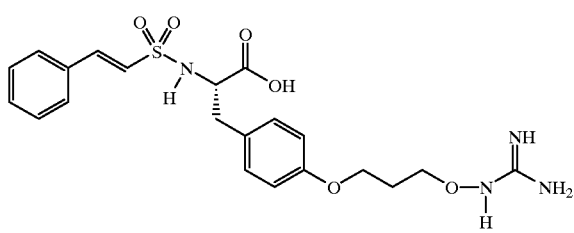

$^1$H NMR (300 MHz, DMSO-d$_6$) δ11.18 (s, 1H), 7.99 (d, J=9.1 Hz, 1H), 7.75 (br s, 4 H), 7.54–7.46 (m, 2H), 7.44–7.36 (m, 3H), 7.16 (d, J=8.5 Hz, 2H), 7.12 (d, J=15.3 Hz, 1H), 6.78 (d, J=8.5 Hz, 2H), 6.64 (d, J=15.3 Hz, 1H), 3.92 (t, J=6.36 Hz, 4H), 3.86 (dt, J=4.74, 9.27 Hz, 1H),2.96 (dd, J=4.99, 13.80 Hz, 1H), 2.73 (dd, J=9.73, 13.80 Hz, 1H), 2.05 (quintet, J=6.36 Hz, 2H); LRMS (EI) calcd for C$_{21}$H$_{26}$N$_4$O$_6$S 463.2 (M+H), found 463.3.

EXAMPLE 5

(2S)-3-{4-[3-(Amidinoaminooxy)propoxy]phenyl}-
2-{[(4-ethylphenyl)sulfony]amino}propanoic acid
trifluoroacetic acid salt

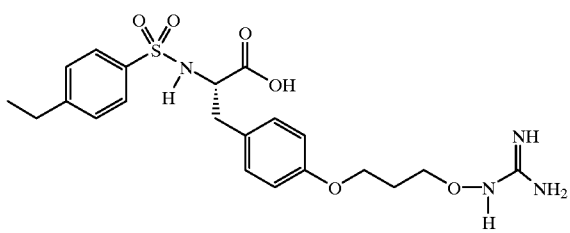

$^1$H NMR (400 MHz, DMSO-d$_6$) δ11.12 (s, 1H), 8.09 (d, J=8.91 Hz, 1H), 7.68 (br s, 4H), 7.41 (d, J=8.23 Hz, 2H), 7.19 (d, J=8.23 Hz, 2H), 6.95 (d, J=8.55 Hz, 2H) 6.69 (d, J=8.55 Hz, 2H), 3.96 (t, J=6.33 Hz, 2H), 3.90 (t, J=6.20 Hz, 2H), 3.73 (m, 1H), 2.80 (dd, J=5.32, 13.62 Hz, 1H), 2.61–2.54 (m, 3H), 2.01 (t, J=6.22 Hz, 2H), 1.12 (t, J=7.52 Hz, 3H); LRMS (EI) calcd for C$_{21}$H$_{28}$N$_4$O$_6$S 465 (M+H), found 465.3.

EXAMPLE 6

(2S)-3-{4-[3-(Amieinoaminooxy)propoxy]phenyl}-
2-{[(5-chloro(2- thienyl))sulfony]amino}propanoic
acid trifluoroacetic acid salt

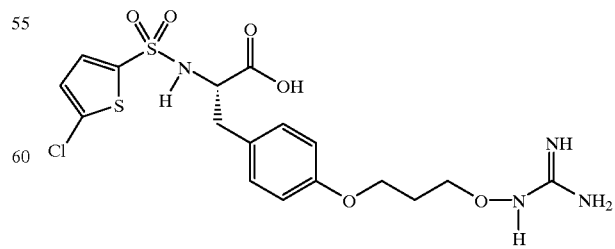

$^1$H NMR (400 MHz, DMSO-d$_6$) δ11.02 (s, 1H), 8.62 (d, J=9.03 Hz, 1H), 7.62 (br s, 4H), 7.12 (d, J=4.08 Hz, 1H), 7.01 (d, J=8.86 Hz, 2H), 6.99 (d, J=4.08 Hz, 1H), 6.71 (d, J=8.86 Hz, 2H), 3.97 (t, J=6.25 Hz, 2H), 3.90 (t, J=6.44 Hz, 2H), 3.80 (dt, J=4.78, 9.42 Hz, 1H), 2.87 (dd, J=4.78, 13.76 Hz, 1H), 2.59 (dd, J=9.91, 13.76 Hz, 1H), 2.01 (quintet, J=6.33 Hz, 2H); LRMS (EI) calcd for $C_{17}H_{21}ClN_4O_6S_2$ 477.1 (M+H), found 477.3.

EXAMPLE 7

(2S)-3-{4-[3-(Amidinoaminooxy)propoxy]phenyl}-2-{[(3-bromo-5-chloro(2-thienyl))sulfonyl]amino}propanoic acid trifluoroacetic acid salt

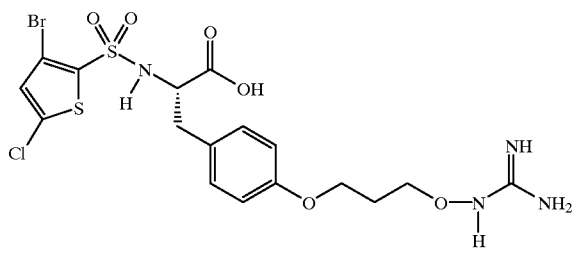

$^1$H NMR (400 MHz, DMSO-$d_6$) δ11.06 (s, 1H), 8.89 (d, J=9.15 Hz, 1H), 7.64 (br s, 4H), 7.16 (s, 1H), 7.03 (d, J=8.61 Hz, 2H), 6.69 (d, J=8.61 Hz, 2H), 3.96 (t, J=6.26 Hz, 2H), 3.92–3.87 (m, 3H), 2.91 (dd, J=4.27, 13.78 Hz, 1H), 2.63 (dd, J=10.48, 13.78 Hz, 1H), 2.01 (quintet, J=6.11 Hz, 2H); LRMS (EI) calcd for $C_{17}H_{20}BrClN_4O_6S_2$ 555.0 (M+H), found 557.1.

EXAMPLE 8

(2S)-3-{4-[3-(Amidinoaminooxy)propoxy]phenyl}-2-([[(3,5-dichloro-2-hydroxyphenyl)sulfonyl]amino}propanoic acid trifluoroacetic acid salt

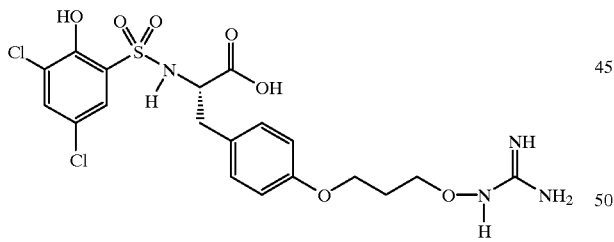

$^1$H NMR (400 MHz, DMSO-$d_6$) δ11.06 (s, 1H), 7.73 (br s, 5H), 7.59 (d, J=2.6 Hz, 1H), 7.29 (d, J=2.65 Hz, 1H), 7.00 (d, J=8.50 Hz, 2H), 6.66 (d, J=8.50 Hz, 2H), 4.03–3.87 (m, 5H), 3.53 (s, 1H), 2.87 (dd, J=4.86, 13.89 Hz, 1H), 2.68 (dd, J=10.56, 13.89 Hz, 1H), 2.00 (quintet, J=5.57 Hz, 2H); LRMS (EI) calcd for $C_{19}H_{22}Cl_2N_4O_7S$ 521.1 (M+H), found 521.3.

EXAMPLE 9

(2S)-3-{4-[3-(Amidinoaminooxy)propoxy]phenyl}-2-{[(4-nitrophenyl)sulfonyl]amino}propanoic acid trifluoroacetic acid salt

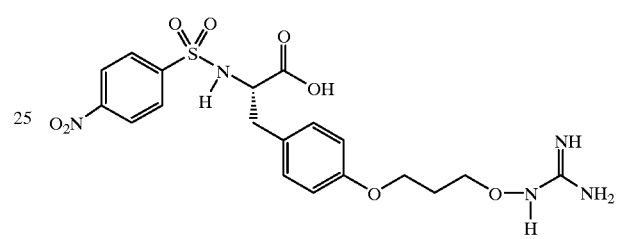

$^1$H NMR (300 MHz, DMSO-$d_6$) δ11.15 (s, 1H), 8.72 (d, J=9.06 Hz, 1H), 8.18 (d, J=8.95 Hz, 2H), 7.74 (br s, 4H), 7.69 (d, J=8.95 Hz, 2H), 6.99 (d, J=8.64 Hz, 2H), 6.62 (d, J=8.64 Hz, 2H), 3.9–3.85 (m, 5H), 2.92 (dd, J=4.34, 13.74 Hz, 1H), 2.60 (dd, J=10.51, 13.72 Hz, 1H), 2.04 (quintet, J=6.39 Hz, 2H); LRMS (EI) calcd for $C_{19}H_{23}N_5O_8S$ 482.1 (M+H), found 482.3.

EXAMPLE 10

(2S)-3-{4-[3-(Amidinoaminooxy)propoxy]phenyl)-2-{[(4-propylphenyl)sulfonyl]amino}propanoic acid trifluoroacetic acid salt

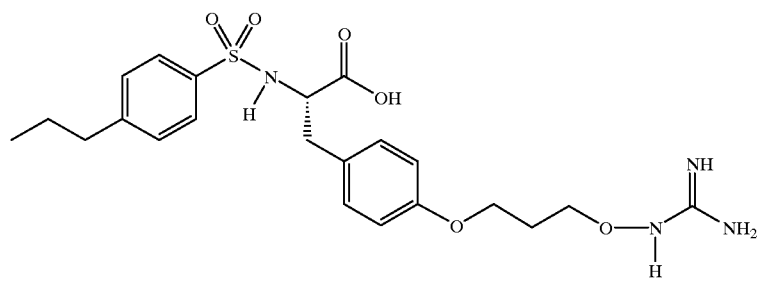

¹H NMR (400 MHz, DMSO-d$_6$) δ11.16 (s, 1H), 8.09 (d, J=8.92 Hz, 1H), 7.70 (br s, 4H), 7.40 (d, J=8.29 Hz, 2H), 7.17 (d,J=8.29 Hz, 2H), 6.95 (d,J=8.61 Hz 2H), 6.69 (d, J=8.61 Hz, 2H), 3.96 (t, J=6.26 Hz, 2H), 3.90 (t, J=6.34 Hz, 2H), 3.71 (dt, J=5.75, 8.86 Hz, 1H), 2.79 (dd, J=5.61, 13.76 Hz, 1H), 2.58–2.50 (m, 3H), 2.00 (quintet, J=6.37 Hz, 2H), 1.52 (m, 2H), 0.81 (t, J=7.32 Hz, 3H); LRMS (EI) calcd for C$_{22}$H$_{30}$N$_4$O$_6$S 479.2 (M+H), found 479.3.

EXAMPLE 11

(2S)-3-{4-[3-(Amidinoaminooxy)propoxy]phenyl)}-2-{[(2-methyl-5- nitrophenyl)sulfonyl] amino}propanoic acid trifluoroacetic acid salt

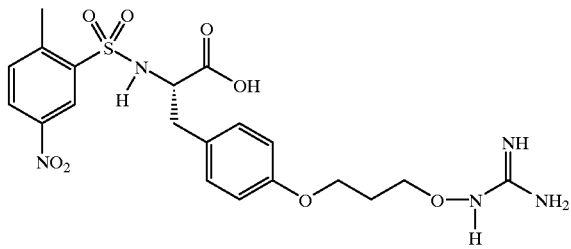

¹H NMR (300 MHz, DMSO-d$_6$) δ11.18 (s, 1H), 8.74 (d, J=9.29 Hz, 1 H), 8.30 (d, J=2.51 Hz, 1H), 8.21 (dd, J=2.51, 8.40 Hz, 1H), 7.75 (br s, 4 H), 7.44 (d, J=8.40 Hz, 1 H), 6.81 (d, J=8.61 Hz, 2H), 6.65 (d, J=8.61 Hz, 2H), 3.97–3.84 (m, 5H), 2.92 (dd, J=4.17, 14.02 Hz, 1H), 2.59 (dd, 3.36, 14.02 Hz, 1H), 2.47 (s, 3H), 2.07 (quintet, J=6.29 Hz, 2H); LRMS (EI) calcd for C$_{20}$H$_{25}$N$_5$O$_8$S 496.2 (M+H), found 496.4.

EXAMPLE 12

(2S)-3-{4-[3-(Amidinoaminooxy)propoxy]phenyl}-2-[(2-naphthylsulfonyl)amino]propanoic acid trifluoroacetic acid salt

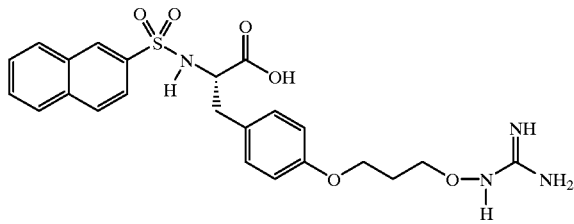

¹H NMR (400 MHz, DMSO-d$_6$) δ11.16 (s, 1H), 8.30 (d, J=9.11 Hz, 1H), 8.12 (s, 1H), 7.98 (d, J=8.01 Hz, 1H), 7.92 (d, J=8.01 Hz, 1H), 7.87 (d, J=9.02 Hz, 1H), 7.69 (br s, 4H), 7.51–7.56 (m, 2H), 7.52 (dd, J=1.86, 8.68 Hz, 1H), 6.94 (d, J=8.64 Hz, 2H), 6.57 (d, J=8.64 Hz, 2H), 3.88 (t, J=6.45 Hz, 2H), 3.85–3.80 (m, 3H), 2.82 (dd, J=5.34, 13.84 Hz, 1H), 2.58 (dd, J=9.46, 13.84 Hz, 1H), 1.98 (quintet, J=6.36 Hz, 2H); LRMS (EI) calcd for C$_{23}$H$_{26}$N$_4$O$_6$S 487.2 (M+H), found 487.3.

EXAMPLE 13

(2S)-3-{4-[3-(Amidinoaminooxy)propoxy]phenyl}-2-(}[2,4,6-tris(methylethyl)phenyl]sulfonyl}amino) propanoic acid trifluoroacetic acid salt

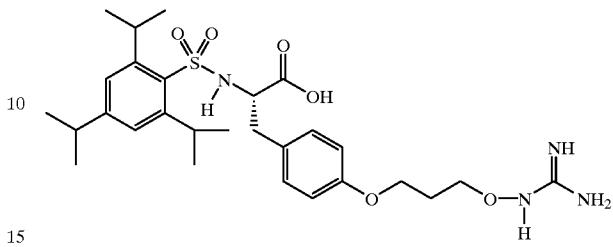

¹H NMR (400 Hz, DMSO-d$_6$) δ11.06 (s, 1H), 7.95 (d, J=9.17Hz, 1H), 7.10 (s, 2H), 7.65 (brs, 4H), 6.97 (d, J=8.48 Hz, 2H), 6.71 (d, J=8.48 Hz, 2H), 3.93 (t, J=5.70 Hz, 2H), 3.87 (t, J=6.20 Hz, 2H), 3.79 (dd, J=7.82, 15.72 Hz, 1H), 2.84 (dd, J=7.02, 13.84 Hz, 1H), 2.71 (dd, J=7.61, 13.39 Hz, 1H), 1.98 (quintet, J=6.29 Hz, 2H), 1.21–0.95 (m, 21H); LRMS (EI) calcd for C$_{28}$H$_{42}$N$_4$O$_6$S 563.3 (M+H), found 563.4.

EXAMPLE 14

(2S)-3-{4-[3-(Amidinoaminooxy)propoxy]phenyl}-2-{[(4-methoxyphenyl)sulfonyl]amino}propanoic acid trifluoroacetic acid salt

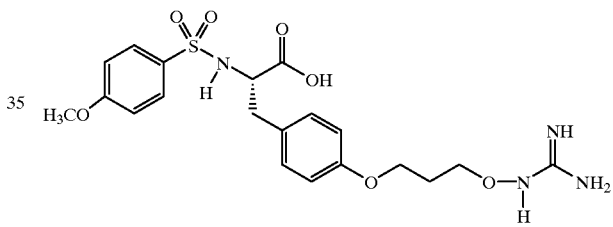

¹H NMR (400 MHz, DMSO-d$_6$) δ11.23 (s, 1H), 8.00 (d, J=9.00 Hz, 1H), 7.75 (br s, 4H), 7.44 (d, J=8.90 Hz, 2H), 6.95 (d, J=8.61 Hz, 2H), 6.87 (d, J=8.90 Hz, 2H), 6.69 (d, J=8.61 Hz, 2H), 3.96 (t, J=6.29 Hz, 2H), 3.89 (t, J=6.43 Hz, 2H), 3.74 (s, 3H), 3.69 (m, 1H), 2.78 (dd, J=5.61, 13.75 Hz, 1H), 2.56 (dd, J=8.98, 13.75 Hz, 1H), 2.00 (quintet, J=6.35 Hz, 2H); LRMS (EI) calcd for C$_{20}$H$_{26}$N$_4$O$_7$S 467.2 (M+H), found 467.3.

EXAMPLE 15

(2S)-3-{4-[3-(Amidinoaminooxy)propoxy]phenyl}-2-({[4-(1,1-dimethylpropyl)phenyl]sulfonyl}amino) propanoic acid trifluoroacetic acid salt

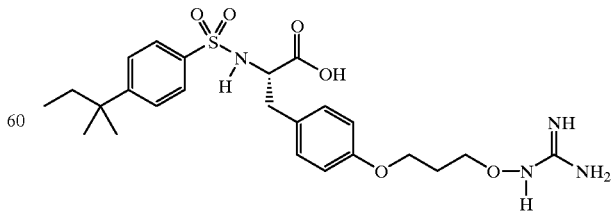

¹H NMR (400 MHz, DMSO-d$_6$) δ11.11 (s, 1H), 8.10 (d, J=8.86 Hz, 1H), 7.68 (br s, 4H), 7.42 (d, J=8.55 Hz, 2H), 7.31 (d, J=8.55 Hz, 2H), 6.95 (d, J=8.61 Hz, 2H), 6.70 (d, J=8.61 Hz, 2H), 3.97 (t, J=6.29 Hz, 2H), 3.89 (t, J=6.42 Hz, 2H), 3.70 (dt, J=5.73, 8.81 Hz, 1H), 2.80 (dd, J=5.73, 13.73 Hz, 1H), 2.55 (dd, J=8.86, 13.73 Hz, 1H), 2.00 (quintet, J=6.40 Hz, 2H), 1.55 (q, J=7.53 Hz, 2H), 1.18 (s, 6H), 0.53 (t, J=7.5 Hz, 3H); LRMS (EI) calcd for $C_{24}H_{34}N_4O_6S$ 507.2 (M+H), found 507.4.

EXAMPLE 16

(2S)-3-{4-[3-(Amidinoaminooxy)propoxy]phenyl}-2-({[2-(trifluoromethyl)phenyl]sulfonyl}amino)propanoic acid trifluoroacetic acid salt

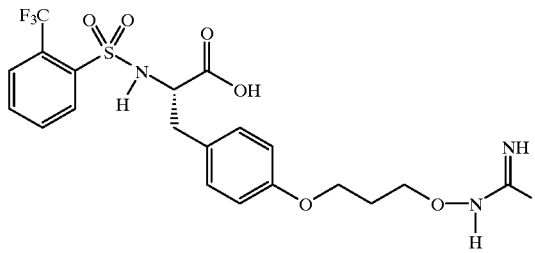

$^1$H NMR (400 MHz, DMSO-$d_6$) δ11.16 (s, 1H), 8.28 (d, J=9.08 Hz, 1H), 7.74–7.61 (m, 7H), 7.55 (t, J=7.58 Hz, 1H), 6.98 (d, J=8.61 Hz, 2H), 6.62 (d, J=8.61 Hz, 2H), 3.94 (t, J=6.17 Hz, 2H), 3.91 (t, J=6.17 Hz, 2H), 3.82 (dt, J=3.92, 9.95 Hz, 1H), 2.89 (dd, J=4.39, 13.70 Hz, 1H), 2.67 (dd, J=10.44, 13.70 Hz, 1H), 2.01 (quintet, J=6.32 Hz, 2H); LRMS (EI) calcd for $C_{20}H_{23}F_3N_4O_6S$ 505.1 (M+H), found 505.3.

EXAMPLE 17

(2S)-2-({[2-(Acetylamino)-4methyl(1,3-thiazol-5-yl)]sulfonyl}amino)-3-{4-[3-(amidinoaminooxy)propoxy]phenyl}propanoic acid trifluoroacetic acid salt

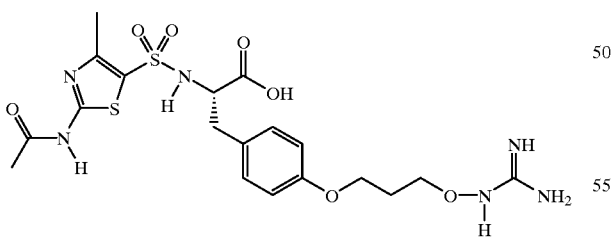

$^1$H NMR (400 MHz, DMSO-$d_6$) δ12.35 (s, 1H), 11.26 (s, 1H), 8.43 (d, J=9.22 Hz, 1H), 7.77 (br s, 4H), 6.99 (d, J=8.05 Hz, 2H), 6.68 (d, J=8.05 Hz, 2H), 3.94 (t, J=5.91 Hz, 2H), 3.89 (t, J=6.00 Hz, 2H), 3.75 (m, 1H), 2.84 (dd, J=5.03, 13.67 Hz, 1H), 2.67 (dd, J=10.57, 13.67 Hz, 1H), 2.22 (s, 3H), 2.10 (s, 3H), 2.00 (t, J=5.95 Hz, 2H); LRMS (EI) calcd for $C_{19}H_{26}N_6O_7S_2$ 515.1 (M+H), found 515.2.

EXAMPLE 18

(2S)-3-{4-[3-(Amidinoaminooxy)propoxy]phenyl}-2-{[[(2,4,6-trimethylphenyl)sulfonyl]amino}propanoic acid trifluoroacetic acid salt

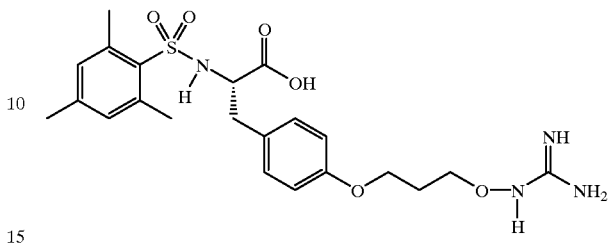

$^1$H NMR (400 MHz, DMSO-$d_6$) δ11.15 (s, 1H), 7.97 (d, J=9.42 Hz, 1H), 7.70 (br 4H), 6.89 (d, J=8.61 Hz, 2H), 6.80 (s, 2H), 6.62 ((d, J=8.61 Hz, 2H), 3.94 (t, J=6.34 Hz, 2H), 3.90 (t, J=6.43 Hz, 2H), 3.63 (dt, J=5.19 Hz, 9.47 Hz, 1H), 2.79 (dd, J=5.19, 13.77 Hz, 1H), 2.59 (dd, J=9.63, 13.77 Hz, 1H), 2.35 (s, 6H), 2.16 (s, 3H), 2.00 (quintet, J=6.35 Hz, 2H); LRMS (EI) calcd for $C_{22}H_{30}N_4O_6S$ 479.2 (M+H), found 479.3.

EXAMPLE 19

(2S)-3-{4-[3-(Amidinoaminooxy)propoxy]phenyl}-2-{[[(2,3,4-trichlorophenyl)sulfonyl]amino}propanoic acid trifluoroacetic acid salt

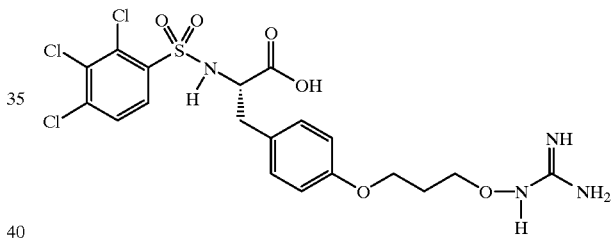

$^1$H NMR (400 MHz, DMSO-$d_6$) δ11.08 (s, 1H), 8.69 (d, J=9.07 Hz, 1H), 7.66 (br s, 4H), 7.59 (m, 2H), 6.91 (d, J=7.94 Hz, 2H), 6.52 (d, J=7.94 Hz, 2H), 3.92–3.89 (m, 4H), 3.85 (m, 1H), 2.88 (d, J=11.26 Hz, 1H), 2.60 (t, J=12.60 Hz, 1H), 2.01 (t, J=6.02 Hz, 2H); LRMS (EI) calcd for $C_{19}H_{21}Cl_3N_4O_6S$ 539.0 (M+H), found 541.2.

EXAMPLE 20

(2S)-3-{4-[3-(Amidinoaminooxy)propoxy]phenyl}-2-{[[(4-bromo-2,5-difluorophenyl)sulfonyl]amino}propanoic acid trifluoroacetic acid salt

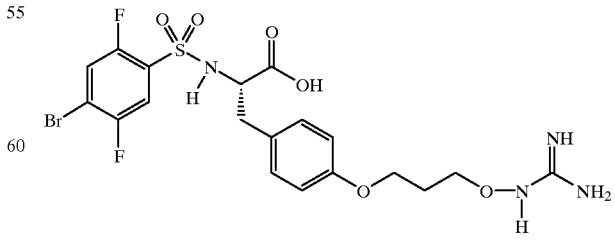

$^1$H NMR (400 MHz, DMSO-$d_6$) δ11.06 (s, 1H), 8.75 (d, J=9.14 Hz, 1H), 7.85 (s, 1H), 7.64 (br s, 4H), 7.34 (t, J=6.61

Hz, 1H), 6.99 (d, J=7.79 Hz, 2H), 6.63 (d, J=7.79 Hz, 2H), 3.95–3.84 (m, 5H), 2.90 (d, J=10.58 Hz, 1H), 2.61 (t, J=12.32 Hz, 1H), 2.02 (t, J=6.08 Hz, 2H); LRMS (EI) calcd for $C_{19}H_{21}BrF_2N_4O_6S$ 551.0 (M+H), found 553.2.

EXAMPLE 21

(2S)-3-{4-[3-(Amidinoaminooxy)propoxy]phenyl}-2-{[(3-chlorophenyl)sulfonyl]amino}propanoic acid trifluoroacetic acid salt

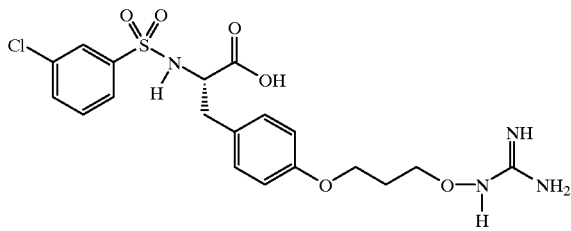

$^1$H NMR (400 MHz, DMSO-$d_6$) δ11.06 (s, 1H), 8.40 (d, J=9.11 Hz, 1H), 7.65 (br s, 4H), 7.53 (td, J=1.32, 7.92 Hz, 1H), 7.46–7.43 (m, 3H), 6.97 (d, J=8.64 Hz, 2H), 6.66 (d, J=8.64 Hz, 2H), 3.95 (t, J=6.29 Hz, 2H), 33.90 (t, J=6.47 Hz, 2H), 3.81 (dt, J=4.90, 9.33 Hz, 1H), 2.84 (dd, J=4.90, 13.79 Hz, 1H), 2.58 (dd, J=9.74, 13.79 Hz, 1H), 2.01 (quintet, J=6.32 Hz, 2H); LRMS (EI) calcd for $C_{19}H_{23}ClN_4O_6S$ 471.1 (M+H), found 471.4.

EXAMPLE 22

(2S)-3-{4-[3-(Amidinoaminooxy)propoxy]phenyl}-2-{[(3-chloro-2-methylphenyl)sulfonyl]amino}propanoic acid trifluoroacetic acid salt

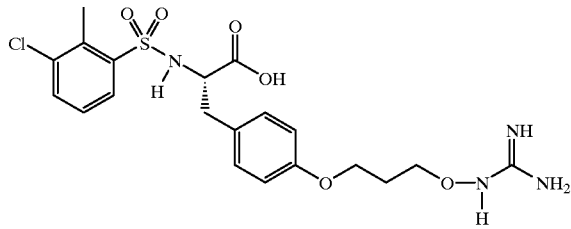

$^1$H NMR (400 Hz, DMSO-$d_6$) δ11.11 (s, 1H), 8.47 (d, J=9.33 Hz, 1H), 7.68 (br s, 4H), 7.54 (d, J=7.92 Hz, 1H), 7.81 (d, J=8.04 Hz, 1H), 7.17 (t, J=7.98 Hz, 1H), 6.87 (d, J=8.59 Hz, 2H), 6.58 (d, J=8.59 Hz, 2H), 3.95–3.89 (m, 4H), 3.66 (dt, J=4.20, 10.03 Hz, 1H), 2.84 (dd, J=4.20, 13.81 H, 1H), 2.56 (dd, J=10.81 Hz, 1H), 2.25 (s, 3H), 2.01 (quintet, J=6.35 Hz, 2H); LRMS (EI) calcd for $C_{20}H_{25}ClN_4O_6S$ 485.1 (M+H), found 485.3.

EXAMPLE 23

(2S)-3-{4-[3-(Amidinoaminooxy)propoxy]phenyl}-2-[(3-thienylsulfonyl)-amino]propanoic acid trifluoroacetic acid salt

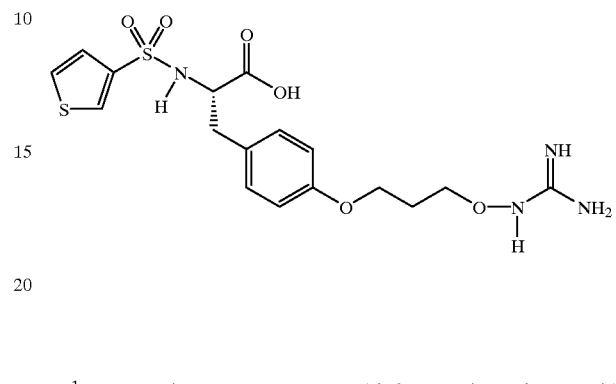

$^1$H NMR (400 MHz, DMSO-$d_6$) δ11.16 (s, 1H), 8.40 (d, J=8.90 Hz, 1H), 7.76 (dd, J=1.32, 5.00 Hz, 1H), 7.71 (br s, 4H), 7.26 (dd, J=1.34, 3.71 Hz, 1H), 6.99 (d, J=8.50 Hz, 2H), 6.97 (m, 1H), 6.72 (d, J=8.50 Hz, 2H), 3.97 (t, J=6.25 Hz, 2H), 3.89 (t, J=6.38 Hz, 2H), 3.80 (dt, J=5.74, 8.85 Hz, 1H), 2.83 (dd, J=5.74, 13.85 Hz, 1H), 2.59 (dd, J=8.81, 13.85 Hz, 1H), 2.00 (quintet, J=6.33 Hz, 2H); LRMS (EI) calcd for $C_{17}H_{22}N_4O_6S_2$ 443.1 (M+H), found 443.3.

EXAMPLE 24

(2S)-3-{4-[3-(Amidinoaminooxy)propoxy]phenyl}-2-{[(3-nitrophenyl)sulfonyl]amino}propanoic acid trifluoroacetic acid salt

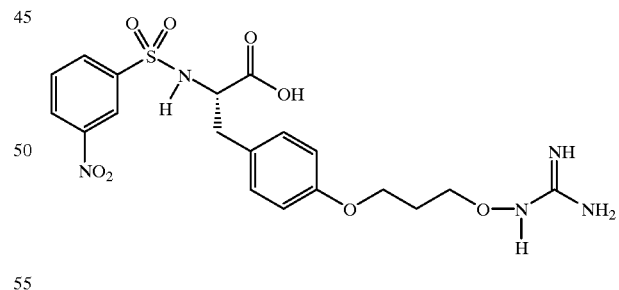

$^1$H NMR (300 MHz, DMSO-$d_6$) δ11.18 (s, 1H), 8.71 (d, J=9.11 Hz, 1H), 8.35 (ddd, J=1.02, 2.21, 8.26 Hz, 1H), 8.16 (t, J=1.94 Hz, 1H), 7.95 (ddd, J=1.07, 1.68, 7.78 Hz, 1H), 7.75 (br s, 4H), 7.71 (t, J=8.12 Hz, 1H), 6.98 (d, J=8.64 Hz, 2H), 6.60 (d, J=8.64 Hz, 2H), 3.96–3.87 (m, 5H), 2.92 (dd, J=4.59, 13.88 Hz, 1H), 2.61 (dd, J=10.37, 13.88 Hz, 1H), 2.06 (quintet, J=6.54 Hz, 2H); LRMS (EI) calcd for $C_{19}H_{23}N_5O_8S$ 482.1 (M+H), found 482.3.

EXAMPLE 25

(2S)-3-{4-[3-(Amidinoaminooxy)propoxy]phenyl}-2-({[4-(tert-butyl)phenyl]sulfonyl}amino)propanoic acid trifluoroacetic acid salt

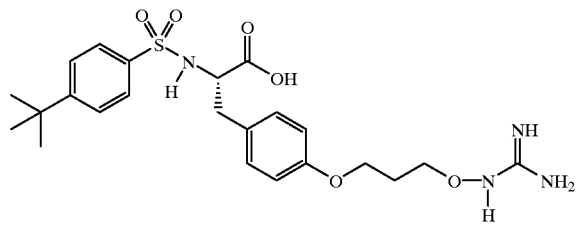

$^1$H NMR (400 MHz, DMSO-d$_6$) δ11.23 (s, 1H), 8.10 (d, J=8.77 Hz, 1H), 7.75 (br s, 4H), 7.40 (d, J=8.31 Hz, 2H), 7.36 (d, J=8.31 Hz, 2H), 6.95 (d, J=7.96 Hz, 2H), 6.69 (d, J=7.96 Hz, 2H), 3.96 (t, J=5.94 Hz, 2H), 3.89 (t, J=6.07 Hz, 2H), 3.71 (dd, J=9.49, 14.43 Hz, 1H), 2.80 (dd, J=5.31, 13.80 Hz, 1H), 2.57 (d, J=9.19, 13.51 Hz, 1H), 2.00 (quintet, J=6.15 Hz, 2H), 1.21 (s, 9H); LRMS (EI) calcd for C$_{23}$H$_{32}$N$_4$O$_6$S 493.2 (M+H), found 493.3.

EXAMPLE 26

(2S)-3-{4-[3-(Amidinoaminooxy)propoxy]phenyl}-2-{[(2,5-dimethoxyphenyl)sulfonyl]amino}propanoic acid trifluoroacetic acid salt

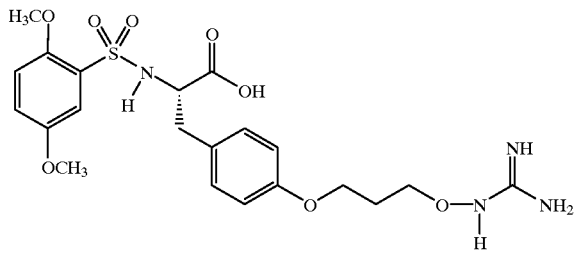

$^1$H NMR (300 MHz, DMSO-d$_6$) δ11.21 (s, 1H), 7.77 (br s, 4H), 7.58 (d, J=8.30 Hz, 1H), 7.15–6.98 (m, 5H), 6.76 (d, J=8.61 Hz, 2H ), 4.03–3.93 (m, 5H), 3.73 (s, 3H), 3.72 (s, 3H), 2.90 (dd, J=5.71, 13.55 Hz, 1H), 2.73 (dd, J=8.94, 13.55 Hz, 1H), 2.06 (quintet, J=6.36 Hz, 2H); LRMS (EI) calcd for C$_{21}$H$_{28}$N$_4$O$_8$S 497.2 (M+H), found 497.3.

EXAMPLE 27

(2S)-3-{4-[3-(Amidinoaminooxy)propoxy]phenyl}-2-{[(2-fluorophenyl)sulfonyl]amino}propanoic acid trifluoroacetic acid salt

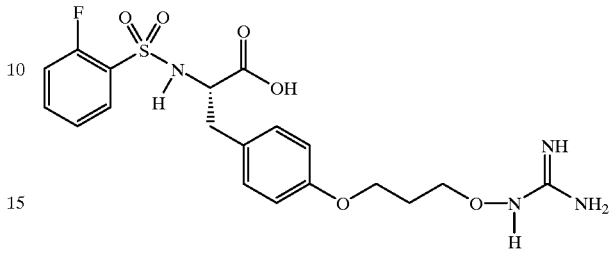

$^1$H NMR (400 MHz, DMSO-d$_6$) δ11.24 (s, 1H), 7.78 (br s, 4H), 8.48 (d, J=9.18 Hz, 1H), 7.58–7.54 (m, 2H), 7.24–7.19 (m, 2H), 7.06 (d, J=8.64 Hz, 2H), 6.73 (d, J=8.64 Hz, 2H), 4.01 (t, 6.23 Hz, 2H), 3.97 (t, J=6.41 Hz, 2H), 3.90 (dt, J=4.64, 9.57 Hz, 1H), 2.93 (dd, J=4.64, 13.78 Hz, 1H), 2.69 (dd, J=10.11, 13.78 Hz, 1H), 2.07 (quintet, J=6.30 Hz, 2H); LRMS (EI) calcd for C$_{19}$H$_{23}$FN$_4$O$_6$S 455.1 (M+H), found 455.3.

EXAMPLE 28

(2S)-3-{4-[3-(Amidinoaminooxy)propoxy]phenyl}-2-{[(3,5-dichlorophenyl)sulfonyl]amino}propanoic acid trifluoroacetic acid salt

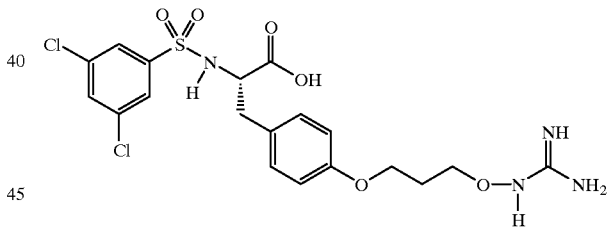

$^1$H NMR (400 MH, DMSO-d$_6$) δ11.05 (s, 1H), 8.57 (d, J=9.14 Hz, 1H), 7.70 (t, J=1.86 Hz, 1H), 7.64 (br s, 4H), 7.60 (d, J=1.86 Hz, 2H), 6.97 (d, J=8.60 Hz, 2H), 6.64 (d, J=8.60 Hz, 2H), 3.95–3.89 (m, 5H), 2.88 (dd, J=4.42, 13.84 Hz, 1H), 2.56 (dd, J=10.37, 13.84 Hz, 1H), 2.01 (quintet, J=6.33 Hz, 2H); LRMS (EI) calcd for C$_{19}$H$_{22}$Cl$_2$N$_4$O$_6$S 505.1 (M+H), found 505.5.

EXAMPLE 29

(2S)-3-{4-[3-(Amidinoaminooxy)propoxy]phenyl}-2-[({5-[1-methyl-5-(trifluoromethyl)pyrazol-3-yl]-(2-thienyl)}sulfonyl)amino]propanoic acid trifluoroacetic acid salt

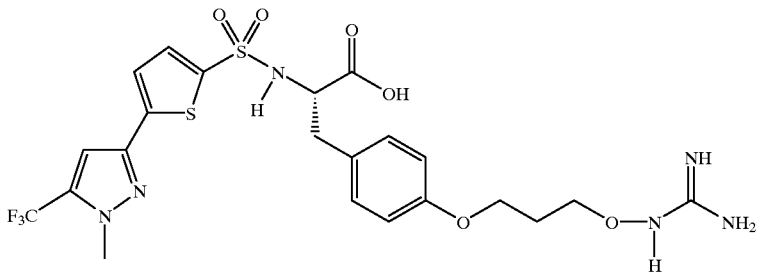

¹H NMR (400 MHz, DMSO-d₆) δ11.04 (s, 1H), 8.69 (d, J=8.98 Hz, 1H), 7.63 (br s, 4H), 7.35 (d, J=3.94 Hz, 1H), 7.33 (d, J=3.91 Hz, 1H), 7.05 (s, 1H), 7.02 (d, J=8.61 Hz, 2H), 6.69 (d, J=8.61 Hz, 2H), 3.96 (s, 3H), 3.88–3.79 (m, 5H), 2.86 (dd, J=8.15, 13.76 Hz, 1H), 2.62 (dd, J=9.91, 13.76 Hz, 1H), 1.93 (quintet, J=6.33 Hz, 2H); LRMS (EI) calcd for $C_{22}H_{25}F_3N_6O_6S_2$ 591.1 (M+H), found 591.2.

EXAMPLE 30

(2S)-3-{4-[3-(Amidinoaminooxy)propoxy]phenyl}-
2-{[(4-bromophenyl)sulfonyl]amino}propanoic acid
trifluoroacetic acid salt

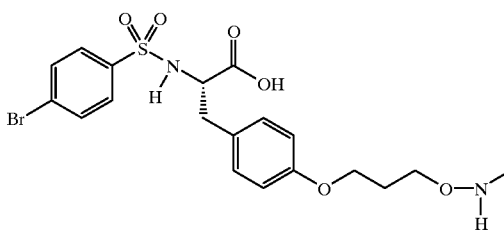

¹H NMR (400MHz, DMSO-d₆) δ11.13 (s, 1H), 8.33 (d, J=9.10 Hz, 1H), 7.69 (br s, 4H), 7.54 (d, J=8.62 Hz, 2H), 7.38 (d, J=8.62 Hz, 2H), 6.96 (d, J=8.63 Hz, 2H), 6.67 (d, J=8.63 Hz, 2H), 3.97 (t, J=6.30 Hz, 2H), 3.91 (d, J=6.47 Hz, 2H), 3.76 (dt, J=5.02, 9.36 Hz, 1H), 2.83 (dd, J=5.02, 13.81 Hz, 1H), 2.57 (dd, J=9.72, 13.81 Hz, 1H), 2.02 (quintet, J=6.37 Hz, 2H); LRMS (EI) calcd for $C_{19}H_{23}BrN_4O_6S$ 515.1 (M+H), found 517.1.

EXAMPLE 31

(2S)-3-{4-[3-(Amidinoaminooxy)propoxy]phenyl}-
2-{[(4-methylphenyl)sulfonyl]amino}propanoic acid
trifluoroacetic acid salt

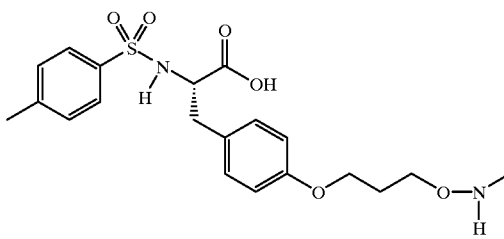

¹H NMR (400 MHz, DMSO-d₆) δ11.15 (s, 1H), 8.08 (d, J=8.99 Hz, 1H), 7.70 (br s, 4H), 7.9 (d, J=8.16 Hz, 2H), 7.16 (d, J=8.16 Hz, 2H), 6.96 (d, J=8.60 Hz, 2H), 6.69 (d, J=8.60 Hz, 2H), 3.96 (t, J=6.27 Hz, 2H), 3.90 (t, J=6.39 Hz, 2H), 3.72 (dt, J=5.62, 8.95 Hz, 1H), 2.79 (dd, J=5.62, 13.77 Hz, 1H), 2.56 (d, J=9.01, 13.77 Hz, 1H), 2.28 (s, 3H), 2.01 (quintet, J=6.33 Hz, 2H); LRMS (EI) calcd for $C_{20}H_{26}N_4O_6S$ 451.2 (M+H), found 451.3.

EXAMPLE 32

(2S)-3-{4-[3-(Amidinoaminooxy)propoxy]phenyl}-
2-{[(3-chloropropyl)sulfonyl]amino}propanoic acid
trifluoroacetic acid salt

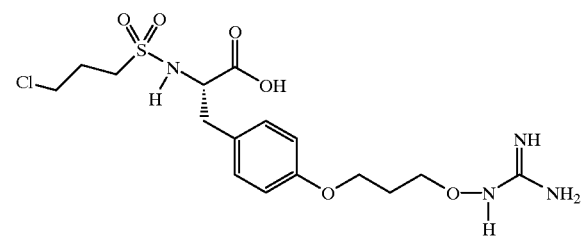

¹H NMR (400 MHz, DMSO-d₆) δ11.18 (s, 1H), 7.73 (d, J=9.26 Hz, 1H), 7.71 (br s, 4H), 7.31 (d, J=8.61 Hz, 2H), 6.80 (d, J=8.61 Hz, 2H), 3.98 (t, J=6.19 Hz, 2H), 3.88 (t, J=8.61 Hz, 2H), 3.47 (t, J=6.68 Hz, 2H), 3.30 (t, J=6.68 Hz, 2H), 2.83 (dd, J=4.96, 13.75 Hz, 1H), 2.72 (m, 1H), 2.65 (dd, J=9.83, 13.75 Hz, 1H), 2.00 (quintet, J=6.39 Hz, 2H), 1.80 (m, 1H), 1.75 (m, 1H); LRMS (EI) calcd for $C_{16}H_{25}ClN_4O_6S$ 437.1 (M+H), found 437.3.

EXAMPLE 33

(2S)-3-{4-[3-(Amidinoaminooxy)propoxy]phenyl}-
2-{[(2-methylphenyl)sulfonyl]amino}propanoic acid
trifluoroacetic acid salt

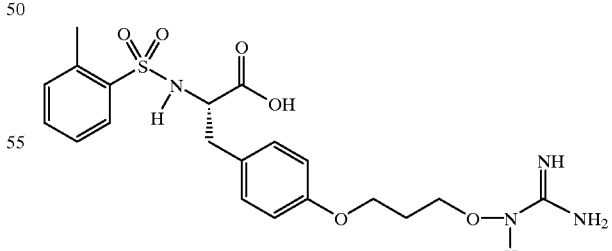

¹H NMR (400 MHz, DMSO-d₆) δ11.16 (s, 1H), 8.19 (d, J=9.29Hz, 1H), 7.71 (br s, 4H), 7.52 (dd, J=1.08, 7.89 Hz, 1H), 7.35 (dt, J=1.22, 7.49 Hz, 1H), 7.15 (t, J=8.21, 1H), 7.13 (d, J=7.32 Hz, 1H), 6.92 (d, J=8.65 Hz, 2H), 6.64 (d, J=8.65 Hz, 2H), 3.95 (t, J=6.21 Hz, 2H), 3.91 (t, J=6.41 Hz, 2H), 3.65 (dt, J=5.05, 9.50 Hz, 1H), 2.82 (dd, J=5.05, 13.68

Hz, 1H), 2.59 (dd, J=9.88, 13.68 Hz, 1H), 2.32 (s, 3H), 2.01 (quintet, J=6.34 Hz, 2H); LRMS (EI) calcd for $C_{20}H_{26}N_4O_6S$ 451.2 (M+H), found 451.3.

EXAMPLE 34

(2S)-3-{4-[3-(Amidinoaminooxy)propoxy]phenyl}-2-{[(3-fluorophenyl)sulfonyl]amino}propanoic acid trifluoroacetic acid salt

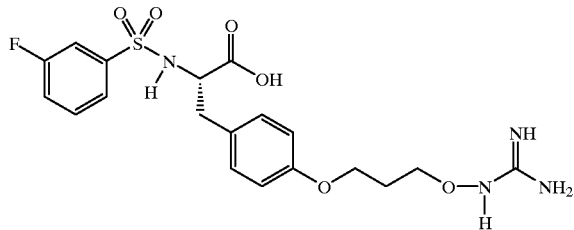

$^1$H NMR (400 MHz, DMSO-d$_6$) δ11.11 (s, 1H), 8.37 (d, J=9.09 Hz, 1H), 7.67 (br s, 4H), 7.41 (dd, J=5.50, 7.97 Hz, 1H), 7.35–7.31 (m, 2H), 7.17 (td, J=8.55, 2.04 Hz, 1H), 6.98 (d, J=8.62 Hz, 2H), 6.67 (d, J=8.62 Hz, 2H), 3.95 (t, J=6.29 Hz, 2H), 3.90 (t, J=6.44 Hz, 2H), 3.80 (dt, J=5.03, 9.33 Hz, 1H), 2.84 (dd, J=5.03, 13.80 Hz, 1H), 2.64 (dd, J=9.68, 13.80 Hz, 1H), 2.01 (quintet, J=6.31 Hz, 2H); LRMS (EI) calcd for $C_{19}H_{23}FN_4O_6S$ 455.1 (M+H), found 455.3.

EXAMPLE 35

(2S)-3-{4-[3-(Amidinoaminooxy)propoxy]phenyl}-2-{[(3-methylphenyl)sulfonyl]amino}propanoic acid trifluoroacetic acid salt

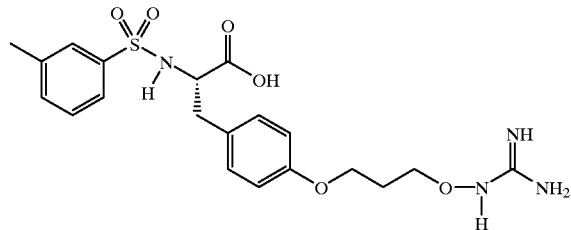

$^1$H NMR (400 MHz, DMSO-d$_6$) δ11.03 (s, 1H), 8.13 (d, J=9.04 Hz, 1H), 7.63 (br s, 4H), 7.36–7.23 (m, 4H), 6.96 (d, J=8.60 Hz, 2H), 6.68 (d, J=8.64 Hz, 2H), 3.95 (t, J=6.20 Hz, 2H), 3.90 (t, J=6.28 Hz, 2H), 3.73 (dt, J=5.44, 9.11 Hz, 1H), 2.80 (dd, J=5.46, 13.78 Hz, 1H), 2.56 (dd, J=9.29, 13.78 Hz, 1H), 2.23 (s, 3H), 2.00 (t, J=6.23 Hz, 2H); LRMS (EI) calcd for $C_{20}H_{26}N_4O_6S$ 451.1 (M+H), found 451.4.

EXAMPLE 36

(2S)-3-{4-[3-(Amidinoaminooxy)propoxy]phenyl}-2-[(phenylsulfonyl)amino]propanoic acid trifluoroacetic acid salt

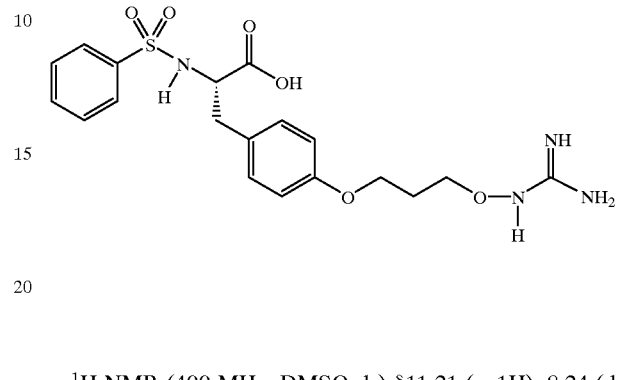

$^1$H NMR (400 MHz, DMSO-d$_6$) δ11.21 (s, 1H), 8.24 (d, J=8.97 Hz, 1H), 7.76 (br s, 4H), 7.58–7.55 (m, 3H), 7.43 (t, J=7.61 Hz, 2H), 7.03 (d, J=8.58 Hz, 2H), 6.75 (d, J=8.58 Hz, 2H), 4.03 (t, J=6.26 Hz, 2H), 3.97 (t, J=6.36 Hz, 2H), 3.82 (dt, J=5.63, 8.97 Hz, 1H), 2.87 (dd, J=5.63, 13.84 Hz, 1H), 2.63 (dd, J=9.08, 13.84 Hz, 1H), 2.07 (quintet, J=8.58 Hz, 2H); LRMS (EI) calcd for $C_{19}H_{24}N_4O_6S$ 437.1 (M+H), found 437.3.

EXAMPLE 37

(2S)-3-{4-[3-(Amidinoaminooxy)propoxy]phenyl}-2-{[(4-fluorophenyl)sulfonyl]amino}propanoic acid trifluoroacetic acid salt

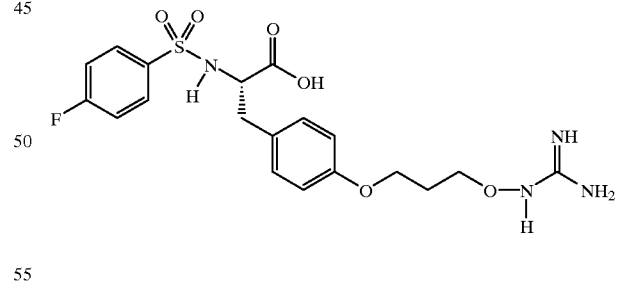

$^1$H NMR (400 MHz, DMSO-d$_6$) δ11.18 (s, 1H), 8.32 (d, J=9.08 Hz, 1H), 7.75 (br s, 4H), 7.60 (dd, J=5.22, 8.89 Hz, 2H, 7.24 (t, J=7.24, 8.89 Hz, 2H), 7.03 (d, J=8.65 Hz, 2H), 6.74 (d, J=8.65 Hz, 2H), 4.02 (t, J=6.32 Hz, 2H), 3.97 (t J=6.45 Hz, 2H), 3.82 (dt, J=5.23, 9.28 Hz, 1H), 2.89 (dd, J=5.23, 13.77 Hz, 1H), 2.63 (dd, J=9.48,13.77 Hz, 1H), 2.07 (quintet, J=6.31 Hz, 2H); LRMS (EI) calcd for $C_{19}H_{23}FN_4O_6S$ 455.1 (M+H), found 455.3.

EXAMPLE 38

(2S)-3-{4-[3-(Amidinoaminooxy)propoxy]phenyl}-2-{[(2,5-dimethylphenyl)sulfonyl]amino}propanoic acid trifluoroacetic acid salt

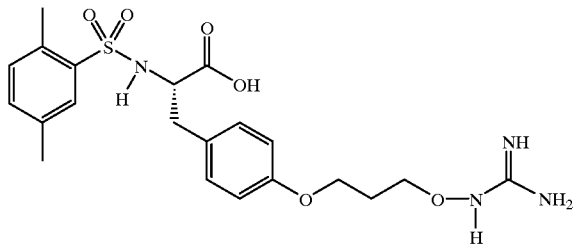

$^1$H NMR (300 MHz, DMSO-$d_6$) δ11.21 (s, 1H), 8.20 (d, J=9.25 Hz, 1H), 7.77 (br s,4H), 7.39 (d, J=1.29 Hz, 1H), 7.21(dd, J=1.29, 7.77 Hz, 1H), 7.07 (d, J=7.77 Hz, 1H), 6.98 (d, J=8.69 Hz, 2H), 6.70 (d, J=8.69 Hz, 2H), 4.00 (t, J=6.38 Hz, 2H), 3.96 (t, J=6.54 Hz, 2H), 3.73 (dt, J=5.00, 9.46 Hz, 1H), 2.87 (dd, J=5.0, 13.77 Hz, 1H), 2.65 (dd, J=9.77, 13.77 Hz, 1H), 2.34 (s, 3H), 2.24 (s, 3H), 2.03 (quintet, J=6.27 Hz, 2H); LRMS (EI) calcd for $C_{21}H_{28}N_4O_6S$ 465.2 (M+H), found 465.3.

EXAMPLE 39

(2S)-3-{4-[3-(Amidinoaminooxy)propoxy]phenyl}-2-({[(4-trifluoro-methoxy)phenyl]sulfonyl}amino) propanoic acid trifluoroacetic acid salt

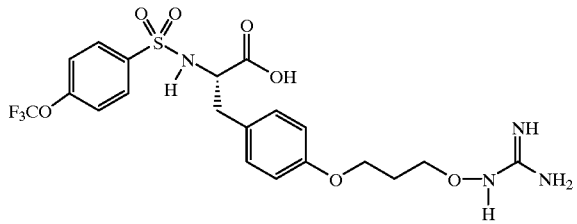

$^1$H NMR (400 MHz, DMSO-$d_6$) δ11.20 (s, 1H), 8.44 (d, J=9.05 Hz, 1H), 7.71 (br s, 4H), 7.66 (d, J=8.74 Hz, 2H), 7.39 (d, J=8.74 Hz, 2H), 7.04 (d, J=8.56 Hz, 2H), 6.74 (d, J=8.56 Hz, 2H), 4.02 (t, J=6.21 Hz, 2H), 3.96 (t, J=6.43 Hz, 2H), 3.85 (dt, J=5.01, 9.30 Hz, 1H), 2.91 (J=5.01, 13.84 Hz, 1H), 2.64 (dd, J=9.55, 13.84 Hz, 1H), 2.07 (quintet, J=6.32 Hz, 2H); LRMS (EI) calcd for $C_{20}H_{23}F_3N_4O_7S$ 521.1 (M+H), found 521.3.

EXAMPLE 40

(2S)-3-{4-[3-(Amidinoaminooxy)propoxy]phenyl}-2-{[(5-bromo-2-methoxyphenyl)sulfonyl]amino}propanoic acid trifluoroacetic acid salt

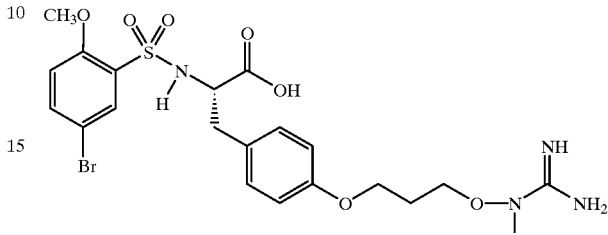

$^1$H NMR (400 MHz, DMSO-$d_6$) δ11.13 (s, 1H), 7.91 (d, J=8.95 Hz, 1H), 7.71 (br s, 4H), 7.67 (dd, J=2.55, 8.81 Hz, 1H), 7.62 (d, J=2.55 Hz, 1H), 7.07–7.02 (m, 3H), 6.74 (d, J=8.62 Hz, 2H), 4.02 (t, J=6.08 Hz, 2H), 4.00 (m, 1H), 3.97 (t, J=6.37 Hz, 2H), 3.79 (s, 3H), 2.92 (dd, J=4.76, 13.89 Hz, 1H), 2.72 (dd, J=9.73, 13.89 Hz, 1H), 2.07 (quintet, J=6.32 Hz, 2H); LRMS (EI) calcd for $C_{20}H_{25}BrN_4O_7S$ 545.1 (M+H), found 545.4.

EXAMPLE 41

(2S)-3-{4-[3-(Amidinoaminooxy)propoxy]phenyl}-2-({[2-chloro-5-(trifluoromethyl)phenyl]sulfonyl}amino)propanoic acid trifluoroacetic acid salt

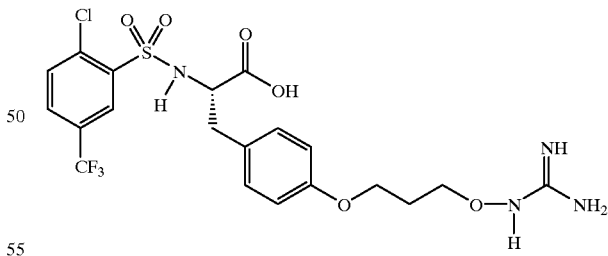

$^1$H NMR (400 MHz, DMSO-$d_6$) δ11.14 (s, 1H), 8.74 (d, J=9.08 Hz, 1H), 7.96 (s, 1H), 7.88 (d, J=8.35 Hz, 1H), 7.81–7.64 (m, 5H), 7.02 (d, J=7.40 Hz, 2H), 6.61 (d, J=7.40 Hz, 2H), 4.03–3.91 (m, 5H), 2.96 (dd, J=3.65, 19.93 Hz, 1H), 2.70 (t, J=12.09 Hz, 1H), 2.07 (t, J=5.77 Hz, 2H); LRMS (EI) calcd for $C_{20}H_{22}ClF_3N_4O_6S$ 539.1 (M+H), found 539.3.

EXAMPLE 42

(2S)-3-{4-[3-(Amidinoaminooxy)propoxy]phenyl}-
2-({[(4-chlorophenyl)sulfonyl]amino}propanoic
acid trifluoroacetic acid salt

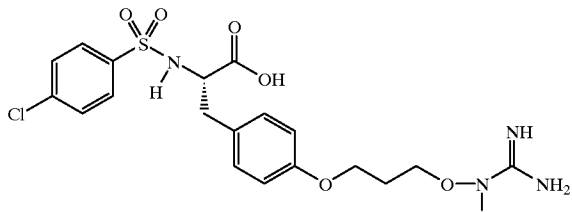

$^1$H NMR (400 MHz, DMSO-d$_6$) δ11.20 (s, 1H), 8.40 (d, J=9.09 Hz, 1H), 7.76 (br s, 4H), 7.53 (d, J=8.64Hz, 2H), 7.46 (d, J=8.64 Hz, 2H), 7.02 (d, J=8.60Hz, 2H), 6.73 (d, J=8.60 Hz, 2H), 4.03 (t, J=6.27 Hz, 2H), 3.97 (t, J=6.46 Hz, 2H), 3.83 (dt, J=5.04, 9.31 Hz, 1H), 2.89 (dd, J=5.04, 13.78 Hz, 1H), 2.63 (dd, J=9.71, 13.78 Hz, 1H), 2.08 (quintet, J=6.30 Hz, 2H); LRMS (EI) calcd for C$_{19}$H$_{23}$ClN$_4$O$_6$S 471.1 (M+H), found 471.4.

EXAMPLE 43

3-{[((IS)-2-{4-[3-Amidinoaminooxy)propoxyl]phenyl}-1-carboxyethyl)amino]sulfonyl}benzoic
acid trifluoroacetic acid salt

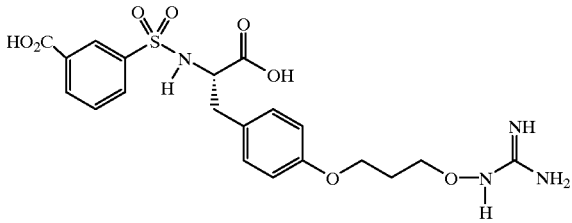

$^1$H NMR (400 MHz, DMSO-d$_6$) δ11.20 (br s, 1H), 8.80 (d, J=8.28 Hz, 1H), 8.09 (s, 1H), 7.82–7.73 (m, 6H), 7.42 (t, J=7.68 Hz, 1H), 7.22 (d, J=8.56 Hz, 2H), 6.83 (d, J=8.56 Hz, 2H), 4.58 (m, 1H), 4.01 (t, J=6.11 Hz, 2H), 3.93 (t, J=6.21 Hz, 2H), 3.12 (dd, J=4.42, 13.92 Hz, 1H), 3.02 (t, J=12.38 Hz, 1H), 2.02 (quintet, J=6.26 Hz, 2H); LRMS (EI) calcd for C$_{20}$H$_{24}$N$_4$O$_8$S 481.1 (M+H), found 481.4.

EXAMPLE 44

(2S)-3-{4-[3-(Amidinoaminooxy)propoxy]phenyl}-
2-{[(4-chloro-2,5-dimethylphenyl)sulfonyl]amino}propanoic acid trifluoroacetic acid salt

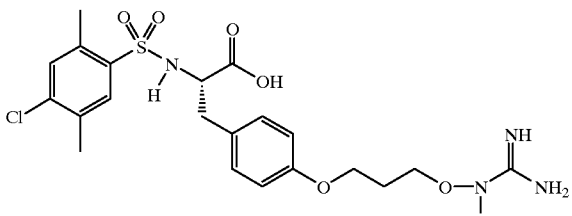

$^1$H NMR (400 MHz, DMSO-d$_6$) δ11.16 (s, 1H), 8.50 (d, J=9.33 Hz, 1H), 7.73 (br s, 4H), 7.52 (s, 1H), 7.21 (s, 1H), 6.97 (d, J=8.54 Hz, 2H), 6.67 (d, J=8.54 Hz, 2H), 4.01 (t, J=6.71 Hz, 2H), 3.98 (t, J=6.52 Hz, 2H), 3.76 (dt, J=4.49, 9.76 Hz, 1H), 2.89 (dd, J=4.49, 13.77 Hz, 1H), 2.63 (dd, J=10.47, 13.77 Hz, 1H), 2.33 (s, 3H), 2.27 (s, 3H), 2.08 (quintet, J=6.36 Hz, 2H); LRMS (EI) calcd for C$_{20}$H$_{27}$ClN$_4$O$_6$S 499.1 (M+H), found 499.4.

EXAMPLE 45

(2S)-3-{4-[3-(Amidinoaminooxy)propoxy]phenyl}-
2-{[(3,4 dimethoxyphenyl)sulfonyl]
amino}propanoic acid trifluoroacetic acid salt

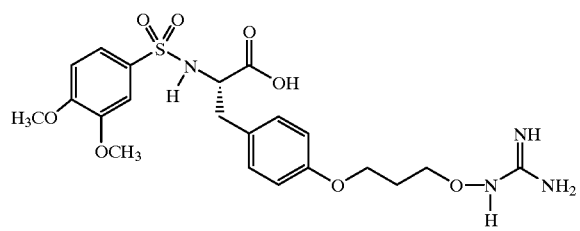

$^1$H NMR (400 MHz, DMSO-d$_6$) δ11.05 (s, 1H), 8.04 (d, J=8.97 Hz, 1H), 7.67 (br s,4H), 7.19 (dd, J=2.10, 8.51 Hz, Hz, 1H), 7.08 (d, J=2.10 Hz, 1H), 7.02 (d, J=8.59 Hz, 2H), 6.98 (d, J=8.51 Hz, 1H), 6.74 (d, J=8.59 Hz, 2H), 4.01 (t, J=6.15 Hz, 2H), 3.96 (t, J=6.43 Hz, 2H), 3.82 (m, 1H), 3.81 (s, 3H), 3.74 (s, 3H), 2.85 (dd, J=5.66, 13.76 Hz, 1H), 2.63 (dd, J=9.14, 13.76 Hz, 1H), 2.06 (quintet, J=6.28 Hz, 2H); LRMS (EI) calcd for C$_{21}$H$_{28}$N$_4$O$_8$S 497.2 (M+H), found 497.5.

EXAMPLE 46

(2S)-3-{4-[3-(Amidinoaminooxy)propoxy]phenyl}-
2-{[(2,6-dichlorophenyl)sulfonyl]amino}propanoic
acid trifluoroacetic acid salt

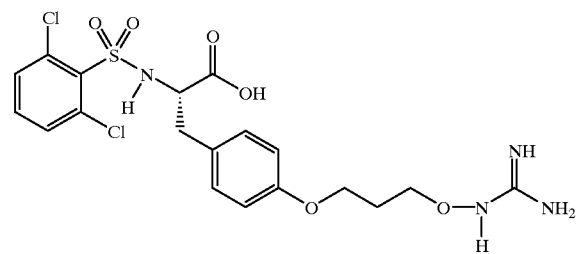

$^1$H NMR (400 MHz, DMSO-d$_6$) δ11.20 (s, 1H), 8.57 (d, J=9.11 Hz, 1H), 7.76 (br s, 4H), 7.45–7.35 (m, 3H), 7.04 (d, J=7.00 Hz, 2H), 6.62 (d, J=7.00 Hz, 2H), 4.03–3.90 (m, 5H),2.97 (dd, J=3.52, 13.81 Hz, 1H), 2.72 (t, J=11.99 Hz, 1H), 2.06 (t, J=5.76 Hz, 2H); LRMS (EI) calcd for C$_{19}$H$_{22}$Cl$_2$N$_4$O$_6$S 505.1 (M+H), found 505.4.

EXAMPLE 47

(2S)-3-{4-[3-(Amidinoaminooxy)propoxy]phenyl}-
2-{[(2,4,5-trichlorophenyl)sulfonyl]
amino}propanoic acid trifluoroacetic acid salt

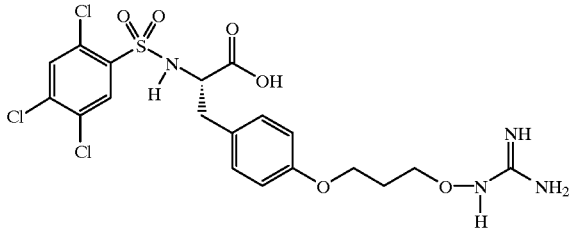

$^1$H NMR (300 MHz, DMSO-d$_6$) δ11.14 (s, 1H), 8.73 (d, J=9.14 Hz, 1H), 7.81 (s, 1H), 7.75 (s, 1H), 7.72 (br s, 4H), 7.03 (d, J=5.59 Hz, 2H), 6.63 (d, J=8.59 Hz, 2H), 4.01–3.94 (m, 5H), 2.96 (dd, J=3.98, 13.79 Hz, 1H), 2.67 (dd, J=10.93, 13.79 Hz, 1H), 2.07 (quintet, J=6.33 Hz, 2H); LRMS (EI) calcd for C$_{19}$H$_{21}$Cl$_3$N$_4$O$_6$S 539.0 (M+H), found 541.1.

EXAMPLE 48

(2S)-3-{4-[3-(Amidinoaminooxy)propoxy]phenyl}-
2-{[(4-chloro-3-nitrophenyl)sulfonyl]
amino}propanoic acid trifluoroacetic acid salt

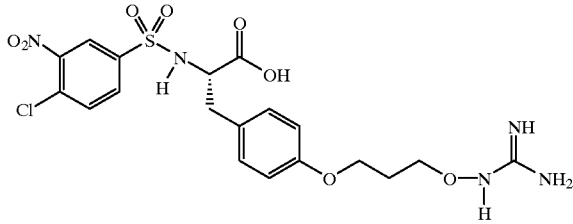

$^1$H NMR (400 MHz, DMSO-d$_6$) δ11.20 (s, 1H), 8.73 (d, J=9.14 Hz, 1H), 8.14 (d, J=2.07 Hz, 1H), 7.79–7.70 (m, 6H), 7.01 (d, J=8.56 Hz, 2H), 6.65 (d, J=8.56 Hz, 2H), 4.05–3.94 (m, 5H), 2.94 (dd, J=4.34, 13.80 Hz, 1H), 2.62 (dd, J=10.58, 13.80 Hz, 1H), 2.08 (quintet, J=6.38 Hz, 2H); LRMS (EI) calcd for C$_{19}$H$_{22}$ClN$_5$O$_8$S 516.1 (M+H), found 516.4.

EXAMPLE 49

(2S)-3-{4-[3-(Amidinoaminooxy)propoxy]phenyl}-
2-{[(4-methoxy-2,3,6-trimethylphenyl)sulfonyl]
amino}propanoic acid trifluoroacetic acid salt

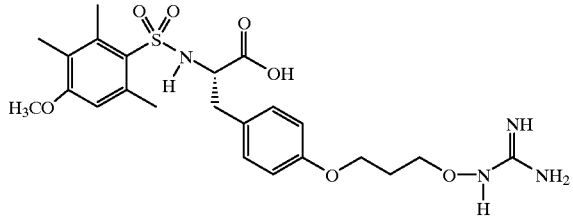

$^1$H NMR (400 MHz, DMSO-d$_6$) δ11.12 (s, 1H), 7.94 (d, J=9.42 Hz, 1H), 7.75 (br s, 4H), 6.92 (d, J=8.38 Hz, 2H), 6.66 (s, 1H), 6.65 (d, J=8.38 Hz, 2H), 3.97–3.94 (m, 4H), 3.81 (s, 3H), 3.66 (dt, J=4.60, 9.42 Hz, 1H), 2.85 (dd, J=4.60, 13.68 Hz, 1H), 2.64 (dd, J=10.24, 13.68 Hz, 1H), 2.49 (s, 3H), 2.21 (s, 3H), 2.06 (quintet, J=6.21 Hz, 2H), 1.96 (s, 3H); LRMS (EI) calcd for C$_{23}$H$_{32}$N$_4$O$_7$S 509.2 (M+H), found 509.3.

EXAMPLE 50

(2S)-3-{4-[3-(Amidinoaminooxy)propoxy]phenyl}-
2-{[(2-chlorophenyl)sulfonyl]amino}propanoic acid
trifluoroacetic acid salt

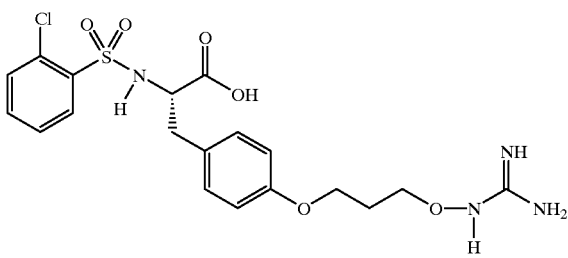

$^1$H NMR (300 MHz, DMSO-d$_6$) δ11.19 (s, 1H), 8.36 (d, J=9.03 Hz, 1H), 7.75 (br s, 4H), 7.69 (dd, J=1.47, 7.96 Hz, 1H), 7.52 (dt, J=1.54, 7.96Hz, 1H), 7.46 (dd, J=1.59, 7.96 Hz, 1H), 7.35 (dt, J=1.65, 7.96 Hz, 1H), 7.04 (d, J=8.60 Hz, 2H), 6.71 (d, J=8.60 Hz, 2H), 4.00 (t, J=6.17 Hz, 2H), 3.96 (t, J=6.35 Hz, 2H), 3.86 (dt, J=4.90, 9.09 Hz, 1H), 2.93 (dd, J=4.90, 13.77 Hz, 1H), 2.73 (dd, J=9.97, 13.77 Hz, 1H), 2.06 (quintet, J=6.26 Hz, 2H); LRMS (EI) calcd for C$_{19}$H$_{23}$ClN$_4$O$_6$S 471.1 (M+H), found 471.3.

EXAMPLE 51

(2S)-3-{4-[3-(Amidinoaminooxy)propoxy]phenyl}-
2-{[(2,3-dichlorophenyl)sulfonyl]amino}propanoic
acid trifluoroacetic acid salt

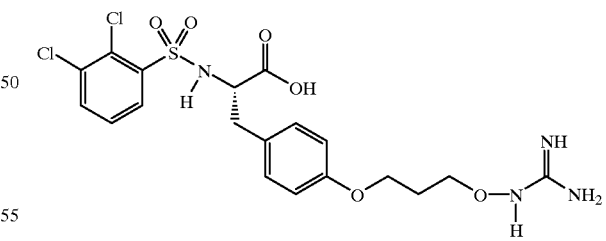

$^1$H NMR (400 Hz, DMSO-d$_6$) δ11.06 (s, 1H), 8.61 (d, J=9.14 Hz, 1H), 7.75 (dd, J=1.48, 8.05 Hz, 1H), 7.69 (dd, J=1.48, 7.91 Hz, 1H), 7.68 (br s, 4H), 7.37 (t, J=8.03 Hz, 1H), 7.00 (d, J=8.61 Hz, 2H), 6.63 (d, J=8.61 Hz, 2H), 3.98 (t, J=6.55 Hz, 4H), 3.88 (dt, J=4.27, 9.88 Hz, 1H), 2.94 (dd, J=4.27, 13.83 Hz, 1H), 2.69 (dd, J=10.88, 13.83 Hz, 1H), 2.07 (quintet, J=6.36 Hz, 2H); LRMS (EI) calcd for C$_{19}$H$_{22}$Cl$_2$N$_4$O$_6$S 505.1 (M+H), found 505.3.

EXAMPLE 52

(2S)-3-{4-[3-(Amidinoaminooxy)propoxy]phenyl}-2-{[(3-bromophenyl)sulfonyl]amino}propanoic acid trifluoroacetic acid salt

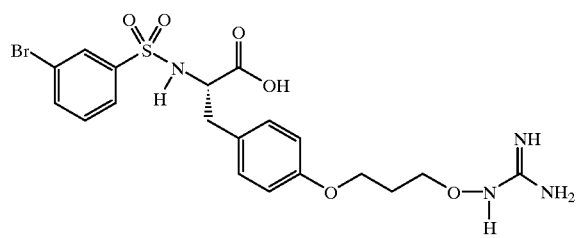

¹H NMR (400 MHz, DMSO-d₆) δ11.18 (s, 1H), 8.46 (d, J=9.09 Hz, 1H), 7.74–7.71 (m, 5H), 7.66 (s, 1H), 7.55 (d, J=7.82 Hz, 1H), 7.39 (t, J=7.92 Hz, 1H), 7.04 (d, J=8.50 Hz, 2H), 6.73 (d, J=8.50 Hz, 2H), 4.02 (t, J=6.30 Hz, 2H), 3.97 (t, J=6.45 Hz, 2H), 3.88 (dt, J=5.02, 9.29 Hz, 1H), 2.91 (dd, J=5.02, 13.75 Hz, 1H), 2.64 (dd, J=9.66, 13.75 Hz, 1H), 2.07 (quintet, J=6.33 Hz, 2H); LRMS (EI) calcd for C₁₉H₂₃BrN₄O₆S 515.1 (M+H), found 517.3.

EXAMPLE 53

(2S)-3-{4-[3-(Amidinoaminooxy)propoxy]phenyl}-2-{[(2,5-dichlorophenyl)sulfonyl]amino}propanoic acid trifluoroacetic acid salt

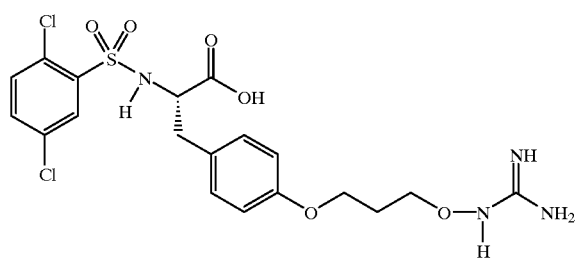

¹H NMR (400 MHz, DMSO-d₆) δ11.15 (s, 1H), 8.62 (d, J=9.00 Hz, 1H), 7.73 (br s, 4H), 7.64 (t, J=2.13 Hz, 1H), 7.58 (dd, J=2.30, 8.56 Hz, 1H), 7.49 (dd, J=1.73, 8.51 Hz, 1H), 7.06 (d, J=7.09 Hz, 2H), 6.87 (d, J=7.09 Hz, 2H), 4.01–3.94 (m, 5H), 2.97 (dd, J=4.09, 13.70 Hz, 1H), 2.71 (t, J=12.41 Hz, 1H), 2.08 (t, J=6.09 Hz, 2H); LRMS (EI) calcd for C₁₉H₂₂Cl₂N₄O₆S 505.1 (M+H), found 505.4.

EXAMPLE 54

(2S)-3-{4-[3-(Amidinoaminooxy)propoxy]phenyl}-2-{[(4-iodophenyl)sulfonyl]amino}propanoic acid trifluoroacetic acid salt

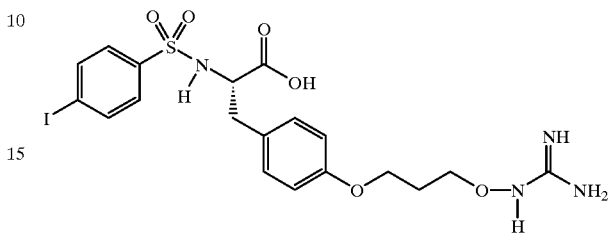

¹H NMR (400 MHz, DMSO-d₆) δ11.18 (s, 1H), 8.37 (d, J=9.03 Hz, 1H), 7.79 (d, J=8.11 Hz, 2H), 7.74 (brs, 4H), 7.29 (d, J=8.11 Hz, 2H), 7.03 (d, J=2H), 6.74 (d, J=7.99 Hz, 2H), 4.04 (t, J=6.13 Hz, 2H), 3.98 (t, J=6.11 Hz, 2H), 3.81 (m, 1H), 2.89 (dd, J=4.77, 13.63 Hz, 1H), 2.63 (dd, J=9.93, 13.63 Hz, 1H), 2.09 (quintet, J=6.19 Hz, 2H); LRMS (EI) calcd for C₁₉H₂₃IN₄O₆S 563.0 (M+H), found 563.2.

EXAMPLE 55

(2S)-3-{4-[3-(Amidinoaminoozy)propoxy]phenyl}-2-[(methylsulfonyl)amino]propanoic acid trifluoroacetic acid salt

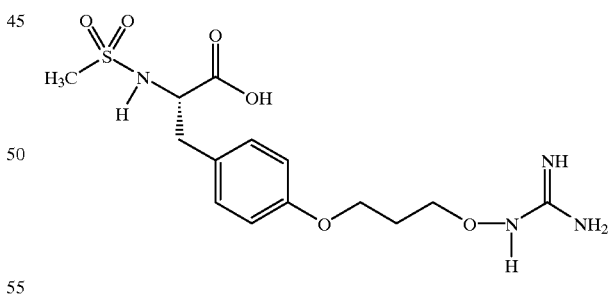

¹H NMR (400 MHz, DMSO-d₆) δ11.20 (s, 1H), 7.76 (br s, 4H), 7.64 (d, J=8.95 Hz, 1H), 7.20 (d, J=8.60 Hz, 2H), 6.87 (d, J=8.60 Hz, 2H), 4.04 (t, J=6.24 Hz, 2H), 3.98 (m, 1H), 3.95 (t, J=6.40 Hz, 2H), 2.98 (dd, J=5.11, 13.74 Hz, 1H), 2.73 (dd, J=9.46, 13.74 Hz, 1H), 2.59 (s, 3H), 2.06 (quintet, J=6.36 Hz, 2H); LRMS (EI) calcd for C₁₄H₂₂N₄O₆S 375.1 (M+H), found 375.3.

EXAMPLE 56

(2S)-3-{4-[3-(Amidinoaminooxy)propoxy]phenyl}-2-{[(2,3,4,5,6-pentamethylphenyl)sulfonyl]amino}propanoic acid trifluoroacetic acid salt

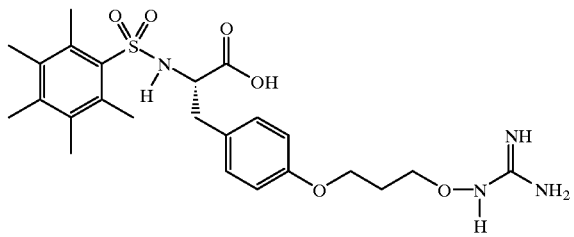

$^1$H NMR (300 MHz, DMSO-d$_6$) δ11.21 (s, 1H), 7.95 (d, J=9.27 Hz, 1H), 7.77 (br s, 4H), 6.92 (d, J=8.60 Hz, 2H), 6.63 (d, J=8.61 Hz, 2H), 3.97–3.92 (m, 4H), 3.75 (dt, J=4.92, 9.50 Hz, 1H), 2.86 (dd, J=4.92, 13.76 Hz, 1H), 2.66 (dd, J=9.85, 13.76 Hz, 1H), 2.30 (s, 6H), 2.19 (s, 3H), 2.10 (s, 6H), 2.05 (quintet, J=6.35 Hz, 2H); LRMS (EI) calcd for C$_{24}$H$_{34}$N$_4$O$_6$S 507.2 (M+H), found 507.3.

EXAMPLE 57

(2S)-3-{4-[3-(Amidinoaminooxy)propoxy]phenyl}-2-{[(3,4-dichlorophenyl)sulfonyl]amino}propanoic acid trifluoroacetic acid salt

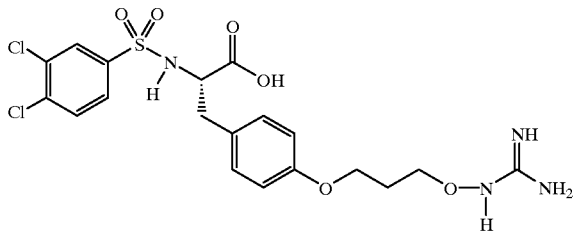

$^1$H NMR (400 MHz, DMSO-d$_6$) δ11.14 (s, 1H), 8.57 (d, J=9.14 Hz, 1H), 7.72 (br s, 4H), 7.67 (d, J=8.44 Hz, 1H), 7.62 (d, J=2.06 Hz, 1H), 7.47 (dd, J=2.06, 8.44 Hz, 1H), 7.03 (d, J=8.63 Hz, 2H), 6.69 (d, J=8.63 Hz, 2H), 4.00 (t, J=6.71 Hz, 2H), 3.97 (t, J=6.85 Hz, 2H), 3.91 (d, J=4.50, 9.67 Hz, 1H), 2.92 (dd, J=4.50, 13.84 Hz, 1H), 2.63 (dd, J=10.23, 13.79 Hz, 1H), 2.08 (quintet, J=6.35 Hz, 2H); LRMS (EI) calcd for C$_{19}$H$_{22}$Cl$_2$N$_4$O$_6$S 505.1 (M+H), found 505.4.

EXAMPLE 58

(2S)-3-{4-[3-(Amidinoaminooxy)propoxy]phenyl}-2-{[(4-bromo-2,5-dichloro(3-thienyl))sulfonyl]amino}propanoic acid trifluoroacetic acid salt

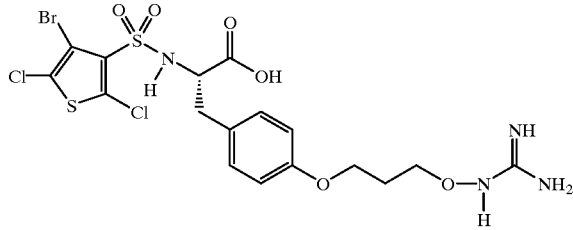

$^1$H NMR (400 MHz, DMSO-d$_6$) δ11.12 (s, 1H), 8.84 (d, J=9.28 Hz, 1H), 7.71 (br s, 4H), 7.07 (d, J=8.63 Hz, 2H), 6.70 (d, J=8.63 Hz, 2H), 4.03–3.92 (m, 5H), 2.98 (dd, J=3.65, 13.75 Hz, 1H), 2.67 (dd, J=11.29, 13.75 Hz, 1H), 2.08 (quintet, J=6.36 Hz, 2H); LRMS (EI) calcd for C$_{17}$H$_{19}$BrCl$_2$N$_4$O$_6$S$_2$ 588.9 (M+H), found 591.1.

EXAMPLE 59

(2S)-3-{4-[3-(Amidinoaminooxy)propoxy]phenyl}-2-{[(2-bromophenyl)sulfonyl]amino}propanoic acid trifluoroacetic acid salt

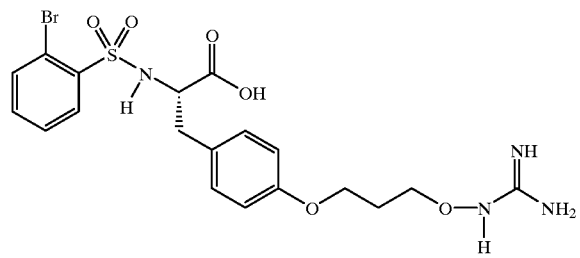

$^1$H NMR (400 MHz, DMSO-d$_6$) δ11.12 (s, 1H), 8.28 (d, J=8.99 Hz, 1H), 7.72–7.67 (m, 6H), 7.41 (m, 2H), 7.06 (d, J=8.63 Hz, 2H), 6.73 (d, J=8.63 Hz, 2H), 4.02 (t, J=6.14 Hz, 2H), 3.97 (t, J=6.42 Hz, 2H), 3.89 (dt, J=5.13, 9.25 Hz, 1H), 2.94 (dd, J=5.13, 13.84 Hz, 1H), 2.76 (dd, J=9.43, 13.84 Hz, 1H), 2.07 (quintet, J=6.32 Hz, 2H); LRMS (EI) calcd for C$_{19}$H$_{23}$BrN$_4$O$_6$S 515.1 (M+H), found 515.3.

EXAMPLE 60

(2S)-3-{4-[3-(Amidinoaminooxy)propoxy]phenyl}-2-({[(2-trifluoromethoxy)phenyl]sulfonyl}amino)propanoic acid trifluoroacetic acid salt

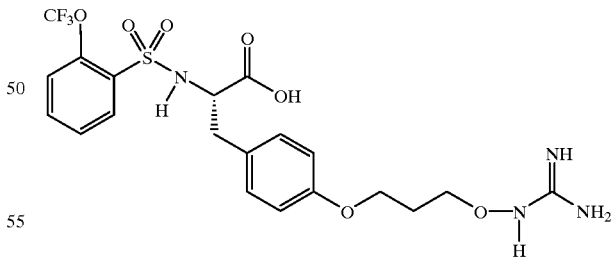

$^1$H NMR (400 MHz, DMSO-d$_6$) δ11.19 (s, 1H), 8.37 (d, J=9.16 Hz, 1H), 7.75 (br s, 4H), 7.67–7.63 (m, 2H), 7.39–7.33 (m, 2H), 7.08 (d, J=8.57 Hz, 2H), 6.74 (d, J=8.57 Hz, 2H), 4.02 (t, J=6.20 Hz, 2H), 3.99–3.91 (m, 3H), 2.95 (dd, J=4.70,1 3.84 Hz, 1H), 2.73 (dd, J=10.05, 13.84 Hz, 1H), 2.07 (quintet, J=6.29 Hz, 2H); LRMS (EI) calcd for C$_{20}$H$_{23}$F$_3$N$_4$O$_7$S 521.1 (M+H), found 521.2.

EXAMPLE 61

(2S)-3-{4-[3-(Amidinoaminooxy)propoxy]phenyl}-2-{[(2-nitrophenyl)sulfonyl]amino}propanoic acid trifluoroacetic acid salt

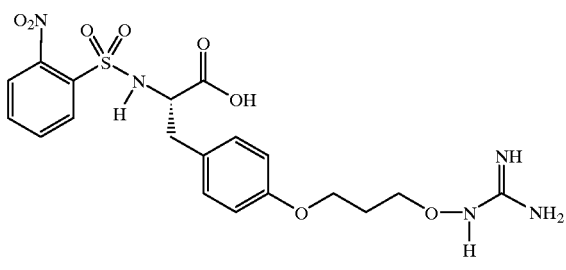

$^1$H NMR (400 MHz, DMSO-$d_6$) δ11.18 (s, 1H), 8.54 (d, J=9.01 Hz, 1H), 7.83 (d, J=7.65 Hz, 1H), 7.74–7.72 (m, 5H), 7.65–7.56 (m, 2H), 7.08 (d, J=8.52 Hz, 2H), 6.69 (d, J=8.52 Hz, 2H), 4.03–3.90 (m, 5H), 2.98 (dd, J=4.45, 13.74 Hz, 1H), 2.76 (dd, J=10.13, 13.74 Hz, 1H), 2.06 (quintet, J=6.27 Hz, 2H); LRMS (EI) calcd for $C_{19}H_{23}N_5O_8S$ 482.1 (M+H), found 482.4.

EXAMPLE 62

(2S)-2-({[4-Acetylamino)phenyl]sulfonyl}amino)-3-{4-[3-(amidinoaminooxy)propoxy]phenyl}propanoic acid trifluoroacetic acid salt

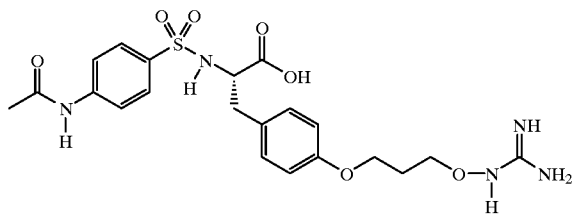

$^1$H NMR (400 MHz, DMSO-$d_6$) δ11.25 (br s, 1H), 10.30 (s, 1H), 8.08 (d, J=9.08 Hz, 1H), 7.79 (br s, 4H), 7.63 (d, J=8.84 Hz, 2H), 7.50 (d, J=8.84 Hz, 2H), 7.04 (d, J=8.62 Hz, 2H), 6.77 (d, J=8.62 Hz, 2H), 4.01 (t, J=6.26 Hz, 2H), 3.96 (t, J=6.41 Hz, 2H), 3.79 (dt, J=5.90, 8.90 Hz, 1H), 2.85 (dd, J=5.71, 13.80 Hz, 1H), 2.63 (dd, J=8.91, 13.80 Hz, 1H), 2.08 (s, 3H), 2.07 (m, 2H); LRMS (EI) calcd for $C_{21}H_{27}N_5O_7S$ 494.2 (M+H), found 494.3.

EXAMPLE 63

(2S)-3-{4-[3-(Amidinoaminooxy)propoxy]phenyl}-2-{[2-benzylsulfonyl]-amino}propanoic acid trifluoroacetic acid salt

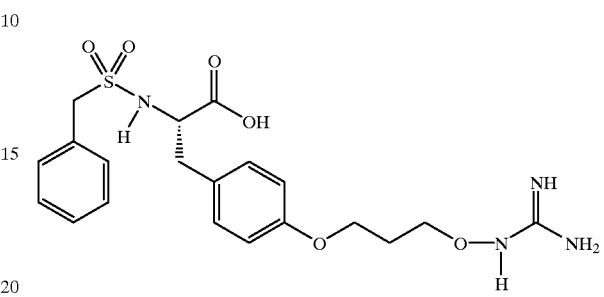

$^1$H NMR (400 MHz, DMSO-$d_6$) δ11.21 (br s, 1H), 7.76 (br s, 4H), 7.62 (d, J=8.58 Hz, 1H), 7.31–7.30 (m, 3H), 7.25 (t, J=8.58 Hz, 1H), 7.21–7.15 (m, 3H), 6.88 (d, J=8.55 Hz, 2H), 4.11 (t, J=13.64 Hz, 1H), 4.06–4.01 (m, 3H), 3.98–3.92 (m, 3H), 2.94 (dd, J=5.87, 13.79 Hz, 1H), 2.75 (dd, J=8.74, 13.79 Hz, 1H), 2.05 (quintet, J=6.30 Hz, 2H); LRMS (EI) calcd for $C_{20}H_{26}N_4O_6S$ 451.2 (M+H), found 451.3.

EXAMPLE 64

(2S)-3-{4-[3-(Amidinoaminooxy)propoxy]phenyl}-2-({[(3-(trifluoromethyl)phenyl]sulfonyl}amino) propanoic acid trifluoroacetic acid salt

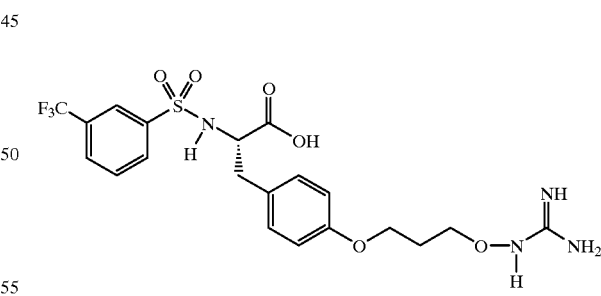

$^1$H NMR (400 MHz, DMSO-$d_6$) δ11.14 (s, 1H), 8.56 (d, J=9.17 Hz, 1H), 7.93–7.83 (m, 3H), 7.72 (br s, 4H), 7.68 (t, J=7.84 Hz, 1H), 7.03 (d, J=8.63 Hz, 2H), 6.70 (d, J=8.63 Hz, 2H), 4.01–3.90 (m, 5H), 2.92 (dd, J=5.00, 13.93 Hz, 1H), 2.65 (dd, J=9.65, 13.93 Hz, 1H), 2.07 (quintet, J=6.27 Hz, 2H); LRMS (EI) calcd for $C_{20}H_{23}F_3N_4O_6S$ 505.1 (M+H), found 505.3.

EXAMPLE 65

(2S)-3-{4-[3-(Amidinoaminooxy)propoxy]phenyl}-
2-{[(4,5-dibromo(2-thienyl))sulfonyl]
amino}propanoic acid trifluoroacetic acid salt

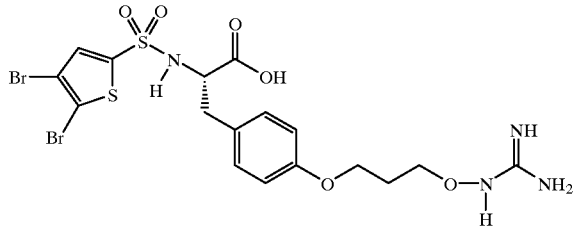

$^1$H NMR (400 MHz, DMSO-d$_6$) δ11.12 (s, 1H), 8.87 (d, J=9.02 Hz, 1H), 7.71 (br s, 4H), 7.19 (s, 1H), 7.09 (d, J=8.66 Hz, 2H), 6.76 (d, J=8.66 Hz, 2H), 4.03 (t, J=6.55 Hz, 2H), 3.99–3.90 (m, 3H), 2.96 (dd, J=4.24, 13.82 Hz, 1H), 2.65 (dd, J=10.50, 13.82 Hz, 1H), 2.08 (quintet, J=6.31 Hz, 2H); LRMS (EI) calcd for C$_{17}$H$_{20}$Br$_2$N$_4$O$_6$S$_2$ 598.9 (M+H), found 601.2.

EXAMPLE 66

(2S)-3-{4-[3-(Amidinoaminooxy)propoxy]phenyl}-
2-{[(2,5-dichloro(3-thienyl))sulfonyl]
amino}propanoic acid trifluoroacetic acid salt

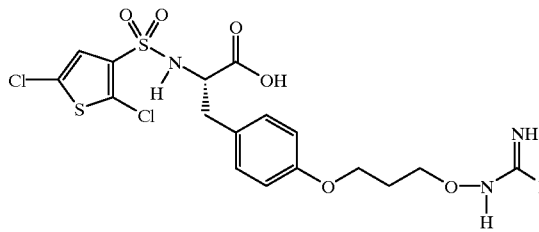

$^1$H NMR (400 MHz, DMSO-d$_6$) δ11.13 (s, 1H), 8.71 (d, J=9.19 Hz, 1H), 7.72 (br s, 4H), 7.10 (d, J=8.61 Hz, 2H), 6.85 (s, 1H), 6.77 (d, J=8.61 Hz, 2H), 5.53 (t, J=6.24 Hz, 2H), 3.98–3.93 (m, 3H), 2.98 (dd, J=4.24, 13.80 Hz, 1H), 2.67 (dd, J=10.65, 13.80 Hz, 1H), 2.08 (quintet, J=6.35 Hz, 2H); LRMS (EI) calcd for C$_{17}$H$_{20}$Cl$_2$N$_4$O$_6$S$_2$ 511.0 (M+H), found 511.3.

EXAMPLE 67

(2S)-3-{4-[3-(Amidinoaminooxy)propoxy]phenyl}-
2-{[(4-bromo-5-chloro(2-thienyl))sulfonyl]
amino}propanoic acid trifluoroacetic acid salt

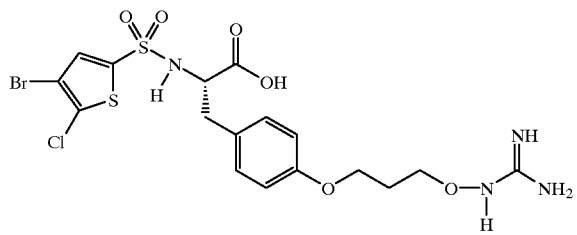

$^1$H NMR (400 MHz, DMSO-d$_6$) δ11.13 (s, 1H), 8.89 (d, J=9.01 Hz, 1H), 7.72 (br s, 4H), 7.23 (s, 1H), 7.09 (d, J=8.62 Hz, 2H), 6.75 (d, J=8.62 Hz, 2H), 4.03 (t, J=6.18 Hz, 2H), 3.98–3.91 (m, 3H), 2.97 (dd, J=4.12, 13.79 Hz, 1H), 2.65 (dd, J=10.64, 13.79 Hz, 1H), 2.08 (quintet, J=6.25 Hz, 2H); LRMS (EI) calcd for C$_{17}$H$_{20}$BrClN$_4$O$_6$S$_2$ 555.0 (M+H), found 557.0.

EXAMPLE 68

(2S)-3-{4-[3-(Amidinoaminooxy)propoxy]phenyl}-
2-{[(2-cyanophenyl)sulfonyl]amino}propanoic acid
trifluoroacetic acid salt

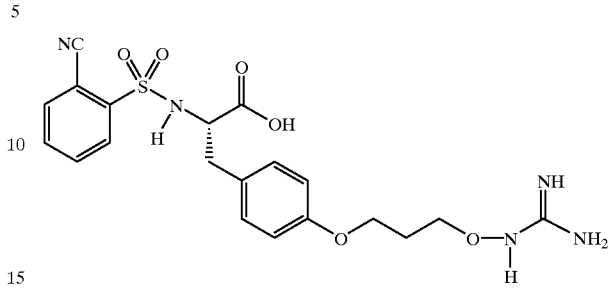

$^1$H NMR (400 MHz, DMSO-d$_6$) δ11.21 (s, 1H), 8.57 (d, J=9.14 Hz, 1H), 7.98 (td, J=1.29, 7.76 Hz, 1H), 7.77 (br s, 6 H), 7.63 (t, J=7.72 Hz, 1H), 7.02 (d, J=8.65 Hz, 2H), 6.69 (d, J=8.65 Hz, 2H), 4.03–3.91 (m, 5H), 2.92 (dd, J=4.60, 13.80 Hz, 1H), 2.64 (dd, J=10.12, 13.80 Hz, 1H), 2.08 (quintet, J=6.23 Hz, 2H); LRMS (EI) calcd for C$_{20}$H$_{23}$N$_5$O$_6$S 462.1 (M+H), found 462.3.

EXAMPLE 69

(2S)-3-{4-[3-(Amidinoaminooxy)propoxy]phenyl}-
2-{[(2,4,6-trichlorophenyl)sulfonyl]
amino}propanoic acid trifluoroacetic acid salt

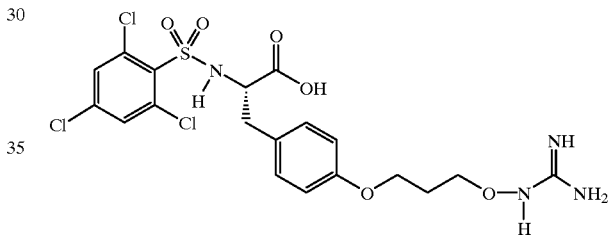

$^1$H NMR (300 MHz, DMSO-d$_6$) δ11.20 (s, 1H), 8.74 (d, J=9.23 Hz, 1H), 7.76 (br s, 4H), 7.59 (s, 2H), 7.03 (d, J=8.60 Hz, 22H), 6.61 (d, J=8.60 Hz, 2H), 4.04–3.94 (m, 5H), 2.98 (dd, J=3.96, 13.72 Hz, 1H), 2.69 (dd, J=11.20, 13.72 Hz, 1H), 2.07 (quintet, J=6.36 Hz, 2H); LRMS (EI) calcd for C$_{19}$H$_{21}$Cl$_3$N$_4$O$_6$S 539.0 (M+H), found 541.2.

EXAMPLE 70

(2S)-3-{4-[3-(Amidinoaminooxy)propoxy]phenyl}-
2-{[(5-chloro-3-methylbenzo[b]thiophen-2-yl)
sulfonyl]amino}propanoic acid trifluoroacetic acid
salt

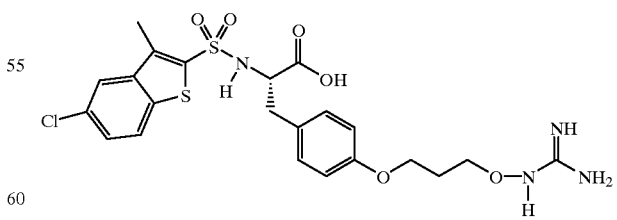

$^1$H NMR (400 MHz, DMSO-d$_6$) δ11.09 (s, 1H), 8.87 (d, J=9.16 Hz, 1H), 8.01 (d, J=8.67 Hz, 1H), 7.86 (d, J=2.01 Hz, 1H), 7.69 (br s, 4H), 7.54 (dd, J=2.01, 8.67 Hz, 1H), 6.97 (d, J=8.64 Hz, 2H), 6.47 (d, J=8.64 Hz, 2H), 3.94–3.89 (m, 4H), 3.76 (m, 1H), 2.91 (dd, J=4.07, 13.88 Hz, 1H), 2.63 (dd,

J=10.66, 13.88 Hz, 1H), 2.35 (s, 3H), 2.03 (quintet, J=6.44 Hz, 2H); LRMS (EI) calcd for $C_{22}H_{25}ClN_4O_6S_2$ 541.1 (M+H), found 541.3.

EXAMPLE 71

(2S)-3-{4-[3-(Amidinoaminooxy)propoxy]phenyl}-2-({[(4-(methylsulfonyl)phenyl]sulfonyl}amino)propanoic acid trifluoroacetic acid salt

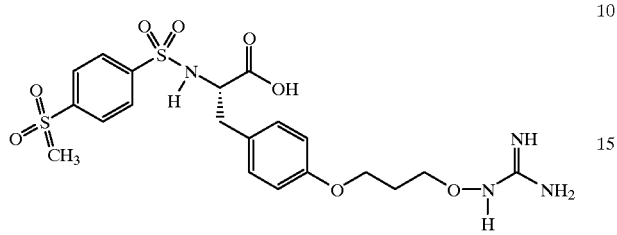

$^1$H NMR (400 MHz, DMSO-d$_6$) δ11.25 (s, 1H), 8.62 (d, J=9.04 Hz, 1H), 7.95 (d, J=8.35 Hz, 2H), 7.79 (br s, 4H), 7.75 (d, J=8.35 Hz, 2H), 7.03 (d, J=8.47 Hz, 2H), 6.72 (d, J=8.47 Hz, 2H), 4.02 (t, J=6.20 Hz, 2H), 3.96 (t, J=6.39 Hz, 2H), 3.90 (dt, J=4.88, 9.34 Hz, 1H), 3.27 (s, 3H), 2.93 (dd, J=4.88, 13.80 Hz, 1H), 2.65 (dd, J=9.91, 13.75 Hz, 1H), 2.07 (quintet, J=6.34 Hz, 2H); LRMS (EI) calcd for $C_{20}H_{26}N_4O_8S$ 515.1 (M+H), found 515.4.

EXAMPLE 72

(2S)-3-{4-[3-(Amidinoaminooxy)propoxy]phenyl}-2-{[(4-butoxyphenyl)sulfonyl]amino}propanoic acid trifluoroacetic acid salt

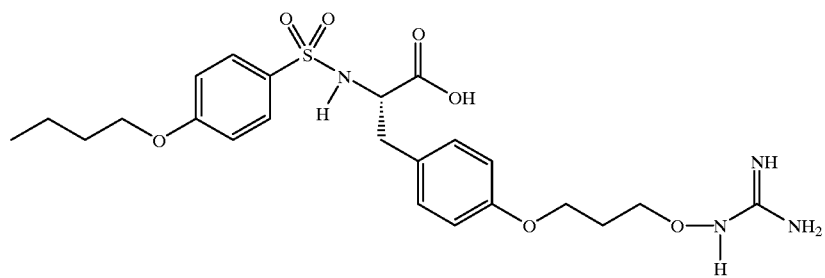

$^1$H NMR (400 MHz, DMSO-d$_6$) δ11.28 (s, 1H), 8.05 (d, J=8.97 Hz, 1H), 7.80 (br s, 4H), 7.49 (d, J=8.81 Hz, 2H), 7.02 (d, J=8.52 Hz, 2H), 6.93 (d, J=8.81 Hz, 2H), 6.77 (d, J=8.52 Hz, 2H), 4.04–3.99 (m, 4H), 3.96 (t, J=6.27 Hz, 2H), 3.75 (dt, J=5.80, 8.74 Hz, 1H), 2.85 (dd, J=5.80, 13.74 Hz, 1H), 2.63 (dd, J=8.92, 13.74 Hz, 1H), 2.07 (quintet, J=6.28 Hz, 2H), 1.73–1.67 (m, 2H), 1.46–1.40 (m, 2H), 0.94 (t, J=7.37 Hz, 3H); LRMS (EI) calcd for $C_{23}H_{32}N_4O_7S$ 509.2 (M+H), found 509.4.

EXAMPLE 73

(2S)-3-{4-[3-(Amidinoaminooxy)propoxy]phenyl}-2-{[(4-butylphenyl)sulfonyl]amino}propanoic acid trifluoroacetic acid salt

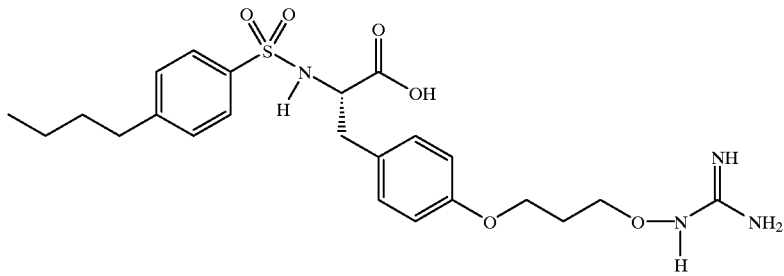

¹H NMR (400 MHz, DMSO-d₆) δ11.22 (br s, 1H), 8.15 (d, J=8.91 Hz, 1H), 7.77 (br s, 4H), 7.47 (d, J=8.25 Hz, 2H), 7.24 (d, J=8.25 Hz, 2H), 7.01 (d, J=8.54 Hz, 2H), 6.76 (d, J=8.54 Hz, 2H), 4.03 (t, J=6.22 Hz, 2H), 3.96 (t, J=6.33 Hz, 2H), 3.78 (dt, J=5.72, 8.80 Hz, 1H), 2.86 (dd, J=5.72, 13.74 Hz, 1H), 2.65–2.54 (m, 3H), 2.07 (quintet, J=6.36 Hz, 2H), 1.58–1.51 (m, 2H), 1.33–1.26 (m, 2H), 0.89 (t, J=7.33 Hz, 3H); LRMS (EI) calcd for $C_{23}H_{32}N_4O_6S$ 493.2 (M+H), found 493.4.

EXAMPLE 74

(2S)-3-{4-[3-(Amidinoaminooxy)propoxy]phenyl}-2-{[(2-methoxy-5-methylphenyl)sulfonyl]amino}propanoic acid trifluoroacetic acid salt

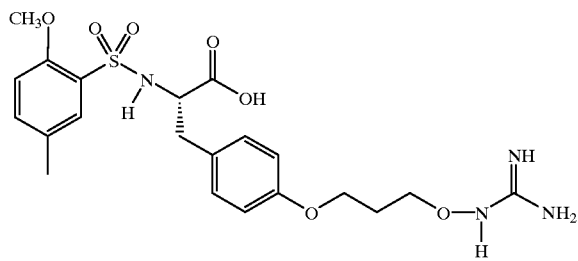

¹H NMR (400 MHz, DMSO-d₆) δ11.23 (s, 1H), 7.78 (br s, 4H), 7.47 (d, J=8.53 Hz, 1H), 7.40 (d, J=1.93 Hz, 1H), 7.32 (dd, J=1.93, 8.30 Hz, 1H), 7.05 (d, J=8.66 Hz, 2H), 6.97 (d, J=8.30 Hz, 1H), 6.77 (d, J=8.66 Hz, 2H), 4.02 (t, J=6.26 Hz, 2H), 3.98–3.91 (m, 3H), 3.75 (s, 3H), 2.89 (dd, 4.74, 13.4 Hz, 1H), 2.74 (dd, J=8.79, 13.87 Hz, 1H), 2.24 (s, 3H), 2.06 (quintet, J=6.34 Hz, 2H); LRMS (EI) calcd for $C_{21}H_{28}N_4O_7S$ 481.2 (M+H), found 481.3.

EXAMPLE 75

(2S)-3-{4-[3-(Amidinoaminooxy)propoxy]phenyl}-2-{[(4-phenylphenyl)sulfonyl]amino}propanoic acid trifluoroacetic acid salt

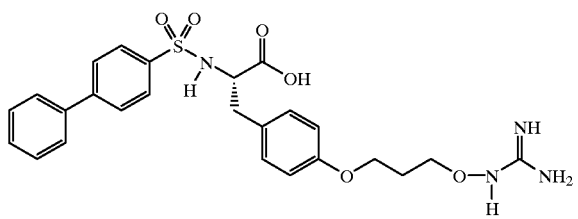

¹H NMR (400 MHz, DMSO-d₆) δ11.25 (s, 1H), 8.32 (d, J=8.97 Hz, 1H), 8.07 (d, J=8.56 Hz, 1H), 7.92 (d, J=8.59 Hz, 1H), 7.82 (br s, 4H), 7.72–7.64 (m, 4H), 7.53–7.50 (m, 2H), 7.45 (m, 1H), 7.02 (d, J=8.66 Hz, 2H), 6.71 (d, J=8.66 Hz, 2H), 3.95–3.82 (m, 5H), 2.89 (dd, J=4.99, 13.69 Hz, 1H), 2.66 (dd, J=9.51, 13.69 Hz, 1H), 1.96 (quintet, J=6.41 Hz, 2H); LRMS (EI) calcd for $C_{25}H_{28}N_4O_6S$ 513.2 (M+H), found 513.3.

EXAMPLE 76

(2S)-3-{4-[3-(Amidinoaminooxy)propoxy]phenyl}-2-{[(4-bromo-2-methylphenyl)sulfonyl]amino}propanoic acid trifluoroacetic acid salt

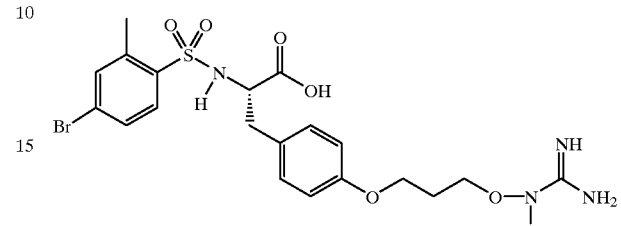

¹H NMR (400 MHz, DMSO-d₆) δ11.16 (s, 1H), 8.43 (d, J=9.33 Hz, 1H), 7.73 (br s, 4H), 7.49 (d, J=8.37 Hz, 1H), 7.43–7.39 (m, 2H), 6.98 (d, J=8.61 Hz, 2H), 6.68 (d, J=8.61 Hz, 2H), 4.03 (t, J=6.31 Hz, 2H), 3.98 (t, J=6.58 Hz, 2H), 3.72 (dt, J=4.54, 9.84 Hz, 1H), 2.89 (dd, J=4.54, 13.80 Hz, 1H), 2.64 (dd, J=10.46, 13.80 Hz, 1H), 2.36 (s, 3H), 2.09 (quintet, J=6.38 Hz, 2H); LRMS (EI) calcd for $C_{20}H_{25}BrN_4O_6S$ 529.1 (M+H), found 531.2.

EXAMPLE 77

(2S)-3-{4-[3-(Amidinoaminooxy)propoxy]phenyl}-2-{[(5-chloro-1,3-dimethylpyrazol-4-yl)sulfonyl]amino}propanoic acid trifluoroacetic acid salt

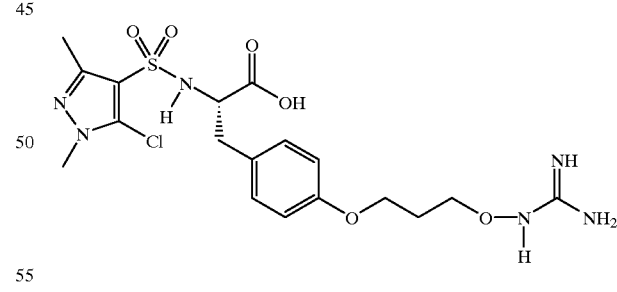

¹H NMR (400 MHz, DMSO-d₆) δ11.24 (s, 1H), 8.28 (d, J=9.29 Hz, 1H), 7.79 (br s, 4H), 7.04 (d, J=8.61 Hz, 2H), 6.73 (d, J=8.61 Hz, 2H), 4.03 (t, J=6.27 Hz, 2H), 3.97 (t, J=6.51 Hz, 2H), 3.78 (dt, J=4.28, 9.81 Hz, 1H), 3.64 (s, 3H), 2.90 (dd, J=4.28, 13.65 Hz, 1H), 2.63 (dd, J=10.27, 13.65 Hz, 1H), 2.15 (s, 3H), 2.08 (quintet, J=6.31 Hz, 2H); LRMS (EI) calcd for $C_{18}H_{25}ClN_6O_6S$ 489.1 (M+H), found 489.3.

EXAMPLE 78

(2S)-3-{4-[3-(Amidinoaminooxy)propoxy]phenyl}-2-{[(3,4-dibromophenyl)sulfonyl]amino}propanoic acid trifluoroacetic acid salt

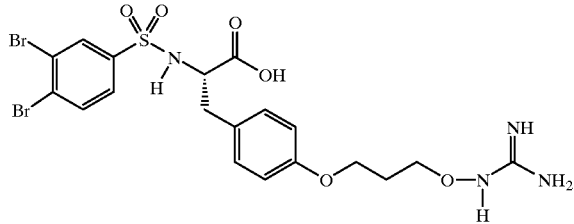

¹H NMR (400 MHz, DMSO-d₆) δ11.13 (s, 1H), 8.55 (d, J=9.13 Hz, 1H), 7.78–7.72 (m, 2H), 7.71 (br s, 4H), 7.41 (dd, J=2.13, 8.37 Hz, 1H), 7.03 (d, J=8.63 Hz, 2H), 6.70 (d, J=8.62 Hz, 2H), 4.02 (t, J=6.24 Hz, 2H), 3.97 (t, J=6.47 Hz 2H), 3.90 (dt, J=4.56, 9.61 Hz, 1H), 2.92 (dd, J=4.56, 13.85 Hz, 1H), 2.63 (dd, J=10.16, 13.85 Hz, 1H), 2.09 (quintet, J=6.34 Hz, 2H); LRMS (EI) calcd for $C_{19}H_{22}Br_2N_4O_6S$ 593.0 (M+H), found 595.2.

EXAMPLE 79

(2S)-3-{4-[3-(Amidinoaminooxy)propoxy]phenyl}-2-{[(4-vinylphenyl)sulfonyl]amino}propanoic acid trifluoroacetic acid salt

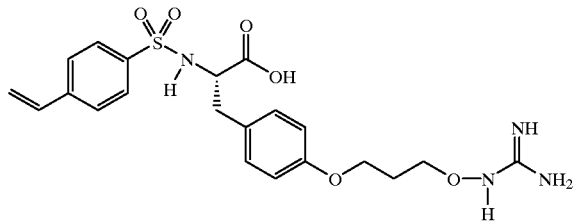

¹H NMR (400 MHz, DMSO-d₆) δ11.13 (s, 1H), 8.25 (d, J=9.06 Hz, 1H), 7.79 (br s, 4H), 7.49 (s, 4H), 7.02 (d, J=8.66 Hz, 2H), 6.77 (dd, J=11.04, 17.67 Hz, 1H), 6.74 (d, J=8.66 Hz, 2H), 5.96 (d, J=17.67 Hz, 1H), 5.42 (d, J=11.04 Hz, 1H), 4.00 (t, J=6.28 Hz, 2H), 3.96 (t, J=6.38 Hz, 2H), 3.82 (dt, J=5.44, 9.06 Hz, 1H), 2.87 (dd, J=5.44, 13.61 Hz, 1H), 2.64 (dd, J=9.62, 13.61 Hz, 1H), 2.06 (t, J=6.37 Hz, 2H); LRMS (EI) calcd for $C_{21}H_{26}N_4O_6S$ 463.2 (M+H), found 463.4.

EXAMPLE 80

(2S)-3-{4-[3-(Amidinoaminooxy)propoxy]phenyl}-2-({[4-bromo-2-(trifluoromethoxy)phenyl]sulfonyl}amino)propanoic acid trifluoroacetic acid salt

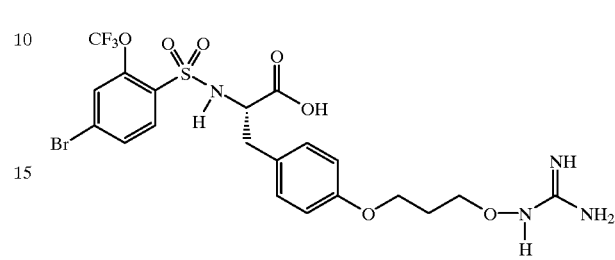

¹H NMR (400 MHz, DMSO-d₆) δ11.13 (s, 1H), 8.56 (d, J=9.17 Hz, 1H), 7.71 (br s, 4H), 7.62 (dd, J=1.69, 8.51 Hz, 1H), 7.58 (d, J=8.51 Hz, 1H), 7.50 (t, J=1.36 Hz, 1H), 7.05 (d, J=8.60 Hz, 2H), 6.71 (d, J=8.60 Hz, 2H), 7.02 (t, J=6.27 Hz, 2H), 3.98 (t, J=6.48 Hz, 2H), 3.91 (dt, J=4.07, 9.86 Hz, 1H), 2.95 (dd, J=4.07, 13.78 Hz, 1H), 2.70 (dd, J=10.68, 13.78 Hz, 1H), 2.09 (quintet, J=6.34 Hz, 2H); LRMS (EI) calcd for $C_{20}H_{22}BrF_3N_4O_7S$ 599.0 (M+H), found 601.1.

EXAMPLE 81

(2S)-3-{4-[3-(Amidinoaminooxy)propoxy]phenyl}-2-{[(6chloro-2-methylphenyl)sulfonyl]amino}propanoic acid trifluoroacetic acid salt

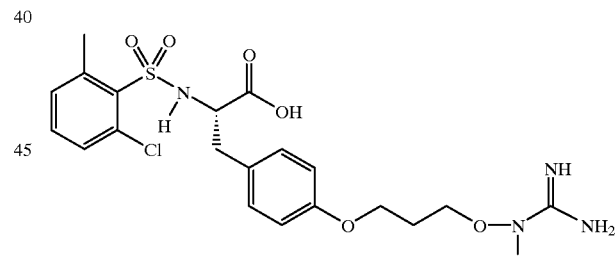

¹H NMR (300 MHz, DMSO-d₆) δ11.20 (s, 1H), 8.23 (dd, J=2.58, 9.13 Hz, 1H), 7.76 (br s, 4H), 7.31–7.28 (m, 2H), 7.19 (dd, J=3.46, 5.71 Hz, 1H), 7.01 (d, J=8.61 Hz, 2H), 6.64 (d, J=8.61 Hz, 2H), 4.00–3.91 (m, 5H), 2.92 (dd, J=4.92, 13.74 Hz, 1H), 2.71 (dd, J=9.89, 13.74 Hz, 1H), 2.49 (s, 3H), 2.06 (quintet, J=6.30 Hz, 2H); LRMS (EI) calcd for $C_{20}H_{25}ClN_4O_6S$ 485.1 (M+H), found 485.3.

EXAMPLE 82

(2S)-3-{4-[3-(Amidinoaminooxy)propoxy]phenyl}-2-({[4-(2-chloro-6-nitrophenoxy)phenyl]sulfonyl}amino)propanoic acid trifluoroacetic acid salt

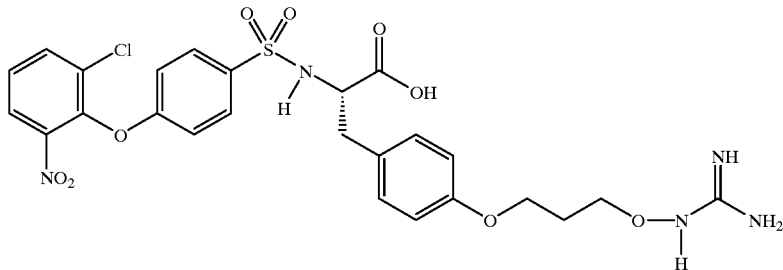

¹H NMR (400 MHz, DMSO-d₆) δ11.17 (s, 1H), 8.24 (d, J=8.86 Hz, 1H), 8.18 (dd, J=1.49, 8.29 Hz, 1H), 8.08 (dd, J=1.49, 8.21 Hz, 1H), 7.74 (br s, 4H), 7.64 (t, J=8.24 Hz, 1H), 7.58 (d, J=8.93 Hz, 2H), 7.02 (d, J=8.63 Hz, 2H), 6.97 (d J=8.93 Hz, 2H), 6.79 (d, J=8.63 Hz, 2H), 4.01 (t, J=6.28 Hz, 2H), 3.95 (t, J=6.43 Hz, 2H), 3.79 (dt, J=5.94, 8.69 Hz, 1H), 2.88 (dd, J=5.94, 13.79 Hz, 1H), 2.63 (dd, J=8.69, 13.79 Hz, 1H), 2.05 (quintet, J=6.35 Hz, 2H); LRMS (EI) calcd for $C_{25}H_{26}ClN_5O_9S$ 608.1 (M+H), found 608.4.

EXAMPLE 83

(2S)-2-{[(1R)-10-Camphorsulfonyl]amino}-3-{4-[3-(amidinoaminooxy)propoxy]phenyl}propanoic acid trifluoroacetic acid salt

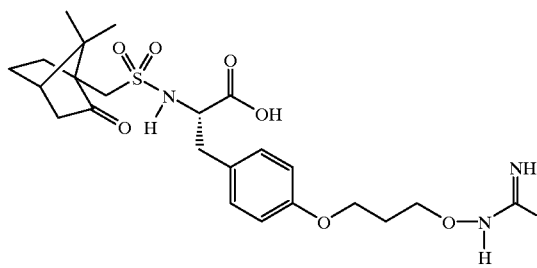

¹H NMR (300 MHz, DMSO-d₆) δ11.24 (s, 1H), 8.25 (br s, 1H), 7.78 (br s, 4H), 7.16 (d, J=8.66 Hz, 2H), 6.90 (d, J=8.66 Hz, 2H), 4.07–3.92 (m, 5H), 3.04–2.88 (m, 2H), 2.70–2.62 (m, 1H), 2.42 (d, J=14.71 Hz, 1H), 2.28–2.20 (m, 2H), 2.10–1.94 (m, 3H), 1.92–1.81 (m, 2H), 1.38–1.23 (m, 2H), 1.04 (s, 3H), 0.74 (s, 3H); LRMS (EI) calcd for $C_{23}H_{34}N_4O_7S$ 511.2 (M+H), found 511.4.

EXAMPLE 84

(2S)-3-{4-[3-(Amidinoaminooxy)propoxy]phenyl}-2-({[(2-nitrophenyl)methyl]sulfonyl}amino)propanoic acid trifluoroacetic acid salt

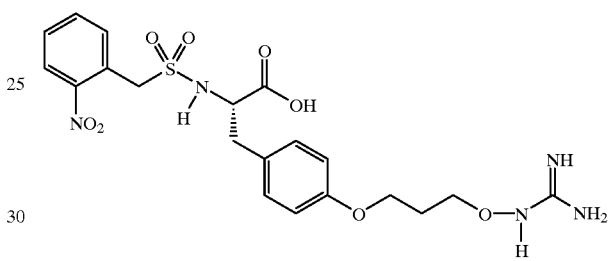

¹H NMR (400 MHz, DMSO-d₆) δ8.07 (m, 1H), 7.98 (d, J=7.97 Hz, 1H), 7.76 (br s, 4H), 7.69–7.58 (m, 2H), 7.37 (d, J=1.24, 7.47 Hz, 1H), 7.19 (d, J=8.59 Hz, 2H), 6.89 (d, J=8.59 Hz, 2H), 4.60 (d, J=13.69 Hz, 1H), 4.49 (d, J=13.69 Hz, 1H), 4.04 (t, J=6.21 Hz, 2H), 3.99–3.91 (m, 3H), 2.97 (dd, J=5.36, 13.75 Hz, 1H), 2.74 (dd, J=9.19, 13.75 Hz, 1H), 2.05 (quintet, J=6.29 Hz, 2H); LRMS (EI) calcd for $C_{20}H_{25}N_5O_8S$ 496.1 (M+H), found 496.5.

EXAMPLE 85

(2S)-3-{4-[3-(Amidinoaminooxy)propoxy]phenyl}-2-({[4-(3-chloro-2-cyanophenoxy)phenyl]sulfonyl}amino)propanoic acid trifluoroacetic acid salt

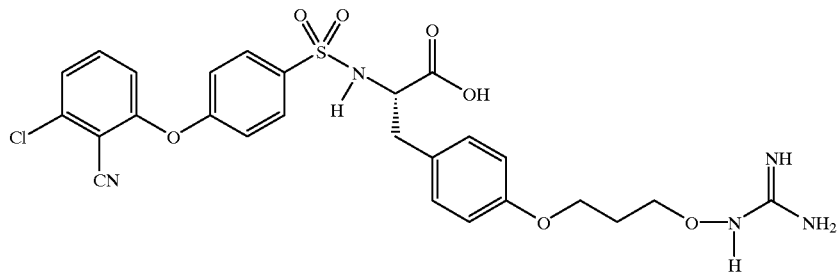

¹H NMR (400 MHz, DMSO-d₆) δ11.11 (s, 1H), 8.33 (d, J=9.11 Hz, 1H), 7.74–7.66 (m, 6H), 7.56 (dd, J=0.58, 8.15 Hz, 1H), 7.23 (d, J=8.84 Hz, 2H), 7.15 (d, J=8.69 Hz, 1H), 7.32 (d, J=8.62 Hz, 2H), 7.04 (dd, J=0.57, 8.56 Hz, 1H), 6.79 (d, J=8.65 Hz, 2H), 4.02 (t, J=6.23 Hz, 2H), 3.94 (t, J=5.31 Hz, 2H), 3.83 (dt, J=5.61, 9.10 Hz, 1H), 2.90 (dd, J=5.49, 13.81 Hz, 1H), 2.67 (dd, J=9.17, 13.81 Hz, 1H), 2.04 (quintet, J=6.34 Hz, 2H); LRMS (EI) calcd for $C_{26}H_{26}ClN_5O_7S$ 588.1 (M+H), found 588.4.

EXAMPLE 86

(2S)-2-{[(1S)-10-Camphorsulfonyl]amino}-3-{4-[3-(amidinoaminooxy)propoxy]phenyl}propanoic acid trifluoroacetic acid salt

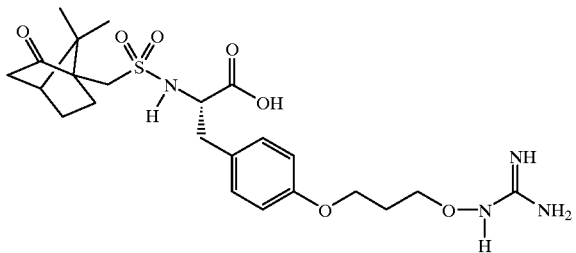

¹H NMR (300 MHz, DMSO-d₆) δ11.13 (s, 1H), 7.73–7.70 (m, 5H), 7.21 (d, J=8.58 Hz, 2H), 6.85 (d, J=8.58 Hz, 2H), 4.03–3.98 (m, 3H), 3.94 (t, J=6.43 Hz, 2H), 2.99 (dd, J=4.80, 13.67 Hz, 1H), 2.84 (d, J=14.91 Hz, 1H), 2.72 (dd, J=9.77, 13.67 Hz, 1H), 2.53 (d, J=14.91 Hz, 1H), 2.30–2.14 (m, 2H), 2.07–1.98 (m, 3H), 1.91–1.82 (m, 2H), 1.45–1.41 (m, 2H), 0.88 (s, 3H), 0.64 (s, 3H); LRMS (EI) calcd for $C_{23}H_{34}N_4O_7S$ 511.2 (M+H), found 511.4.

EXAMPLE 87

(2S)-3-{4-[3-(Amidinoaminooxy)propoxy]phenyl}-2-{[(5-bromo(2-thienyl))sulfonyl]amino}propanoic acid trifluoroacetic acid salt

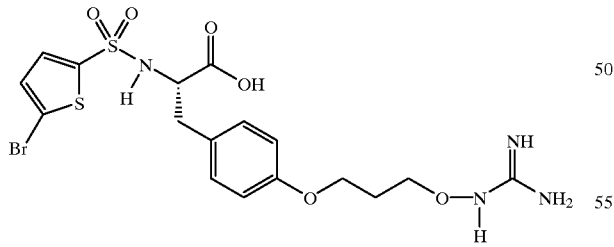

¹H NMR (400 MHz, DMSO-d₆) δ11.25 (s, 1H), 8.67 (d, J=9.01 Hz, 1H), 7.76 (br s, 4H), 7.15 (d, J=3.98 Hz, 1H), 7.14 (d, J=3.98 Hz, 1H), 7.07 (d, J=8.63 Hz, 2H), 6.77 (d, J=8.63 Hz, 2H), 4.04, t, J=6.22 Hz, 2H), 3.97 (t, J=6.49 Hz, 2H), 3.86 (dt, J=4.81, 9.35 Hz, 1H), 3.18 (dd, J=4.81, 13.82 Hz, 1H), 2.65 (dd, J=9.88, 13.82 Hz, 1H), 2.08 (quintet, J=6.33 Hz, 2H); LRMS (EI) calcd for $C_{17}H_{21}BrN_4O_6S_2$ 521.0 (M+H), found 523.1.

EXAMPLE 88

(2S)-3-{4-[3-(Amidinoaminooxy)propoxy]phenyl}-2-{[2,4-dichlorophenyl)sulfonyl]amino}propanoic acid trifluoroacetic acid salt

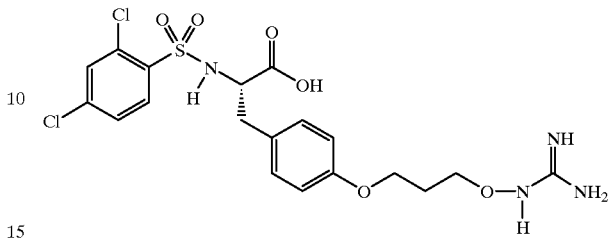

¹H NMR (300 MHz, DMSO-d₆) δ11.17 (s, 1H), 8.54 (d, J=9.08Hz, 1H), 7.74 (br s, 4H), 7.67 (d, J=8.54 Hz, 1H), 7.58 (d, J=2.07 H, 1H), 7.43 (dd, J=2.07, 8.54 Hz, 1H), 7.02 (d, J=8.64 Hz, 2H), 6.67 (d, J=8.64 Hz, 2H), 4.02–3.94 (m, 4H), 3.86 (dt, J=4.30, 9.80 Hz, 1H), 2.93 (dd, J=4.30, 13.84 Hz, 1H), 2.69 (dd, J=10.49, 13.84 Hz, 1H), 2.07 (quintet, J=6.34 Hz, 2H); LRMS (EI) calcd $C_{19}H_{22}Cl_2N_4O_6S$ 505.1 (M+H), found 505.4.

EXAMPLE 89

(2S)-3-{4-[3-(Amidinoaminooxy)propoxy]phenyl}-2-{[(2,2,5,7,8-pentamethylchroman-6-yl)sulfonyl]amino}propanoic acid trifluoroacetic acid salt

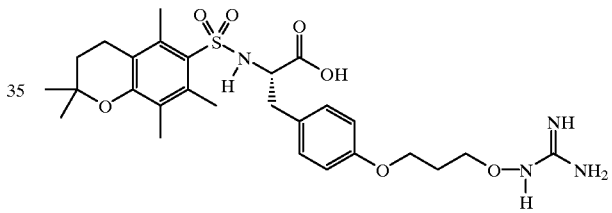

¹H NMR (400 MHz, DMSO-d₆) δ11.17 (s, 1H), 7.85 (d, J=9.42 Hz 1H), 7.73 (br s, 4H), 6.92 (d, J=8.61 Hz, 2H), 6.65 (d, J=8.61 Hz, 2H), 4.00–3.93 (m, 4H), 3.69 (dt, J=5.02, 9.55 Hz, 1H), 2.85 (dd, J=4.87, 13.76 Hz, 1H), 2.66 (dd, J=9.76, 13.76 Hz, 1H), 2.55–2.51 (m, 2H), 2.27 (s, 3H), 2.26 (s, 3H), 2.06 (quintet, J=5.92 Hz, 2H), 1.97 (s, 3H), 1.80–1.76 (m, 2H), 1.27 (s, 6H); LRMS (EI) calcd for $C_{27}H_{38}N_4O_7S$ 563.3 (M+H), found 563.2.

EXAMPLE 90

(2S)-3-{4-[3-(Amidinoaminooxy)propoxy]phenyl}-2-{[(2,6-difluorophenyl)sulfonyl]amino}propanoic acid trifluoroacetic acid salt

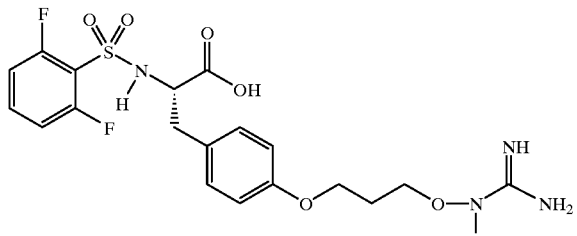

¹H NMR (400 MHz, DMSO-d₆) δ8.75 (d, J=8.33 Hz, 1H), 7.76 (br s, 4H), 7.56 (m, 1H), 7.10–7.06 (m, 4H), 6.70 (d, J=8.57 Hz, 2H), 4.01–3.95 (m, 5H), 2.96 (dd, J=3.83, 13.66 Hz, 1H), 2.70 (dd, J=10.50, 13.66 Hz, 1H), 2.07 (quintet, J=6.29 Hz, 2H); LRMS (EI) calcd for $C_{19}H_{22}F_2N_4O_6S$ 473.1 (M+H), found 473.3.

EXAMPLE 91

(2S)-3-{4-[3-(Amidinoaminooxy)propoxy]phenyl}-2-({[2,5-bis(2,2,2-trifluoroethoxy)phenyl]sulfonyl}amino)propanoic acid trifluoroacetic acid salt

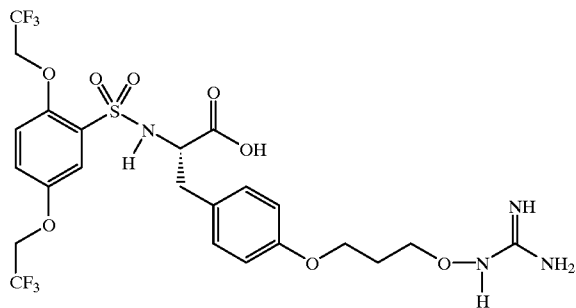

¹H NMR (400 MHz, DMSO-d₆) δ11.13 (s, 1H), 7.72 (br s, 4H), 7.51 (d, J=8.68 Hz, 1H), 7.29–7.26 (m, 2H), 7.20 (d, J=9.96 Hz, 1H), 7.05 (dd, J=8.47 Hz, 2H), 6.75 (d, J=8.47 Hz, 2H), 4.77 (q, J=8.81 Hz, 2H), 4.71 (q, J=8.76 Hz, 2H), 4.06 (m, 1H), 4.01 (t, J=6.04 Hz, 2H), 3.96 (t, J=6.33 Hz, 2H), 2.93 (dd, J=4.51, 13.88 Hz, 1H), 2.76 (dd, J=8.86, 13.88 Hz, 1H), 2.07 (quintet, J=6.27 Hz, 2H); LRMS (EI) calcd for $C_{23}H_{26}F_6N_4O_8S$ 633.1 (M+H), found 633.3.

EXAMPLE 92

(2S)-3-{4-[3-(Amidinoaminooxy)propoxy]phenyl}-2-{[(4-methyl-3-nitrophenyl)sulfonyl]amino}propanoic acid trifluoroacetic acid salt

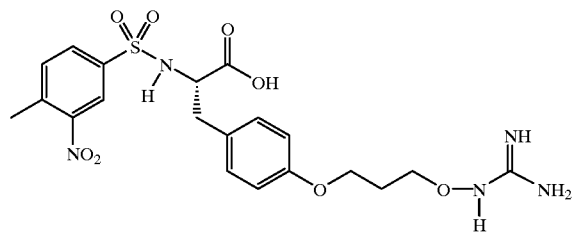

¹H NMR (400 MHz, DMSO-d₆) δ11.14 (s, 1H), 8.59 (d, J=9.10 Hz, 1H), 8.05 (d, J=1.93 Hz, 1H), 7.80 (dd, J=1.68, 7.86 Hz, 1H), 7.72 (br s, 4H), 7.54 (d, J=8.27 Hz, 1H), 7.01 (d, J=8.66 Hz, 2H), 6.66 (d, J=8.66 Hz, 2H), 4.00–3.95 (m, 4H), 3.91 (dt, J=4.62, 9.55 Hz, 1H), 2.91 (dd, J=4.62, 13.84 Hz, 1H), 2.63 (dd, J=10.12, 13.84 Hz, 1H), 2.57 (s, 3H), 2.07 (quintet, J=6.32 Hz, 2H); LRMS (EI) calcd for $C_{20}H_{25}N_5O_8S$ 496.1 (M+H), found 496.4.

EXAMPLE 93

(2S)-3-{4-[3-(Amidinoaminooxy)propoxy]phenyl}-2-({[2-chloro-4-(trifluoromethyl)phenyl]sulfonyl}amino)propanoic acid trifluoroacetic acid salt

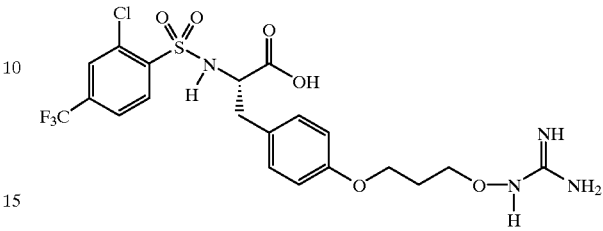

¹H NMR (400 MHz, DMSO-d₆) δ11.13 (s, 1H), 8.74 (d, J=9.06 Hz, 1H), 7.89 (d, J=8.28 Hz, 1H), 7.83 (s, 1H), 7.79–7.68 (m, 5H), 7.03 (d, J=8.27 Hz, 2H), 6.65 (d, J=8.27 Hz, 2H), 4.05–3.89 (m, 5H), 2.96 (dd, J=4.01, 13.73 Hz, 1H), 2.73 (dd J=10.92, 13.73 Hz, 1H), 2.06 (quintet, J=6.21 Hz, 2H); LRMS (EI) calcd for $C_{20}H_{22}ClF_3N_4O_6S$ 539.1 (M+H), found 539.4.

EXAMPLE 94

(2S)-3-{4-[3-(Amidinoaminooxy)propoxy]phenyl}-2-{[(3,4-difluorophenyl)sulfonyl]amino}propanoic acid trifluoroacetic acid salt

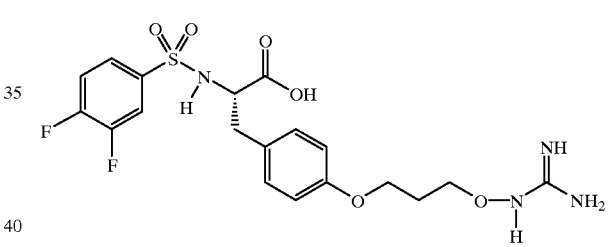

¹H NMR (400 MHz, DMSO-d₆) δ11.17 (s, 1H), 8.48 (d, J=9.12 Hz, 1H), 7.74 (br s, 4H), 7.53–7.37 (m, 3H), 7.03 (d, J=8.57 Hz, 2H), 6.71 (d, J=8.57 Hz, 2H), 4.02–3.95 (m, 4H), 3.87 (dt, J=4.62, 9.59 Hz, 1H), 2.92 (dd, J=4.62, 13.79 Hz, 1H), 2.63 (dd, J=10.17, 13.79 Hz, 1H), 2.07 (quintet, J=6.37 Hz, 2H); LRMS (EI) calcd for $C_{19}H_{22}F_2N_4O_6S$ 473.1 (M+H), found 473.3.

EXAMPLE 95

(2S)-3-{4-[3-(Amidinoaminooxy)propoxy]phenyl}-2-{[(3-chloro-4-methylphenyl)sulfonyl]amino}propanoic acid trifluoroacetic acid salt

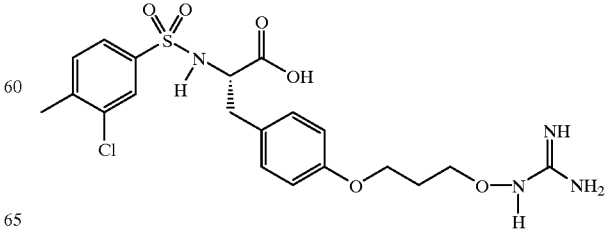

¹H NMR (400 MHz, DMSO-d₆) δ11.20 (s, 1H), 8.38 (d, J=9.07 Hz, 1H), 7.48 (s, 1H), 7.40 (s, 2H), 7.02 (d, J=8.55 Hz, 2H), 6.72 (d, J=8.55 Hz, 2H), 4.01 (t, J=6.33 Hz, 2H), 3.96 (t, J=6.43 Hz, 2H), 3.85 (dt, J=4.99, 9.34 Hz, 1H), 2.89 (dd, J=4.95, 13.81 Hz, 1H), 2.63 (dd, J=9.73, 13.81 Hz, 1H), 2.36 (s, 3H), 2.07 (t, J=6.33 Hz, 2H); LRMS (EI) calcd for $C_{20}H_{25}ClN_4O_6S$ 485.1 (M+H), found 485.3.

EXAMPLE 96

(2S)-3-{4-[3-(Amidinoaminooxy)propoxy]phenyl}-2-{[(5-fluoro-2-methylphenyl)sulfonyl]amino}propanoic acid trifluoroacetic acid salt

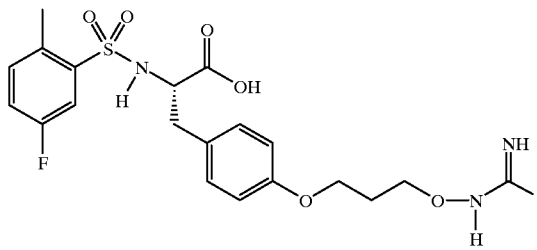

¹H NMR (400 MHz, DMSO-d₆) δ11.20 (s, 1H), 8.46 (d, J=9.30 Hz, 1H), 7.76 (br s, 4H), 7.36–7.15 (m, 3H), 7.01 (d, J=8.53 Hz, 2H), 6.69 (d, J=8.53 Hz, 2H), 7.02–3.96 (m, 4H), 3.80 (dt, J=4.63, 9.72 Hz, 1H), 2.91 (dd, J=4.63, 13.70 Hz, 1H), 2.66 (dd, J=10.36, 13.70 Hz, 1H), 2.51 (s, 3H), 2.08 (quintet, J=6.27 Hz, 2H); LRMS (EI) calcd for $C_{20}H_{25}FN_4O_6S$ 469.2 (M+H), found 469.3.

EXAMPLE 97

(2S)-3-{4-[3-(Amidinoaminooxy)propoxy]phenyl}-2-{[(1-methylimidazol-4-yl)sulfonyl]amino}propanoic acid trifluoroacetic acid salt

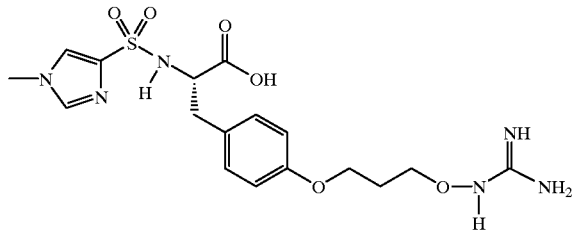

¹H NMR (400 MHz, DMSO-d₆) δ11.40 (s, 1H), 7.88 (br s, 4H), 7.83 (d, J=8.52 Hz, 1H), 7.66 (d, J=1.08 Hz, 1H), 7.35 (d, J=1.08 Hz, 1H), 7.05 (d, J=8.60 Hz, 2H), 6.81 (d, J=8.60 Hz, 2H), 4.03 (t, J=6.23 Hz, 2H), 3.95 (t, J=6.37 Hz, 2H), 3.89 (q, J=7.63 Hz, 1H), 3.62 (s, 3H), 2.85 (dd, J=6.21, 13.74 Hz, 1H), 2.69 (dd, J=8.13, 13.74 Hz, 1H), 2.06 (quintet, J=6.28 Hz, 2H); LRMS (EI) calcd for $C_{17}H_{24}N_6O_6S$ 441.1 (M+H), found 441.3.

EXAMPLE 98

(2S)-3-{4-[3-(Amidinoaminooxy)propoxy]phenyl}-2-{[(4-bromo-2-ethylphenyl)sulfonyl]amino}propanoic acid trifluoroacetic acid salt

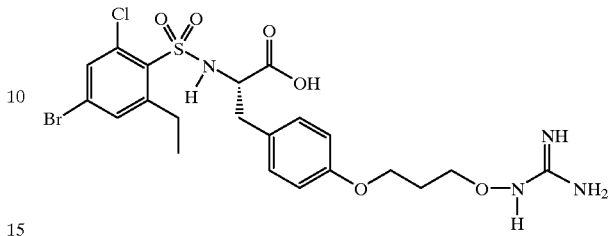

¹H NMR (400 MHz, DMSO-d₆) δ11.15 (s, 1H), 8.45 (d, J=9.26 Hz, 1H), 7.72 (br s, 4H), 7.47 (d, J=9.03 Hz, 1H), 7.40–7.36 (m, 2H), 6.98 (d, J=8.63 Hz, 2H), 6.70 (d, J=8.63 Hz, 2H), 4.03 (t, J=6.33 Hz, 2H), 3.98 (t, J=6.49 Hz, 2H), 3.71 (m, 1H), 2.91–2.82 (m, 2H), 2.69–2.61 (m, 2H), 2.09 (quintet, J=6.39 Hz, 2H), 1.12 (t, J=7.43 Hz, 3H); LRMS (EI) calcd for $C_{21}H_{27}BrN_4O_6S$ 543.1 (M+H), found 545.0.

EXAMPLE 99

(2S)-3-{4-[3-(Amidinoaminooxy)propoxy]phenyl}-2-{[(5-chloro-2-methoxyphenyl)sulfonyl]amino}propanoic acid trifluoroacetic acid salt

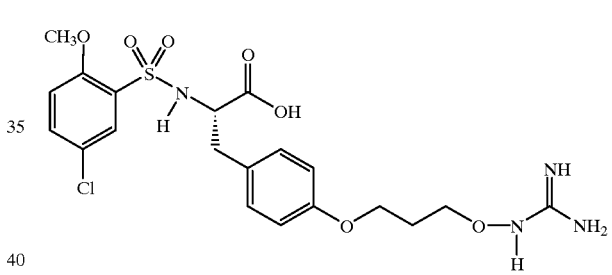

¹H NMR (400 MHz, DMSO-d₆) δ11.20 (s, 1H), 7.93 (d, J=8.85 Hz, 1H), 7.76 (br s, 4H), 7.55 (dt, J=7.81, 2.01 Hz, 1H), 7.49 (t, J=2.01 Hz, 1H), 7.09 (d, J=7.81 Hz, 1H), 7.06 (d, J=7.38 Hz, 2H), 6.74 (d, J=7.38 Hz, 2H), 4.01–3.95 (m, 5H), 3.78 (s, 3H), 2.92 (dd, J=4.50, 13.34 Hz, 1H), 2.72 (dd, J=10.19, 13.34 Hz, 1H), 2.09 (quintet, J=5.9 Hz, 2H); LRMS (EI) calcd for $C_{20}H_{25}ClN_4O_7S$ 501.1 (M+H), found 501.3.

EXAMPLE 100

(2S)-3-{4-[3-(Amidinoaminooxy)propoxy]phenyl}-2-[(benzo[2,3-c]1,2,5-oxadiazol-4-ylsulfonyl)amino]propanoic acid trifluoroacetic acid salt

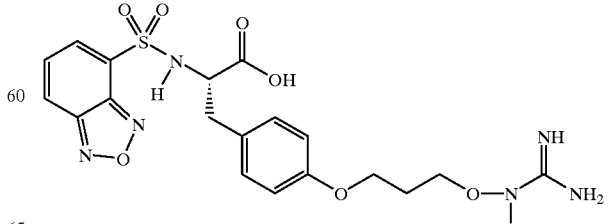

$^1$H NMR (400 MHz, DMSO-d$_6$) δ11.19 (s, 1H), 8.83 (d, J=9.14 Hz, 1H), 8.16 (d, J=9.45 Hz, 1H), 7.80 (d, J=6.76 Hz, 1H), 7.75 (br s, 4H), 7.58 (dd, J=6.76, 9.04 Hz, 1H), 6.86 (d, J=8.55 Hz, 2H), 6.36 (d, J=8.55 Hz, 2H), 4.05 (m, 1H), 4.00 (t, J=6.51 Hz, 2H), 3.91 (t, J=6.22 Hz, 2H), 2.90 (dd, J=3.61, 13.63 Hz, 1H), 2.58 (dd, J=11.45, 13.63 Hz, 1H), 2.08 (quintet, J=6.23 Hz, 2H); LRMS (EI) calcd for C$_{19}$H$_{22}$N$_6$O$_7$S 479.1 (M+H), found 479.4.

EXAMPLE 101

(2S)-3-{4-[3-(Amidinoaminooxy)propoxy]phenyl}-2-{[(4-pentylphenyl)sulfonyl]amino}propanoic acid trifluoroacetic acid salt

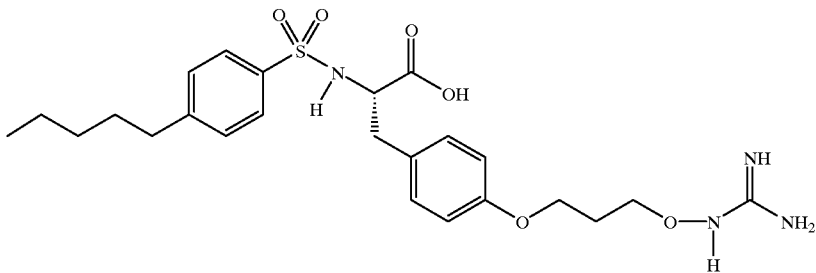

$^1$H NMR (400 MHz, DMSO-d$_6$) δ11.25 (s, 1H), 8.15 (d, J=8.90 Hz 1H), 7.78 (br s, 4H), 7.47 (d, J=8.23 Hz, 2H), 7.24 (d, J=8.23 Hz, 2H), 7.01 (d, J=8.53 Hz, 2H), 6.75 (d, J=8.53 Hz, 2H), 4.03 (t, J=6.23 Hz, 2H), 3.96 (t, J=8.52 Hz, 2H), 3.77 (dt, J=5.73, 8.79 Hz, 1H), 2.85 (dd, J=5.73, 13.78 Hz, 1H), 2.64–2.51 (m, 3H), 2.07 (t, J=6.35 Hz, 2H), 1.60–1.53 (m, 2H), 1.33–1.21 (m, 4H), 0.85 (t,J=6.99 Hz, 3H); LRMS (EI) calcd for C$_{24}$H$_{34}$N$_4$O$_6$S 507.2 (M+H), found 507.3.

EXAMPLE 102

(2S)-3-{4-[3-(Amidinoaminooxy)propoxy]phenyl}-2-{[(4,6-dichloro-2-methylphenyl)sulfonyl]amino}propanoic acid trifluoroacetic acid salt

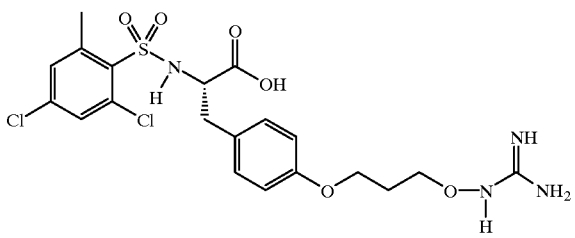

$^1$H NMR (300 MHz, DMSO-d$_6$) δ11.17 (s, 1H), 8.43 (d, J=9.27 Hz, 1H), 7.74 (br s, 4H), 7.40 (d, J=2.21 Hz, 1H), 7.30 (d, J=2.21 Hz, 1H), 7.01 (d, J=8.62 Hz, 2H), 6.62 (d, J=8.62 Hz, 2H), 4.00–3.90 (m, 5H), 2.94 (dd, J=4.39, 13.75 Hz, 1H), 2.68 (dd, J=10.71, 13.75 Hz, 1H), 2.46 (s, 3H), 2.07 (t, J=6.36 Hz, 2H); LRMS (EI) calcd for C$_{20}$H$_{24}$Cl$_2$N$_4$O$_6$S 519.1 (M+H), found 519.4.

EXAMPLE 103

In Vitro Inhibition of Purified Enzymes
Fibrinogen-IIb-IIIa assay

The assay is based on the method of Dennis (Dennis, M. S., et al, *Proteins* 15: 312–321 (1993)). Costar 9018 flat-bottom 96-well ELISA plates were coated overnight at 4° C. with 100 μL/well of 10 μg/mL human fibrinogen (Calbiochem 341578) in 20 mM Tris-HCl pH 7.5, 150 mM NaCl, 2 mM CaCl$_2$, 0.02% NaN$_3$ (TAC buffer), and blocked for 1 hr at 37° C. with 150 μL/well of TAC buffer containing 0.05% Tween 20 and 1% bovine serum albumin (TACTB buffer). After washing 3 times with 200 μL/well of 10 mM Na$_2$HPO$_4$ pH 7.5, 150 mM NaCl, 0.01% Tween 20 (PBST buffer), controls or test compound (0.036–18.2 μM) were mixed with 40 μg/mL human GPIIbIIIa (Enzyme Research Laboratories) in TACTB buffer, and 100 μL/well of these solutions were incubated for 2 hr at 37° C. The plate was then washed 3 times with PBST buffer, and 100 μL/well of a monoclonal anti-GPIIbIIIa antibody in TACTB buffer (1 μg/mL, Enzyme Research Laboratories MabGP2b3a) was incubated at 37° C. for 1 hr. After washing (3 times with PBST buffer), 100 μL/well of goat anti-mouse IgG conjugated to horseradish peroxidase (Kirkegaard & Perry 14-23-06) was incubated at 37° C. for 1 hr (25 ng/mL in PBST buffer), followed by a 5-fold PBST buffer wash. The plate was developed by adding 100 μL/well of 0.67 mg o-phenylenediamine dihydrochloride per mL of 0.012% H$_2$O$_2$, 22 mM sodium citrate, 50 mM sodium phosphate, pH 5.0 at room temperature. The reaction was stopped with 50 μL/well of 2M H$_2$SO$_4$, and the absorbence at 492 nm was recorded. Percent (%) inhibition was calculated from the average of three separate determinations relative to buffer controls (no test compound added), and a four parameter fit (Marquardt, D. W., *J. Soc. Indust. Appl. Math.* 11:431–441 (1963)) was used to estimate the half maximal inhibition concentration (IC$_{50}$). A representative plot for inhibition of the fibrinogen-GPIIbIIIa interaction by the compound of EXAMPLE 1 is shown in FIG. 1.

αvβ3-vitronectin Assay

The assay was based on the method of Niiya (Niiya, K., et al., *Blood* 70:475–483 (1987)). Costar 9018 flat-bottom 96-well ELISA plates were coated overnight at 4° C. with 100 μL/well of 0.4 μg/mL human αvβ3 (Chemicon CC10118) in TS buffer (20 mM Tris-HCl pH 7.5, 150 mM NaCl, 1 mM CaCl$_2$, 1 mM MgCl$_2$, 1 mM MnCl$_2$). All subsequent steps were performed at room temperature. Plates were blocked for 2 hr with 200 μL/well of TS buffer containing 1% BSA (TSB buffer), and washed 5 times with 200 μL/well of TS buffer. Controls or test compound (0.44–455 nM) were mixed with 1 μg/mL of human vitronectin (Chemicon CC1019) that had been biotinylated in-house with sulfo-NHS-LC-LC-biotin (Pierce 21338, 20:1 molar ratio), and 100 μL/well of these solutions (in TSB buffer) were incubated for 2 hr. The plate was then washed 5 times with TS buffer, and 100 μL/well of 1 μ/mL NeutrAvidin-horseradish peroxidase conjugate (Pierce 31001) in TSB buffer was incubated for 1 hr. Following a 5-fold TS buffer wash, the plate was developed and results were calculated as described for the fibrinogen-IIbIIIa assay. A representative plot for inhibition of the αvβ3-vitronectin interaction by the compound of Example 1 is shown in FIG. 2. $IC_{50}$ values for inhibition of the αvβ3-vitronectin interaction by other compounds of the invention are presented in Table I.

TABLE I

Inhibition of the αvβ3-Vitronectin Interaction

| Example No. | αvβ3 $IC_{50}$ (nM) |
|---|---|
| 11 | 2 |
| 77 | 6 |
| 46 | 2 |
| 86 | 1 |

Compounds of the present invention also have αvβ5 activity as determined by the SKBR3 cell-vitronectin (αvβ5-mediated) adhesion assay described by Luna et al. (*Lab. Invest.* 75(4):563–573 (1996)).

FIG. 1: A representative plot for inhibition of the fibrinogen-GPIIbIIIa interaction by the compound of EXAMPLE 1. Values represent the mean of three replicate determinations. $IC_{50}$=780 nM.

FIG. 2: A representative plot for inhibition of the αvβ3-vitronectin interaction by the compound of Example 1. Values represent the mean of three replicate determinations. $IC_{50}$=28 Nm.

EXAMPLE 104

Tablet Preparation

Tablets containing 25.0, 50.0, and 100.0 mg, respectively, of the compound of Example 1 ("active compound") are prepared as illustrated below:

TABLET FOR DOSES CONTAINING FROM 25–100 MG OF THE ACTIVE COMPOUND

| | Amount-mg | | |
|---|---|---|---|
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 105

Intravenous Solution Preparation

An intravenous dosage form of the compound of Example 1 ("active compound") is prepared as follows:

| Active compound | 0.5–10.0 mg |
|---|---|
| Sodium citrate | 5–50 mg |
| Citric acid | 1–15 mg |

-continued

| Sodium chloride | 1–8 mg |
|---|---|
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula IV:

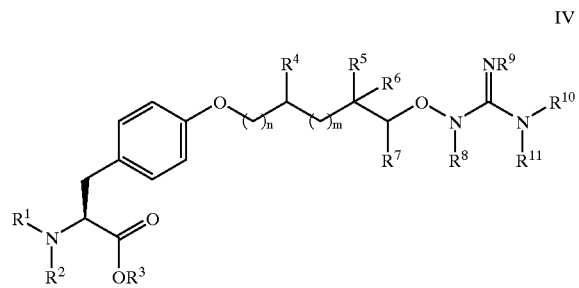

or a pharmaceutically acceptable salt thereof;
   wherein
   $R^1$ and $R^2$ independently represent hydrogen, alkyl, aralkyl, $R^{12}SO_2$, $R^{12}OOC$, or $R^{12}CO$, where $R^{12}$ is (i) hydrogen, or (ii) alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;
   and when $R^1$ or $R^2$ is $R^{12}CO$, then $R^{12}$ can also be N-attached pyrrolidinyl, piperidinyl or morpholinyl;
   $R^3$ is hydrogen or a functionality which acts as a prodrug;
   $R^4$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di-alkylamino;
   $R^5$, $R^6$, and $R^7$ are independently hydrogen, alkyl, aralkyl, aryl, hydroxyalkyl, aminoalkyl, monoalkylaminoalkyl, dialkylaminoalkyl or carboxyalkyl;
   or $R^4$ and $R^5$ are taken together to form —$(CH_2)_y$—, where y is zero (a bond), 1 or 2, while $R^6$ and $R^7$ are defined as above; or $R^4$ and $R^7$ are taken together to form —$(CH_2)_q$—, where q is zero (a bond), or 1 to 8, while $R^5$ and $R^6$ are defined as above; or $R^5$ and $R^6$ are taken together to form —$(CH_2)_r$—, where r is 2–8, while $R^4$ and $R^7$ are defined as above;

$R^8$ is hydrogen, alkyl, aralkyl, hydroxyalkyl, aminoalkyl, monoalkylaminoalkyl, dialkylaminoalkyl or carboxyalkyl;

$R^9$, $R^{10}$, and $R^{11}$ are independently hydrogen, alkyl, aralkyl, hydroxy, alkoxy, aryloxy, aralkoxy, alkoxycarbonyloxy, cyano or —COOR$^w$;

$R^w$ is alkyl, cycloalkyl, phenyl, benzyl,

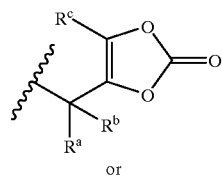

or

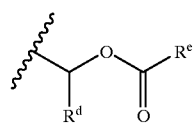

where $R^a$ and $R^b$ are independently hydrogen, alkyl, alkenyl or phenyl; $R^c$ is hydrogen, alkyl, alkenyl or phenyl; $R^d$ is hydrogen, alkyl, alkenyl or phenyl; and $R^e$ is aralkyl or alkyl;

n is from zero to 8; m is from zero to 4; provided that n is other than zero when $R^4$ is hydroxy, alkoxy, aralkoxy, aryloxy, heteroaryloxy, or mono- or di-alkylamino.

2. The compound of claim 1, wherein
$R^1$ and $R^2$ independently represent hydrogen, $C_{1-6}$alkyl, $C_{6-10}$ar($C_{1-6}$)alkyl, $R^{12}SO_2$, $R^{12}OOC$ or $R^{12}CO$, where $R^{12}$ is hydrogen, $C_{1-6}$alkyl, $C_{6-10}$ar($C_{1-6}$) alkyl, $C_{4-7}$cycloalkyl($C_{1-4}$)alkyl, camphor-10-yl, or $C_{6-10}$aryl substituted by one or more ($C_{1-6}$)alkyl, ($C_{2-6}$)alkenyl, $C_{6-10}$ aryl, $C_{6-10}$ ar($C_{1-6}$)alkyl, $C_{6-10}$ aryloxy (further optionally substituted by nitro, halo, or cyano), $C_{6-10}$ aryldiazenyl (further optionally substituted by amino, $C_{1-4}$ alkylamino or di ($C_{1-4}$) alkylamino), $C_{1-6}$ alkoxy, halo($C_{1-6}$)alkyl, halo($C_{1-6}$)alkoxy, $C_{1-6}$ alkylcarbonylamino, $C_{1-6}$ alkylsulfonyl, mono- or di-($C_{1-6}$)alkylamino, hydroxy, carboxy, cyano, nitro, halo, or a heteroaryl which is optionally substituted with one or more $C_{1-6}$ alkyl, halo($C_{1-6}$)alkyl, or halo;

and when $R^1$ or $R^2$ is $R^{12}CO$, then $R^{12}$ can also be N-attached pyrrolidinyl, piperidinyl or morpholinyl;

$R^3$ is one of hydrogen, $C_{1-6}$alkyl or benzyl;

$R^4$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$alkyl)amino($C_{1-8}$)alkyl, or di($C_{1-4}$alkyl)amino($C_{1-8}$)alkyl;

$R^5$, $R^6$ and $R^7$ are independently hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl;

$R^8$ is hydrogen or $C_{1-6}$ alkyl;

$R^9$, $R^{10}$ and $R^{11}$ are independently hydrogen, hydroxy, $C_{1-6}$ alkyl, $C_{1-6}$ alkoxy, cyano or —CO$_2$R$^w$, where R$^w$, in each instance, is one of $C_{1-4}$alkyl, $C_{4-7}$cycloalkyl, phenyl, or benzyl;

n is zero to 4; and
m is zero to 4.

3. The compound of claim 1, wherein
$R^1$ is hydrogen or methyl;
$R^2$ is hydrogen, t-butylcarbonyl, butylsulfonyl, propylsulfonyl, benzylsulfonyl, pentylsulfonyl, 4-tolylsulfonyl, or camphor-10-sulfonyl;

$R^3$ is hydrogen or $C_{1-6}$alkyl;
$R^4$ is methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl or 2-(dimethylamino)ethyl;

$R^5$, $R^6$ and $R^7$ independently represent hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl or 4-carboxypropyl;

$R^8$ is hydrogen or $C_{1-6}$ alkyl;
$R^9$, $R^{10}$ and $R^{11}$ are each hydrogen;
n is zero, 1, or 2; and
m is zero, 1, or 2.

4. The compound of claim 1, wherein
$R^3$ is hydrogen, alkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl.

5. The compound of claim 1, wherein
$R^2$ is $R^{12}SO_2$, where $R^{12}$ is hydrogen, alkyl, cycloalkyl, camphor-10-yl, alkenyl, alkynyl, heterocycle, aryl, aralkyl, or aralkenyl, any of which can be optionally substituted by one or more alkyl, alkenyl, aryl, aryloxy (further optionally substituted by nitro, halo, or cyano), aralkyl, aryldiazenyl (further optionally substituted by amino, alkylamino, or dialkylamino), alkoxy, haloalkyl, haloalkoxy, alkylcarbonylamino, alkylsulfonyl, mono- or di-alkylamino, hydroxy, carboxy, cyano, nitro, halo, or a heteroaryl which is optionally substituted with one or more alkyl, haloalkyl, or halo;

$R^1$ is hydrogen;
$R^3$, $R^4$, $R^5$, $R^6$ and $R^7$ are each hydrogen;
$R^8$, $R^9$, $R^{10}$ and $R^{11}$ are each hydrogen;
n is zero; and
m is zero.

6. The compound of claim 5, wherein
$R^2$ is $R^{12}SO_2$, where $R^{12}$ is hydrogen, $C_{1-6}$alkyl, $C_{4-7}$cycloalkyl, camphor-10-yl, ($C_{2-6}$)alkenyl, ($C_{2-6}$) alkynyl, thienyl, thiazolyl, benzo[b]thiophenyl, pyrazolyl, chromanyl, imidazolyl, benzo[2,3-c]1,2,5-oxadiazole, $C_{6-10}$ aryl, $C_{6-10}$ar($C_{1-6}$)alkyl, or $C_{6-10}$ ar($C_{2-6}$)alkenyl, any of which can be optionally substituted by one or more $C_{1-6}$ alkyl, $C_{2-6}$ alkenyl, $C_{6-10}$ aryl, $C_{6-10}$ aryloxy (further optionally substituted by nitro, halo, or cyano), $C_{6-10}$ ar($C_{1-6}$)alkyl, 4-dimethylaminophenyldiazenyl, $C_{1-6}$alkoxy, halo($C_{1-6}$)alkyl, halo($C_{1-6}$)alkoxy, $C_{1-6}$alkylcarbonylamino, $C_{1-6}$ alkylsulfonyl, mono- or di-($C_{1-6}$)alkylamino, hydroxy, carboxy, cyano, nitro, halo, or pyrazolyl which is optionally substituted with one or more $C_{1-6}$alkyl, halo($C_{1-6}$)alkyl, or halo.

7. The compound of claim 1, wherein $R^3$ is hydrogen, $C_{1-6}$alkyl, or benzyl.

8. The compound of claim 1, wherein $R^4$ is hydrogen, $C_{1-6}$alkyl, $C_{6-10}$ar($C_{1-6}$)alkyl, $C_{6-10}$aryl, $C_{2-10}$hydroxyalkyl, $C_{2-10}$aminoalkyl, $C_{2-7}$carboxyalkyl, mono($C_{1-4}$alkyl)amino ($C_{1-8}$)alkyl, or di($C_{1-4}$alkyl)amino($C_{1-8}$)alkyl.

9. The compound of claim 8, wherein $R^4$ is methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl or 2-(dimethylamino)ethyl.

10. The compound of claim 1, wherein $R^5$, $R^6$ and $R^7$ are independently hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$carboxyalkyl.

11. The compound of claim 10, wherein $R^5$, $R^6$, and $R^7$ are independently hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

12. The compound of claim 10, wherein $R^5$, $R^6$ and $R^7$ are each hydrogen.

13. The compound of claim 1, wherein $R^8$ is hydrogen or $C_{1-6}$alkyl.

14. The compound of claim 1, wherein $R^9$, $R^{10}$ and $R^{11}$ are independently hydrogen, hydroxy, $C_{1-6}$alkyl, $C_{1-6}$alkoxy, cyano or —$CO_2R^w$, where $R^w$, in each instance, is one of $C_{1-4}$alkyl, $C_{4-7}$cycloalkyl, phenyl, or benzyl.

15. The compound of claim 14, wherein $R^9$, $R^{10}$ and $R^{11}$ are independently hydrogen, methyl, ethyl, propyl, n-butyl, hydroxy, methoxy, ethoxy, cyano, —$CO_2CH_3$, —$CO_2CH_2CH_3$ or —$CO_2CH_2CH_2CH_3$.

16. The compound of claim 14, wherein $R^9$, $R^{10}$ and $R^{11}$ are each hydrogen.

17. The compound of claim 1, wherein n is zero to 6, and m is zero to 4.

18. The compound of claim 17, wherein n is zero, 1, or 2; and
m is zero, 1 or 2.

19. The compound of claim 1, which is one of:
(2S)-3-{4-[3-(Amidinoaminooxy)propoxy]phenyl}-2-[(naphthylsulfonyl)amino]propanoic acid;
(2S)-3-{4-[3-(Amidinoaminooxy)propoxy]phenyl}-2-{[(4-{[4-(dimethylamino)phenyl]diazenyl}-phenyl)sulfonyl]amino}propanoic acid;
2-{[((1E)-2-Phenylvinyl)sulfonyl]amino}-(2S)-3-{4-[3-(amidinoaminooxy)propoxy]-phenyl}propanoic acid;
(2S)-3-{4-[3-(Amidinoaminooxy)propoxy]phenyl}-2-{[(4-ethylphenyl)sulfonyl]-amino}propanoic acid;
(2S)-3-{4-[3-(Amidinoaminooxy)propoxy]phenyl}-2-{[(5-chloro(2-thienyl))sulfonyl]amino}-propanoic acid;
(2S)-3-{4-[3-(Amidinoaminooxy)propoxy]phenyl}-2-{[(3-bromo-5-chloro(2-thienyl))sulfonyl]-amino}propanoic acid;
(2S)-3-{4-[3-(Amidinoaminooxy)propoxy]phenyl}-2-{[(3,5-dichloro-2-hydroxyphenyl)sulfonyl]-amino}propanoic acid;
(2S)-3-{4-[3-(Amidinoaminooxy)propoxy]phenyl}-2-{[(4-nitrophenyl)sulfonyl]amino}-propanoic acid;
(2S)-3-{4-[3-(Amidinoaminooxy)propoxy]phenyl}-2-{[(4-propylphenyl)sulfonyl]-amino}propanoic acid;
(2S)-3-{4-[3-(Amidinoaminooxy)propoxy]phenyl}-2-{[(2-methyl-5-nitrophenyl)sulfonyl]amino}propanoic acid;
(2S)-3-{4-[3-(Amidinoaminooxy)propoxy]phenyl}-2-[(2-naphthylsulfonyl)amino]propanoic acid;
(2S)-3-{4-[3-(Amidinoaminooxy)propoxy]phenyl}-2-({[2,4,6-tris(methyethyl)phenyl]sulfonyl}amino)propanoic acid;
(2S)-3-{4-[3-(Amidinoaminooxy)propoxy]phenyl}-2-{[(4-methoxyphenyl)sulfonyl]amino}propanoic acid;
(2S)-3-{4-[3-(Amidinoaminooxy)propoxy]phenyl}-2-({[4-(1,1-dimethylpropyl)phenyl]sulfonyl}amino)propanoic acid;
(2S)-3-{4-[3-(Amidinoaminooxy)propoxy]phenyl}-2-({[2-(trifluoromethyl)phenyl]sulfonyl}amino)-propanoic acid;
(2S)-2-({[2-(Acetylamino)-4-methyl(1,3-thiazol-5-yl)]sulfonyl}amino)-3-{4-[3-(amidino-aminooxy)propoxyl]phenyl}propanoic acid;
(2S)-3-{4-[3-(Amidinoaminooxy)propoxy]phenyl}-2-{[(2,4,6-trimethylphenyl)sulfonyl]amino}propanoic acid;
(2S)-3-{4-[3-(Amidinoaminooxy)propoxy]phenyl}-2-{[(2,3,4-trichlorophenyl)-sulfonyl]amino}propanoic acid;
(2S)-3-{4-[3-(Amidinoaminooxy)propoxy]phenyl}-2-{[(4-bromo-2,5-difluorophenyl)-sulfonyl]amino}propanoic acid;
(2S)-3-{4-[3-(Amidinoaminooxy)propoxy]phenyl}-2-{[(3-chlorophenyl)sulfonyl]-amino}propanoic acid;
(2S)-3-{4-[3-(Amidinoaminooxy)propoxy]phenyl}-2-{[(3-chloro-2-methylphenyl)-sulfonyl]amino}propanoic acid;
(2S)-3-{4-[3-(Amidinoaminooxy)propoxy]phenyl}-2-[(3-thienylsulfonyl)-amino]propanoic acid;
(2S)-3-{4-[3-(Amidinoaminooxy)propoxy]phenyl}-2-{[(3-nitrophenyl)sulfonyl]amino}-propanoic acid;
(2S)-3-{4-[3-(Amidinoaminooxy)propoxy]phenyl}-2-({[4-(tert-butyl)phenyl]sulfonyl}-amino)propanoic acid;
(2S)-3-{4-[3-(Amidinoaminooxy)propoxy]phenyl}-2-{[(2,5-dimethoxyphenyl)sulfonyl]-amino}propanoic acid;
(2S)-3-{4-[3-(Amidinoaminooxy)propoxy]phenyl}-2-{[(2-fluorophenyl)sulfonyl]-amino}propanoic acid;
(2S)-3-{4-[3-(Amidinoaminooxy)propoxy]phenyl}-2-{[(3,5-dichlorophenyl)sulfonyl]-amino}propanoic acid;
(2S)-3-{4-[3-(Amidinoaminooxy)propoxy]phenyl}-2-[({5-[1-methyl-5-(trifluoromethyl)-pyrazol-3-yl](2-thienyl)}sulfonyl)amino]propanoic acid;
(2S)-3-{4-[3-(Amidinoaminooxy)propoxy]phenyl}-2-{[(4-bromophenyl)sulfonyl]-amino}propanoic acid;
(2S)-3-{4-[3-(Amidinoaminooxy)propoxy]phenyl}-2-{[(4-methylphenyl)sulfonyl]-amino}propanoic acid;
(2S)-3-{4-[3-(Amidinoaminooxy)propoxy]phenyl}-2-{[(3-chloropropyl)sulfonyl]-amino}propanoic acid;
2S)-3-{4-[3-(Amidinoaminooxy)propoxy]phenyl}-2-{[(2-methylphenyl)sulfonyl]-amino}propanoic acid;
(2S)-3-{4-[3-(Amidinoaminooxy)propoxy]phenyl}-2-{[(3-fluorophenyl)sulfonyl]-amino}propanoic acid;
(2S)-3-{4-[3-(Amidinoaminooxy)propoxy]phenyl}-2-{[(3-methylphenyl)sulfonyl]-amino}propanoic acid;
(2S)-3-{4-[3-(Amidinoaminooxy)propoxy]phenyl}-2-[(phenylsulfonyl)amino]propanoic acid;
(2S)-3-{4-[3-(Amidinoaminooxy)propoxy]phenyl}-2-{[(4-fluorophenyl)sulfonyl]-amino}propanoic acid;
(2S)-3-{4-[3-(Amidinoaminooxy)propoxy]phenyl}-2-{[(2,5-dimethylphenyl)sulfonyl]amino}propanoic acid;
(2S)-3-{4-[3-(Amidinoaminooxy)propoxy]phenyl}-2-({[(4-trifluoromethoxy)phenyl]sulfonyl}amino)propanoic acid;
(2S)-3-{4-[3-(Amidinoaminooxy)propoxy]phenyl}-2-{[(5-bromo-2-methoxyphenyl)-sulfonyl]amino}propanoic acid;
(2S)-3-{4-[3-(Amidinoaminooxy)propoxy]phenyl}-2-({[2-chloro-5-(trifluoromethyl)-phenyl]sulfonyl}amino)propanoic acid;
(2S)-3-{4-[3-(Amidinoaminooxy)propoxy]phenyl}-2-{[(4-chlorophenyl)sulfonyl]-amino}propanoic acid;
3-{[((1S)-2-{4-[3-Amidinoaminooxy)propoxyl]phenyl}-1-carboxyethyl)amino]sulfonyl}benzoic acid;
(2S)-3-{4-[3-(Amidinoaminooxy)propoxy]phenyl}-2-{[(4-chloro-2,5-dimethylphenyl)-sulfonyl]amino}propanoic acid;
(2S)-3-{4-[3-(Amidinoaminooxy)propoxy]phenyl}-2-{[(3,4-dimethoxyphenyl)-sulfonyl]amino}propanoic acid;
(2S)-3-{4-[3-(Amidinoaminooxy)propoxy]phenyl}-2-{[(2,6-dichlorophenyl)sulfonyl]amino}propanoic acid;
(2S)-3-{4-[3-(Amidinoaminooxy)propoxy]phenyl}-2-{[(2,4,5-trichlorophenyl)sulfonyl]-amino}propanoic acid;
(2S)-3-{4-[3-(Amidinoaminooxy)propoxy]phenyl}-2-{[(4-chloro-3-nitrophenyl)-sulfonyl]amino}propanoic acid;
(2S)-3-{4-[3-(Amidinoaminooxy)propoxy]phenyl}-2-{[(4methoxy-2,3,6-trimethyl-phenyl)sulfonyl]amino}propanoic acid;
(2S)-3-{4-[3-(Amidinoaminooxy)propoxy]phenyl}-2-{[(2-chlorophenyl)sulfonyl]amino}propanoic acid;

(2S)-3-{4-[3-(Amidinoaminooxy)propoxy]phenyl}-2-{[(2,3-dichlorophenyl)-sulfonyl]amino}propanoic acid;
(2S)-3-{4-[3-(Amidinoaminooxy)propoxy]phenyl}-2-{[(3-bromophenyl)sulfonyl]-amino}propanoic acid;
(2S)-3-{4-[3-(Amidinoaminooxy)propoxy]phenyl}-2-{[(2,5-dichlorophenyl)sulfonyl]amino}propanoic acid;
(2S)-3-{4-[3-(Amidinoaminooxy)propoxy]phenyl}-2-{[(4-iodophenyl)sulfonyl]-amino}propanoic acid;
(2S)-3-{4-[3-(Amidinoaminooxy)propoxy]phenyl}-2-[(methylsulfonyl)amino]propanoic acid;
(2S)-3-{4-[3-(Amidinoaminooxy)propoxy]phenyl}-2-{[(2,3,4,5,6-pentamethylphenyl)-sulfonyl]amino}propanoic acid;
(2S)-3-{4-[3-(Amidinoaminooxy)propoxy]phenyl}-2-{[(3,4-dichlorophenyl)-sulfonyl]amino}propanoic acid;
(2S)-3-{4-[3-(Amidinoaminooxy)propoxy]phenyl}-2-{[(4-bromo-2,5-dichloro(3-thienyl))sulfonyl]amino}propanoic acid;
(2S)-3-{4-[3-(Amidinoaminooxy)propoxy]phenyl}-2-{[(2-bromophenyl)sulfonyl]-amino}propanoic acid;
(2S)-3-{4-[3-(Amidinoaminooxy)propoxy]phenyl}-2-({[(2-trifluoromethoxy)-phenyl]sulfonyl}amino)propanoic acid;
(2S)-3-{4-[3-(Amidinoaminooxy)propoxy]phenyl}-2-{[(2-nitrophenyl)sulfonyl]-amino}propanoic acid;
(2S)-2-({[4-Acetylamino)phenyl]sulfonyl}amino)-3-{4-[3-(amidinoaminooxy)propoxy]phenyl}propanoic acid;
(2S)-3-{4-[3-(Amidinoaminooxy)propoxy]phenyl}-2-{[2-benzylsulfonyl]-amino}propanoic acid;
(2S)-3-{4-[3-(Amidinoaminooxy)propoxy]phenyl}-2-({[(3-(trifluoromethyl)phenyl]-sulfonyl}amino)propanoic acid;
(2S)-3-{4-[3-(Amidinoaminooxy)propoxy]phenyl}-2-{[(4,5-dibromo(2-thienyl))sulfonyl]amino}propanoic acid;
(2S)-3-{4-[3-(Amidinoaminooxy)propoxy]phenyl}-2-{[(2,5-dichloro(3-thienyl))sulfonyl]amino}propanoic acid;
(2S)-3-{4-[3-(Amidinoaminooxy)propoxy]phenyl}-2-{[(4-bromo-5-chloro(2-thienyl))sulfonyl]amino}propanoic acid;
(2S)-3-{4-[3-(Amidinoaminooxy)propoxy]phenyl}-2-{[(2-cyanophenyl)sulfonyl]-amino}propanoic acid;
(2S)-3-{4-[3-(Amidinoaminooxy)propoxy]phenyl}-2-{[(2,4,6-trichlorophenyl)-sulfonyl]amino}propanoic acid;
(2S)-3-{4-[3-(Amidinoaminooxy)propoxy]phenyl}-2-{[(5-chloro-3-methylbenzo[b]thiophen-2-yl)sulfonyl]amino}propanoic acid;
(2S)-3-{4-[3-(Amidinoaminooxy)propoxy]phenyl}-2-({[(4-(methylsulfonyl)phenyl]-sulfonyl}amino)propanoic acid;
(2S)-3-{4-[3-(Amidinoaminooxy)propoxy]phenyl}-2-{[(4-butoxyphenyl)sulfonyl]amino}propanoic acid;
(2S)-3-{4-[3-(Amidinoaminooxy)propoxy]phenyl}-2-{[(4-butylphenyl)sulfonyl]amino}propanoic acid;
(2S)-3-{4-[3-(Amidinoaminooxy)propoxy]phenyl}-2-{[(2-methoxy-5-methylphenyl)sulfonyl]amino}propanoic acid;
(2S)-3-{4-[3-(Amidinoaminooxy)propoxy]phenyl}-2-{[(4-phenylphenyl)sulfonyl]amino}propanoic acid;
(2S)-3-{4-[3-(Amidinoaminooxy)propoxy]phenyl}-2-{[(4-bromo-2-methylphenyl)sulfonyl]amino}propanoic acid;
(2S)-3-{4-[3-(Amidinoaminooxy)propoxy]phenyl}-2-{[(5-chloro-1,3-dimethylpyrazol-4-yl)-sulfonyl]amino}propanoic acid;
(2S)-3-{4-[3-(Amidinoaminooxy)propoxy]phenyl}-2-{[(3,4-dibromophenyl)sulfonyl]-amino}propanoic acid;
(2S)-3-{4-[3-(Amidinoaminooxy)propoxy]phenyl}-2-{[(4-vinylphenyl)sulfonyl]-amino}propanoic acid;
(2S)-3-{4-[3-(Amidinoaminooxy)propoxy]phenyl}-2-({[4-bromo-2-(trifluoromethoxy)-phenyl]sulfonyl}amino)propanoic acid;
(2S)-3-{4-[3-(Amidinoaminooxy)propoxy]phenyl}-2-{[(6-chloro-2-methylphenyl)sulfonyl]amino}propanoic acid;
(2S)-3-{4-[3-(Amidinoaminooxy)propoxy]phenyl}-2-({[4-(2-chloro-6-nitrophenoxy)phenyl]sulfonyl}amino) propanoic acid;
(2S)-2-{[(1R)-10-Camphorsulfonyl]amino}-3-{4-[3-(amidinoaminooxy)propoxy]phenyl}propanoic acid;
(2S)-3-{4-[3-(Amidinoaminooxy)propoxy]phenyl}-2-({[(2-nitrophenyl)methyl]sulfonyl}amino)propanoic acid;
(2S)-3-{4-[3-(Amidinoaminooxy)propoxy]phenyl}-2-({[4-(3-chloro-2-cyanophenoxy)phenyl]sulfonyl}amino) propanoic acid;
(2S)-2-{[(1S)-10-Camphorsulfonyl]amino}-3-{4-[3-(amidinoaminooxy)propoxy]phenyl}propanoic acid;
(2S)-3-{4-[3-(Amidinoaminooxy)propoxy]phenyl}-2-{[(5-bromo(2-thienyl))sulfonyl]amino}propanoic acid;
(2S)-3-{4-[3-(Amidinoaminooxy)propoxy]phenyl}-2-{[(2,4-dichlorophenyl)sulfonyl]amino}-propanoic acid;
(2S)-3-{4-[3-(Amidinoaminooxy)propoxy]phenyl}-2-{[(2,2,5,7,8-pentamethyl-chroman-6-yl)sulfonyl]-amino}propanoic acid;
(2S)-3-{4-[3-(Amidinoaminooxy)propoxy]phenyl}-2-{[(2,6-difluorophenyl)sulfonyl]-amino}propanoic acid;
(2S)-3-{4-[3-(Amidinoaminooxy)propoxy]phenyl}-2-({[2,5-bis(2,2,2-trifluoroethoxy)phenyl]sulfonyl}amino) propanoic acid;
(2S)-3-{4-[3-(Amidinoaminooxy)propoxy]phenyl}-2-{[(4-methyl-3-nitrophenyl)sulfonyl]amino}propanoic acid;
(2S)-3-{4-[3-(Amidinoaminooxy)propoxy]phenyl}-2-({[2-chloro-4-(trifluoromethyl)phenyl]-sulfonyl}amino) propanoic acid;
(2S)-3-{4-[3-(Amidinoaminooxy)propoxy]phenyl}-2-{[(3,4-difluorophenyl)sulfonyl]-amino}propanoic acid;
(2S)-3-{4-[3-(Amidinoaminooxy)propoxy]phenyl}-2-{[(3-chloro-4-methylphenyl)sulfonyl]amino}propanoic acid;
(2S)-3-{4-[3-(Amidinoaminooxy)propoxy]phenyl}-2-{[(5-fluoro-2-methylphenyl)sulfonyl]amino}-propanoic acid;
(2S)-3-{4-[3-(Amidinoaminooxy)propoxy]phenyl}-2-{[(1-methylimidazol-4-yl)sulfonyl]amino}propanoic acid;
(2S)-3-{4-[3-(Amidinoaminooxy)propoxy]phenyl}-2-{[(4-bromo-2-ethylphenyl)sulfonyl]amino}propanoic acid;
(2S)-3-{4-[3-(Amidinoaminooxy)propoxy]phenyl}-2-{[(5-chloro-2-methoxyphenyl)sulfonyl]-amino}propanoic acid;
(2S)-3-{4-[3-(Amidinoaminooxy)propoxy]phenyl}-2-[(benzo[2,3-c]1,2,5-oxadiazol-4-ylsulfonyl)amino] propanoic acid;
(2S)-3-{4-[3-(Amidinoaminooxy)propoxy]phenyl}-2-{[(4-pentylphenyl)sulfonyl]-amino}propanoic acid;
(2S)-3-{4-[3-(Amidinoaminooxy)propoxy]phenyl}-2-{[(4,6-dichloro-2-methylphenyl)sulfonyl]-amino}propanoic acid;
or a pharmaceutically acceptable salt, hydrate, solvate or prodrug thereof.

20. The compound of claim 1, which is one of:
(2S)-3-{4-[3-(Amidinoaminooxy)propoxy]phenyl}-2-{[(2,5-dimethylphenyl)sulfonyl]amino}propanoic acid;
(2S)-3-{4-[3-(Amidinoaminooxy)propoxy]phenyl}-2-{[(2,6-dichlorophenyl)sulfonyl]amino}propanoic acid;
(2S)-2-{[(1S)-10-Camphorsulfonyl]amino}-3-{4-[3-(amidinoaminooxy)propoxy]phenyl}propanoic acid;
(2S)-3-{4-[3-(Amidinoaminooxy)propoxy]phenyl}-2-{[(2,4,6-trichlorophenyl)sulfonyl]amino}propanoic acid;
(2S)-3-{4-[3-(Amidinoaminooxy)propoxy]phenyl}-2-{[(5-chloro-1,3-dimethylpyrazol-4yl)sulfonyl] amino}propanoic acid;
or a pharmaceutically acceptable salt, hydrate, solvate or prodrug thereof.

21. A pharmaceutical composition comprising a compound of claim 1 and a pharmaceutically acceptable carrier or diluent.

22. A method of treating αvβ3 integrin- and αvβ5 integrin-mediated pathological conditions selected from the group consisting of tumor growth, metastasis, osteoporosis, restenosis, inflammation, macular degeneration, diabetic retinopathy, and rheumatoid arthritis, in a mammal in need of such treatment, comprising administering to said mammal an effective amount of a compound of claim 1.

23. A method of treating αvβ3 integrin-mediated tumor growth or αvβ5 integrin-mediated tumor growth in a mammal in need of such treatment, comprising administering to said mammal an effective amount of a compound of claim 1.

24. A method of treating αvβ3 integrin-mediated osteoporosis or αvβ5 integrin-mediated osteoporosis in a mammal in need of such treatment, comprising administering to said mammal an effective amount of a compound of claim 1.

25. A method of treating αvβ3 integrin-mediated restenosis or αvβ5 integrin-mediated restinosis in a mammal in need of such treatment, comprising administering to said mammal an effective amount of a compound of claim 1.

26. A method of treating αvβ3 integrin-mediated inflammation or αvβ5 integrin-mediated inflammation in a mammal in need of such treatment, comprising administering to said mammal an effective amount of a compound of claim 1.

27. A method of treating αvβ3 integrin-mediated macular degeneration or αvβ5 integrin-mediated macular degeneration in a mammal in need of such treatment, comprising administering to said mammal an effective amount of a compound of claim 1.

28. A method of treating αvβ3 integrin-mediated diabetic retinopathy or αvβ5 integrin-mediated diabetic retinopathy in a mammal in need of such treatment, comprising administering to said mammal an effective amount of a compound of claim 1.

29. A method of treating αvβ3 integrin-mediated rheumatoid arthritis or αvβ5 integrin-mediated rheumatoid arthritis in a mammal in need of such treatment, comprising administering to said mammal an effective amount of a compound of claim 1.

30. A process for preparing a tyrosine alkoxyguanidine compound of claim 1, comprising:
reacting a compound of Formula V:

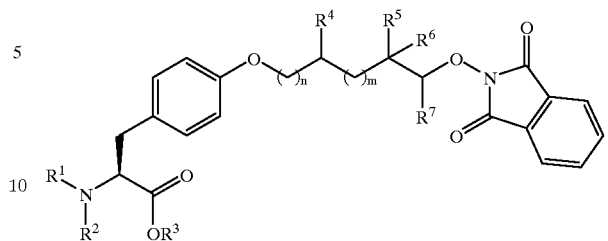

or a salt, hydrate, solvate or prodrug thereof, wherein $R^1$, $R^2$, $R^3$, $R^4$, $R^5$, $R^6$, $R^7$, m and n are as defined in claim 1, with a deprotection reagent and a guanidinylating reagent, to form a compound of Formula VI:

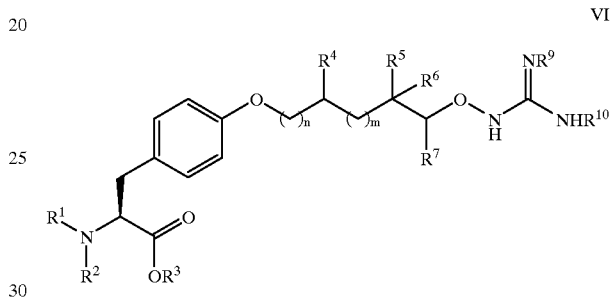

or a salt, hydrate, solvate or prodrug thereof, where $R^1$, $R^2$, $R^3$, $R^4$, $R^5$, $R^6$, $R^7$, $R^9$, $R^{10}$, m and n are as defined in claim 1.

31. The process of claim 30, wherein said deprotection reagent is hydrazine, or methylamine.

32. The process of claim 30, wherein said guanidinylating reagent is aminoiminosulfonic acid, 1H-pyrazole-1-carboxamidine hydrochloride, N,N'-bis(tert-butoxycarbonyl)-S-methylisothiourea, or N—$R^9$, N-$R^{10}$-1H-pyrazole-1-carboxamidine, where $R^9$ and $R^{10}$ are defined as in claim 1.

33. A compound of claim 1, where $R^8$ is hydrogen.

* * * * *

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Title page,
Item [56], OTHER PUBLICATIONS,
Please delete "α" and insert therein -- $α_v$ --.
Delete the second "Niiya, K. et al., "Increased Surface Expression of the Membrane Glycoprotein IIb/IIIa Complex Induced by Platelet Activation. Relationship to the Binding of Fibrinogen and Platelet Aggeregation," *Blood* 70:475-483 (1987)."

Column 2,
Line 31, please delete "Lancet" and insert therein -- *Lancet* --.

Column 4,
Line 28, please delete "97106971" and insert therein -- 97/106791 --.

Column 7,
Lines 53-54, please delete "$C_{6-10}$ar($C_{2-6}$alkenyl" and insert therein
-- $C_{6-10}$ ar($C_{2-6}$)alkenyl --.
Line 57, please delete "$C_{6-10}$ ar($C_{6-10}$)alkyl" and insert therein -- $C_{6-10}$ ar($C_{1-6}$)alkyl --.

Column 8,
Lines 18-19, please delete "2-chloro4-(trifluoromethyl)phenyl" and insert therein
-- 2-chloro-4-(trifluoromethyl)phenyl --.
Line 20, please delete "2,6dichlorophenyl" and insert therein -- 2,6-dichlorophenyl --.
Line 21, please delete "3,4dibromophenyl" and insert therein -- 3,4-dibromophenyl --.
Line 28, please delete "2,2,5,7,8-pentamethyl-chroma6-yl" and insert therein
-- 2,2,5,7,8-pentamethyl-chroma-6-yl --.
Lines 42 and 52, please delete "$C_{1-6}$ aryl" and insert therein -- $C_{6-10}$ aryl --.

Column 9,
Line 1, please delete "m" and insert therein -- n --.

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Columns 19 and 20,
SCHEME IV, please delete:

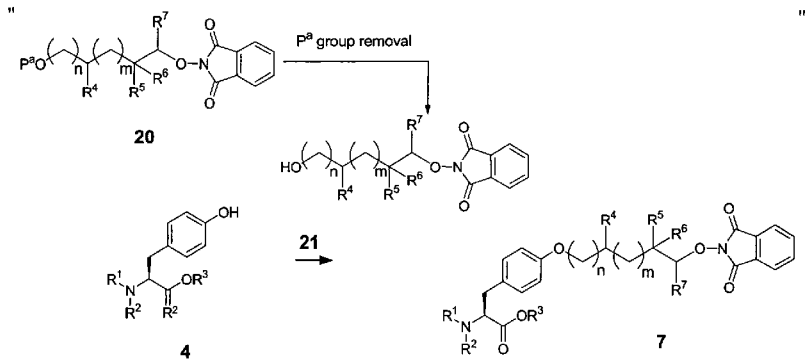

and insert therein,

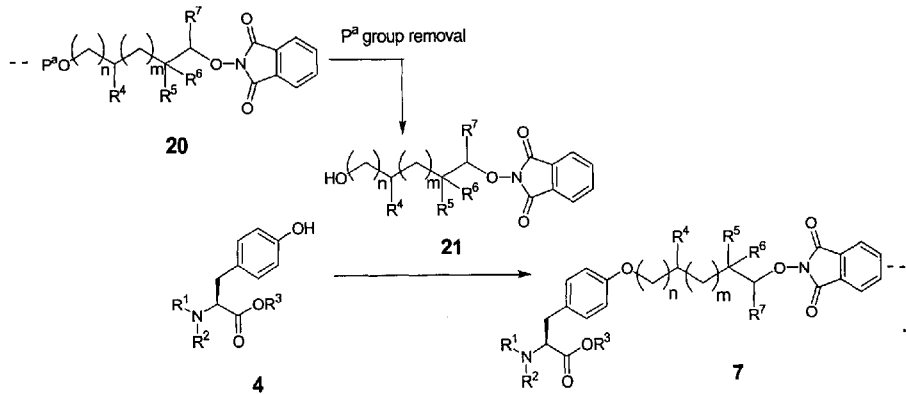

Column 20,
Lines 32 and 35, please delete "$p^a$" and insert therein -- $P^a$ --.
Line 37, please delete "maybe" and insert therein -- may be --.
Line 46, please delete "$p^a$" and insert therein -- $P^a$ --.

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Column 21,
Line 8, please delete "$R^{10)}$" and insert therein -- $R^{10}$ --.
Line 26, please delete "$(R^{12}SO^2)^2O$" and insert therein -- $(R^{12}SO_2)_2O$ --.
Line 62, please delete "Pa" and insert therein -- $P^a$ --.

Column 24,
Line 22, please delete "ail" and insert therein -- art --.
Line 25, please delete "s" and insert therein -- as --.
Line 34, please delete "potassium," and insert therein -- potassium --.

Column 26,
Lines 27-29, please delete "(2S)-3-{4-[3-(1,3-dioxoisoindolin-2-yloxy)propoxy]phenyl}-2-[(phenylmethoxy[]carbonylamino]propanoate" and insert therein -- (2S)-3-{4-[3-(1,3-dioxoisoindolin-2-yloxy)propoxy]phenyl}-2-[(phenylmethoxy)carbonylamino] propanoate --.
Line 31, please delete "(0.1 86 mL)" and insert therein -- (0.186 mL) --.
Line 40, please delete "(m, 5H)" and insert therein -- (m, 1H) --.

Column 27,
Line 46, please delete "21" and insert therein -- 2H) --.

Column 31,
Lines 28-30, please delete "(2S)-3-{4-[3-(aminooxy)propoxy]phenyl)-2-[(phenylmethoxy)carbonylamino]propanote" and insert therein
-- (2S)-3-{4-[3-(aminooxy)propoxy]phenyl}-2-[(phenylmethoxy)carbonylamino] propanoate --.
Line 42, after "(s,18H)", insert -- . --.
Lines 58-60, please delete "(2E)-3-{[3-(4-{(2S)-2-(methoxycarbonyl)-2-[(phenylmethoxy)carbonylamino]ethyl    }phenoxy)propoxy]-amino-2-aza-3-[(tert-butoxycarbonylamino]prop-2-enoate" and insert therein
-- (2E)-3-{[3-(4-{(2S)-2-(methoxycarbonyl)-2-[(phenylmethoxy)carbonylamino]ethyl} phenoxy)propoxy]-amino-2-aza-3-[(tert-butoxy)carbonylamino]prop-2-enoate --.

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Column 32,
Line 29, please delete "155mL (60 mmol)" and insert therein -- 155 µL (60 µmol) --.
Line 33, please delete "31 mL (180 mmol)" and insert therein -- 31 µL (180 µmol) --.
Line 34, please delete "(90 mmol)" and insert therein -- (90 µmol) --.
Line 35, please delete "300 mL" and insert therein -- 300 µL --.
Line 43, please delete "240 mL" and insert therein -- 240 µL --.
Line 44, please delete "120 mL (240 mmol)" and insert therein -- 120 µL (240 µmol) --.
Line 46, please delete "400 mL (292 mmol)" and insert therein -- 400 µL (292 µmol) --.
Lines 48-49, please delete "(300 mLx3)" and insert therein -- (300 µLx3) --.
Line 51, please delete "200 mL" and insert therein -- 200 µL --.
Line 52, please delete "400 mL" and insert therein -- 400 µL --.

Column 34,
Lines 51-52, below EXAMPLE 6, please delete "(2S)-3-{4-[3-(Amieinoaminooxy) propoxy]phenyl}-2-{[5-chloro(2- thienyl))sulfonly]amino}propanoic" and insert therein -- (2S)-3-{4-[3-(Amidinoaminooxy)propoxy]phenyl}-2-{[5-chloro(2-thienyl) sulfonyl]amino}propanoic --.

Column 35,
Lines 39-40, below EXAMPLE 8 please delete "(2S)-3-{4-[3-( Amidinoaminooxy ) propoxy ] pheny l}-2-([(3,5-dichloro-2-hydroxyphenyl)sulfonyl]amino}propanoic" and insert therein -- (2S)-3-{4-[3-( Amidinoaminooxy)propoxy]phenyl}-2-{[(3,5-dichloro-2-hydroxyphenyl)sulfonyl]amino}propanoic --.

Column 38,
Lines 3-5, below EXAMPLE 13, please delete "(2S)-3-{4-[3-(Amidinoaminooxy) propoxy]phenyl}-2(}[2,4,6-tris(methylethyl)phenyl]sulfonyl}amino)propanoic" and insert therein -- (2S)-3-{4-[3-( Amidinoaminooxy)propoxy]phenyl}-2-({[2,4,6-tris (methylethyl)phenyl]sulfonyl}amino)propanoic --.
Line 18, please delete "400 Hz" and insert therein -- 400 MHz --.
Line 19, please delete "brs" and insert therein -- br s --.

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Column 39,
Lines 44-46, below EXAMPLE 17, please delete "(2S)-2-({[2-(Acetylamino)-4 methyl(1,3-thiazol-5-yl)]sulfonyl}amino)-3-{4-[3-(amidinoaminooxy)propoxy]phenyl} propanoic" and insert therein -- (2S)-2-({[2-(Acetylamino)-4-methyl(1,3-thiazol-5-yl)]sulfonyl}amino)-3-{4- [3-(amidinoaminooxy)propoxyl]phenyl}propanoic --.

Column 40,
Line 19, please delete "(br 4H)" and insert therein -- (br s, 4H) --.

Column 41,
Line 60, please delete "400 Hz" and insert therein -- 400 MHz --.
Line 64, please delete "13.81 H," and insert therein -- 13.81 Hz, --.

Column 44,
Line 50, please delete "MH" and insert therein -- MHz --.
Line 55, please delete $C_{19}H_{22}Cl_2N_{4O6}S$" and insert therein -- $C_{19}H_{22}Cl_2N_4O_6S$ --.

Column 48,
In the beginning of line 61, please delete "2H," and insert therein -- 2H), --.

Column 51,
Lines 28-29, below EXAMPLE 43, please delete "3-{[((IS)-2-{4-[3-Amidinoaminooxy) propoxyl]phenyl}-1-carboxyethyl)amino]sulfonyl}benzoic" and insert therein -- 3-{[(((1S)-2-{4-[3-Amidinoaminooxy)propoxyl]phenyl}-1-carboxyethyl)amino] sulfonyl}benzoic --.

Column 52,
Line 6, please delete "$C_{20}H_{27}ClN_4O_6S$" and insert therein -- $C_{21}H_{27}ClN_4O_6S$ --.
Line 31, please delete the first "Hz," of the line.

Column 54,
Line 60, please delete "400 Hz" and insert therein -- 400 MHz --.

UNITED STATES PATENT AND TRADEMARK OFFICE
CERTIFICATE OF CORRECTION

PATENT NO. : 6,344,484 B1  Page 6 of 8
DATED : February 5, 2002
INVENTOR(S) : Tomczuk et al.

It is certified that error appears in the above-identified patent and that said Letters Patent is hereby corrected as shown below:

Column 56,
Line 25, please delete "brs" and insert therein -- br s --.
Line 26, please delete "(d, J=2H)" and insert therein -- (d, J=7.99 Hz, 2H) --.
Lines 40-41, below EXAMPLE 55, please delete "(2S)-3-{4-[3-(Amidinoaminoozy) propoxy]phenyl}-2-[(methylsulfonyl)amino]propanoic" and insert therein
-- (2S)-3-{4-[3-(Amidinoaminooxy)propoxy]phenyl}-2-[(methylsulfonyl)amino] propanoic --.

Column 57,
Line 45, please delete "d, J=4.50," and insert therein -- dt, J=4.50, --.

Column 58,
Line 65, please delete "1 3.84 Hz" and insert therein -- 13.84 Hz --.

Column 62,
Line 43, please delete "Hz, 22H)" and insert therein -- Hz, 2H) --.

Column 63,
Example 71, please delete

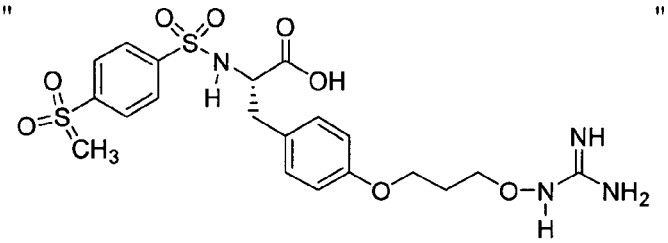

and insert therein

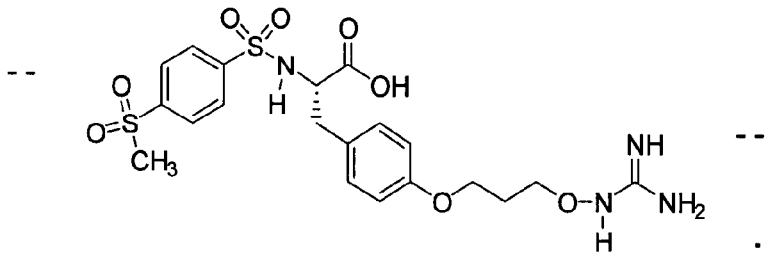

Line 28, please delete "$C_{20}H_{26}N_4O_8S$" and insert therein -- $C_{20}H_{26}N_4O_8S_2$ --.

UNITED STATES PATENT AND TRADEMARK OFFICE
CERTIFICATE OF CORRECTION

PATENT NO. : 6,344,484 B1
DATED : February 5, 2002
INVENTOR(S) : Tomczuk et al.

It is certified that error appears in the above-identified patent and that said Letters Patent is hereby corrected as shown below:

Column 68,
Lines 36-38, below EXAMPLE 81, please delete "(2S)-3-{4-[3- ( Amidinoaminooxy)propoxy]phenyl}-2-{[(6chloro-2-methylphenyl)sulfonyl]amino}propanoic" and insert therein -- (2S)-3-{4-[3- ( Amidinoaminooxy)propoxy]phenyl}-2-{[(6-chloro-2-methylphenyl)sulfonyl]amino}propanoic --.

Column 69,
Line 19, after the first "d" of the line, please insert -- , --.

Column 71,
Line 63, please delete "4.04, t" and insert therein -- 4.04 (t --.

Column 72,
Line 20, please delete "(d, J=2.07 H," and insert therein -- (d, J=2.07 Hz, --.
Line 43, after "J=9.42 Hz", please insert -- , --.

Column 75,
Lines 14-16, below EXAMPLE 96, please delete "(2S)-3-{4-[3-(Amidinoaminooxy)propoxy]phenyl}-2-{[(5-fluloro-2-methylphenyl)sulfonyl]amino}propanoic" and insert therein -- (2S)-3-{4-[3-(Amidinoaminooxy)propoxy]phenyl}-2-{[(5-fluoro-2-methylphenyl)sulfonyl]amino}propanoic --.
Line 63, after "J=6.37 Hz,", please insert -- 2H), --.

Column 76,
EXAMPLE 98, please delete " 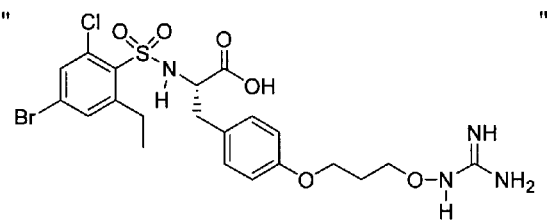 "

and insert 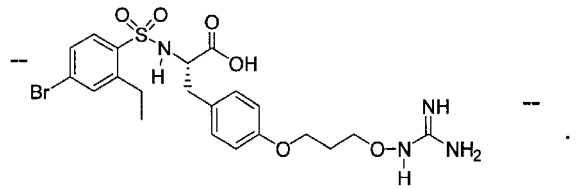 --.

UNITED STATES PATENT AND TRADEMARK OFFICE
CERTIFICATE OF CORRECTION

PATENT NO.  : 6,344,484 B1
DATED       : February 5, 2002
INVENTOR(S) : Tomczuk et al.

It is certified that error appears in the above-identified patent and that said Letters Patent is hereby corrected as shown below:

Column 78,
Line 64, please delete "$\mu$/mL" and insert therein -- $\mu$g/mL --.

Column 79,
Line 29, please delete "Nm" and insert -- nM --.

Column 84,
Lines 28-30, please delete "2S)-3-{4-[3-(Amidinoaminooxy)propoxy]phenyl}-2-{[(2-methylphenyl)sulfonyl]-amino}propanoic" and insert therein -- (2S)-3-{4-[3-(Amidinoaminooxy)propoxy]phenyl}-2-{[(2-methylphenyl)sulfonyl]-amino}propanoic --.

Column 87,
Line 21, please delete "restinosis" and insert therein -- restenosis --.

Signed and Sealed this

Twenty-fifth Day of March, 2003

JAMES E. ROGAN
*Director of the United States Patent and Trademark Office*